United States Patent
Dietz

(10) Patent No.: US 11,525,013 B2
(45) Date of Patent: *Dec. 13, 2022

(54) DISINTEGRATED AND DECOMPACTED CELLULOSE-BASED VEGETABLE FIBRE MATERIALS USE AND METHOD FOR ACQUISITION AND PRODUCTION

(71) Applicant: Max Dietz, Wiesbaden (DE)

(72) Inventor: Max Dietz, Wiesbaden (DE)

(73) Assignee: Max Dietz, Wiesbaden (DE)

( * ) Notice: Subject to any disclaimer, the term of this patent is extended or adjusted under 35 U.S.C. 154(b) by 135 days.

This patent is subject to a terminal disclaimer.

(21) Appl. No.: 16/498,474

(22) PCT Filed: Mar. 27, 2018

(86) PCT No.: PCT/EP2018/057843
§ 371 (c)(1),
(2) Date: Sep. 27, 2019

(87) PCT Pub. No.: WO2018/178121
PCT Pub. Date: Oct. 4, 2018

(65) Prior Publication Data
US 2021/0108000 A1  Apr. 15, 2021

(30) Foreign Application Priority Data

Mar. 28, 2017 (DE) ................... 10 2017 003 176.2
Dec. 13, 2017 (EP) ................................. 17207166

(51) Int. Cl.
| | | |
|---|---|---|
| *C08B 1/00* | (2006.01) | |
| *A23L 33/24* | (2016.01) | |
| *A23L 33/22* | (2016.01) | |
| *A23L 29/262* | (2016.01) | |
| *A61P 1/10* | (2006.01) | |
| *A61P 1/00* | (2006.01) | |
| *A21D 2/18* | (2006.01) | |
| *A21D 13/06* | (2017.01) | |
| *A23C 9/154* | (2006.01) | |
| *A61K 8/02* | (2006.01) | |
| *A61K 8/73* | (2006.01) | |
| *A61K 31/717* | (2006.01) | |
| *A61Q 19/00* | (2006.01) | |
| *C08B 15/00* | (2006.01) | |
| *C12N 5/00* | (2006.01) | |

(52) U.S. Cl.
CPC .............. *C08B 1/003* (2013.01); *A21D 2/188* (2013.01); *A21D 13/06* (2013.01); *A23C 9/1544* (2013.01); *A23L 29/262* (2016.08); *A23L 33/22* (2016.08); *A23L 33/24* (2016.08); *A61K 8/027* (2013.01); *A61K 8/731* (2013.01); *A61K 31/717* (2013.01); *A61P 1/00* (2018.01); *A61P 1/10* (2018.01); *A61Q 19/00* (2013.01); *C08B 15/00* (2013.01); *C12N 5/0068* (2013.01); *A23V 2002/00* (2013.01); *C12N 2533/78* (2013.01)

(58) Field of Classification Search
CPC ......... C08B 1/003; C08B 15/00; A23L 33/24; A23L 33/22; A23L 29/262; A61P 1/10; A61P 1/00; A21D 2/188; A21D 13/06; A23C 9/1544; A61K 8/027; A61K 8/731; A61K 31/717; A61Q 19/00; C12N 5/0068; C12N 2533/78; A23V 2002/00
See application file for complete search history.

(56) References Cited

U.S. PATENT DOCUMENTS

| | | |
|---|---|---|
| 4,923,981 A | 5/1990 | Weibel |
| 5,964,983 A | 10/1999 | Dinand |
| 6,379,446 B1 * | 4/2002 | Andersen .................. C08L 1/02 106/137.1 |
| 2004/0009263 A1 * | 1/2004 | Liu .......................... A23J 1/12 426/55 |
| 2005/0074542 A1 | 4/2005 | Lundberg |
| 2015/0361616 A1 | 12/2015 | Essaddam |

FOREIGN PATENT DOCUMENTS

GB   2103224   *   2/1983

OTHER PUBLICATIONS

International Search Report and Written Opinion for International Patent Application No. PCT/EP2018/057843 dated May 28, 2018, 10 pages.

* cited by examiner

*Primary Examiner* — Shirley V Gembeh

(74) *Attorney, Agent, or Firm* — Amin, Turocy & Watson, LLP

(57) ABSTRACT

The invention relates to separated, decompacted, cellulose-based fibres acquired from a vegetable raw material, wherein the separated, decompacted, cellulose-based fibres have an aspect ratio after soaking in water of longitudinal diameter to transverse diameter of 1:1 to 1000:1 and a water-binding capacity of >200 wt. % and a water retention capacity of >50%, and a method for acquiring and producing these separated, decompacted cellulose-based fibres. The purification method involves incubation of the vegetable material with an aqueous decomposition solution containing at least one dissolved amino acid and/or peptide with 2-50 amino acids to decompose the compacted cellulose-based fibres.

13 Claims, No Drawings

DISINTEGRATED AND DECOMPACTED CELLULOSE-BASED VEGETABLE FIBRE MATERIALS USE AND METHOD FOR ACQUISITION AND PRODUCTION

BACKGROUND

Functional foods are becoming increasingly important in supplying the world's population with food, as dietary and nutritional habits have changed dramatically, especially in the developed world. Although the amount of nutrients are sufficient to meet energy needs and metabolism in industrialized nations, the composition of dietary ingredients has changed in such a way that the content of roughage continues to decline. The consumption of low-roughage foods is also often due to a lack of alternative food choices or for logistic reasons. A low-roughage diet correlates inversely with the incidence of cardiovascular diseases and the occurrence of colon cancer. A low-roughage diet also means that the feeling of satiety during/after food intake is less pronounced and/or occurs later than in a high-roughage diet. The WHO recommends a daily consumption of 30 g roughage. According to recent surveys, this nutritional goal is not achieved in the majority of the population living in industrialized nations.

Roughage comprises a group of food components that cannot be digested and/or absorbed in the human digestive tract, or only to a small extent. This may be inorganic material, e.g. clays or other minerals or complex-bound organic material, such as lignin-based shells. The majority of indigestible material in plant foods, as reported in the literature, consists of polymeric carbohydrates that are not digested and absorbed by the carnivore's digestive tract. Even if a diet is chosen that consists largely of vegetables, the recommended consumption of roughage is not possible or only at the expense of increased calorie intake.

The problem of inadequate supply of roughage occurs in particular in the preparation of processed foods, such as meat substitutes or protein-based preparations. On the other hand, nutrients with a high content of protein are suitable for a balanced diet in the context of weight loss or weight control diets, and are also very useful as a nutrient source with a good shelf life for areas where malnutrition occurs.

Roughage contributes significantly to stool mass and stool consistency. This makes it understandable why people with a low-roughage diet are more likely to suffer from chronic constipation. The incidence of chronic constipation increases with age. Therefore, a higher consumption of roughage-containing foods is recommended especially in the elderly. Due to the nature and the amount of suitable nutrients required for this, however, this recommendation can usually not be implemented. Alternatively, swelling agents are offered, such as psyllium husks, which have a high water-binding capacity but have only a low calorific value. The consumption of these swelling agents in an amount to ensure an adequate and soft stool consistency can hardly be implemented in practice, since the swelling, which is accompanied by the formation of slime, leads to an unpleasant mouthfeel. There is therefore a great need for alternative sources of roughage which can be used in functional foods without causing any sensory quality loss or undesirable deterioration in the consistency of a roughage-added foodstuff. Furthermore, there is a great need for edible roughage with stool-regulating properties, while simultaneously having a pleasant mouthfeel. By combining nutrients or processed foodstuff as needed could eliminate logistical, temporal or monetary problems associated with adequately suppling nutritional components.

So if a sufficient amount of roughage is to be provided by the intake of food, it is necessary that it does not lead to a reduction in the qualitative/sensory properties of the food while maintaining the functional properties of the roughage. For this purpose, cellulose products are offered and are already used for food preparation. Such cellulose products are obtained in the prior art from a degradation of wood or woody (lignified) plant materials. Here cellulose products have to be differentiated which either have been chemically digested (degraded) and/or modified and are offered as cellulose derivatives, which are also referred to below as cellulose ethers or cellulose preparations, which have a defined molecular weight and geometric dimensions, or which are prepared by grinding of stalk mass or husks, which are hereinafter called cellulose fibers. The addition of cellulosic products to food is allowed worldwide; however, there are reports that chronic consumption of methylcellulose can lead to a chronic inflammatory process of the colon wall, which could promote the development of cancer. Long-term studies on cellulose fibers, which were obtained by grinding plant-based husk and stem mass, are not available.

The presence of solids in liquids or food is already perceived by receptors of the oral mucosa starting from particle sizes of 15 micrometer. In order not to cause any undesired sensory effect, cellulose fibers which are intended for food preparation are offered with fiber lengths of less than 100 μm and preferably of <30 μm. Despite a high water uptake volume of such cellulosic fibers, they cause an unpleasant mouthfeel when consumed alone. Therefore, it is not practical or acceptable to add prior art cellulosic fibers in that amount that is necessary in order to meet the recommended daily needs of roughage/dietary fiber. Due to the solubility of cellulose preparations and the high water binding capacity, the daily requirement of dietary fiber can not be achieved by cellulose derivatives. There is therefore a great need for the provision of roughage in the form of dietary fiber which does not result in any undesirable sensory or functional effects when used in food preparations. Although functional effects in the preparation of foodstuffs and food preparation can be achieved with cellulosic products of the prior art, as a general rule, the nutrients used in an original preparation can not be reduced, or not to a significant extent, or replaced by the cellulose products because cellulosic products do not provide the functional properties desired or required in the preparations. For example, while soups or sauces can be thickened by the use of cellulose products, it is not possible to dispense with the use of starch or other digested carbohydrates without loss of sufficient sensory quality. The same applies to applications in fat-containing food preparations, such as in a dairy ice cream or a chocolate cream. Further, the prior art cellulosic products are not suitable for stable coating or loading with other dietary supplements because of their limited uptake capacity. Therefore, there is a great need for the provision of dietary fiber, with which food preparations can be produced, while saving in particular high-calorie food ingredients but maintaining or improving the functional properties or quality. There is also a great need for low-calorie or calorie-free dietary fiber, which can be used as a functionally equivalent replacement for food components in food preparations.

Another problem which is known in the production or further processing of dissolved/degraded or swollen cellulose is the occurrence of a hornification, which occurs in particular when the cellulose is dried and decisively unfavorably alters the properties of the cellulose product, for example, leading to a significant decrease in swellability. There is therefore a considerable need for processes which can counteract or completely or partially reverse the formation of hornification of cellulose preparations.

In many areas, there are compounds/substances/organisms that are sensitive to dehydration and must be protected from it. Methods are known from the prior art with which this can be ensured. These include a vapor impermeable seal or embedding in water-based gels. Methods by which compounds/substances/organisms can be incorporated into a preparation which is taste-neutral and suitable for human consumption are nonexistent.

This is especially true for microorganisms that are to be kept viable under storage conditions and where therefore, among others, an exchange of air gases is also required. There is therefore a great need for a carrier/storage material with which desiccation-sensitive compounds/structures and/or microorganisms can be preserved over a longer period of time and at the same time a sufficient material exchange can take place and/or is a suitable carrier material for a food preparation.

DESCRIPTION

Cellulose is the most abundant biopolymer on earth. It is synthesized by plants and essentially serves to support and stabilize the entire organism of plants. Therefore these polymers are combined in parallel fibrils and are cross-linked with each other and usually exist over long distances as a continuous macromolecule. In addition, these linear structural and retaining filaments are subdivided by an enclosing lignin-based separating layer, which on the one hand has a strong hydrophobicity and thus protects against dissolution, e.g. by decay, and on the other hand, assures the structural stability of the enclosed cellulose fiber bundles.

The combination of fibrils into bundles and bundle compounds, combined with the formation of lignin layers, leads to an irreversible process, which is also known by the term "lignification". Lignified cellulose fibrils are hard, hydrophobic and can only be partially broken up by concentrated lye or acid under high temperatures and elevated pressure.

For example, for a digestion/degradation of cellulose, e.g. for the purpose of pulp or paper production, the lignin is dissolved and removed by known wet chemical digestion/degradation methods, such as the Kraft method. From the wood pulp fibrillar cellulose fibers are obtained, which have only a low swelling capacity.

Cellulose is a polymer which is a homopolysaccharide with 1→4-β-glucosidically linked anhydro-D-glucose units and is thus water insoluble and has hydrophobic properties due to its structure. For utilization, therefore, derivatives of cellulose fibers are prepared by mechanically comminuting and hydrolyzing them, as well as by esterification of the hydroxy groups to water-soluble cellulose esters, cellulose acetates or cellulose nitrates. Depending on the degree of esterification, these have strongly hydrophilic to hydrophobic properties.

Cellulose derivatives which have hydrophilic properties are completely soluble in water and, due to their large hydrodynamic diameter, already in small quantities greatly increase the viscosity of the liquid in which they are dissolved. Only a few grams/liter in water is sufficient to produce a high-viscosity colloidal solution. Functionalization of the cellulose derivatives with hydrophobic side groups, such as methyl or propyl groups, whereby compounds are obtained, such as hydroxyethyl cellulose (HEC), hydroxypropyl cellulose (HPC), or cellulose mixed ethers, e.g. methyl ethyl cellulose (MEC), hydroxyethylmethyl cellulose (HEMC), hydroxypropyl methyl cellulose (HPMC) hydroxypropylmethyl cellulose (HPMC), reduces the swelling volume. However, this leads to an altered sensory perceptibility of such derivatives. It is a common feature of the synthetically produced cellulose derivatives that they have a fibrillar structural architecture which basically corresponds to that of their plant material they derive from.

It has now been found, however, that plants also form tissue-like structures, which are present in different compartments and functional units of plant structures and in this case bind together or limit the functional or structural units. Such structural or functional units can be, e.g. starch granules or oleosomes in seeds or germs. The results of the investigation suggest that such tissue-like structures, which are also referred to below as "cellulose-based fibers", are bound with carbohydrates and proteins via electrostatic forces. At present, minerals such as calcium or zinc or inorganic compounds, such as sulfates or nitrogen-containing compounds, as well as organic compounds, such as free carboxylic acids, e.g. phytic acid, are involved in complex formation/compaction, which are responsible for the structural cohesion of the various organic components/constituents.

It is to be regarded as probable that molecular groups are present on the surfaces of the cellulose-based structures according to the invention which enable electrostatic or covalent bonding with other plant constituents. Therefore, these tissue-like structures are not cellulose fibers in the chemical sense, but cellulose-based fibers with functional surface compounds and surface properties, which guarantee certain functionalities according to their place of origin and can therefore also be regarded as functionalized tissue-like structures. It has been found that such functionalized tissue-like structures or cellulose-based fibers have a plurality of functional groups, such as free OH, SH, NH, or $PO_4$ groups or covalently bonded compounds are linked with reactive/functional groups, e.g. with amino sugar residues or amino acids, which in turn allow interaction with other compounds. It has been found that such cellulose-based fibers differ chemically from cellulose fibers present in lignified or woody plant materials and, depending on their origin and functionality, have different constituents or ligands with which they produce electrostatic or covalent bonds. In addition, it has been found that cellulose-based fibers in the molecular dimensions and their branching structure differ significantly from cellulose fibers. It has been shown that both, the three-dimensional structures and the surface properties are crucial for the resulting functional properties of such cellulose-based fibers. The cellulose-based fibers according to the invention thus differ both structurally and chemically from cellulose fibers which can be obtained, for example, from wood by a pulping process from the prior art.^

It has also been shown that complex interactions exist with other organic or inorganic compounds, which are caused by various hydrophilic or hydrophobic forces and the sponge- or coral-like three-dimensional structure of the cellulose-based fibers. Furthermore, it has been found that such binding energies also exist for gases such as oxygen or carbon dioxide. However, the three-dimensional structures of the cellulose-based fibers also cause a high affinity and thus poor detachability of compounds or substances or organisms which adhere to the cellulose-based fibers. The cellulose-based fibers according to the invention fulfill functional tasks, for example in blossoms, seeds or fruits of plants. It has been found that their proportion of the organic matter in which they are present can vary considerably, for example, less than 5% by weight, e.g. in the pulp of a watermelon, to over 70 wt % in the stalk of some types of cabbage.

From the prior art, no methods are known with which the cellulose-based fibers according to the invention can be dissolved out of the organic matrix of non-lignified plant-based starting materials and obtained in a pure form, while retaining the functionality that existed in the starting material. It has been attempted to extract the cellulose-based fibers from non-woody plant products by methods used for the production of cellulose from wood. Such prior art techniques include digestion/degradation by lyes and acids under simultaneous heating. Studies utilizing seeds, kernels, fruits and vegetables were performed, attempting to digest with an alkaline and acid sulfite digestion process and by boiling with alkalis (NaOH, $NH_3$) and acids (HCl, $H_2SO_4$). This resulted in the formation of organic agglomerates that were no longer mechanically/physically separable, which was very likely due to coagulation and degeneration/degradation of the protein and carbohydrates contained in the plant-based starting material. Therefore, such methods are not suitable for unlocking of non-lignified plant-based starting materials containing the cellulose-based fibers according to the invention, or for their obtainment and production respectively. Furthermore, no relevant separation of the carbohydrates and/or proteins contained in the starting material could be achieved with both, an alkali-lye-based and an acid-based digestion process. Also, after performing such digestion processes, cellulose-based fibers could not be separated even, if a large aqueous dispensing volume was used, so that they were not released/decompacted from the other plant constituents and there was a caking/hornification of the resulting mass during drying, which could be hydrated again only very slowly and for the most part incompletely in an aqueous medium.

Furthermore, attempts were made to separate the cellulose-based fibers by grinding techniques in conjunction with air separation and screening. For this purpose, press cake of soy and rapeseed as well as freeze-dried mesosperm of squash and carrots were used, which had been finely ground with a cutting knife and a ball mill. The resulting particles were 95% by weight <100 µm. Fractional sieving was carried out with a vibrating sieve machine (Retsch, Germany) with sieve dimensions of 75, 50 and 25 µm. Furthermore, air classification was carried out (fine classifier CFS 5, Netsch, Germany). For all fractions obtained, the chemical analysis showed the presence of >15% by weight of carbohydrates and/or proteins. The tasting of such fractions revealed the presence of a strong odor and taste similar to that of the starting product. After incorporation of such fractions in water, the water phase was very turbid and colored in some.

In the analysis of the aqueous suspension, proteins and soluble carbohydrates could be detected. Furthermore, the fibers exhibited a very rapid sedimentation behavior. Furthermore, the majority of particles was present in the form of swollen macroscopically visible aggregates. Thus, cellulose-based plant fibers which are still complexed with the original constituents of the plant-based starting material, such as carbohydrates, proteins or flavorings, are not suitable for a sensorially neutral food preparation and also do not have the desired functional properties.

Further attempts to obtain and work up cellulose-based fibers from plant-based starting materials by various processes which appear to be applicable in the prior art revealed further limitations of such processes, which lead to a considerable restriction of the usability of the cellulose-based fiber martials obtained. Thus, the mechanically comminuted plant-based starting materials were treated by repeated washing with alkaline solutions (NaOH, $NH_3$), whereby a partial separation of proteins and carbohydrates was achieved. After drying, the resulting aggregates were hard and could be ground only with great energy input. The resulting flour showed only low swelling capacity. It has been shown that hornification of fractions or all of the cellulose-based fibers is responsible for this. The process of hornification is known for cellulose fibers in the cellulose processing and is caused by irreversible changes on the cellulose fibers, if they have previously been maximally water-swollen and were present in a microporous form. As a result of capillary forces between individual fibrils, hydrogen bonds are formed so that there is the development of areas that can no longer swell (see Jayme, G, Hunger, G: The Fiber-to-Fiber Bonding of the Paper Texture in the Electron-Optical Image.) Paper 11 (1957), No. 7/8, 140-145 Thode, E F, Chase, A J, Hu, Y: Dey adsorption on wood pulp. IV. Note on effect of drying pulp on specific dye adsorption Tapp1 38 (1955), No 2, 88-89).

Surprisingly, it has been found that complete or almost complete separation of water-soluble proteins, carbohydrates and other organic compounds and minerals from cellulose-based fibers of non-woody plant-based starting materials is possible by aqueous solutions of amino acids and/or peptides and without a relevant energy input, while the cellulose-based fibers retain their original three-dimensional structures, hereby providing the special functional properties which are not achieved by fibrillar cellulose fibers.

Furthermore, it has surprisingly been found that cellulose-based plant fibers which can be obtained with aqueous amino acid and/or peptide solutions, which are decompacted and freed from adhering easily water-soluble carbohydrates or proteins, have optimal functional properties which are significantly better as those of cellulosic fibers obtained from processes by mechanical or wet-chemical pulping methods. Furthermore, it has surprisingly been found that the obtainable cellulose-based fibers are free or nearly free of water-soluble flavors and/or colorants which can be rinsed out in an aqueous medium. Furthermore, it surprisingly turned out that hornification of the cellulose-based fibers obtainable by one of the processes according to the invention does not take place or only to a small extent in a drying process if one of the processes according to the invention was used to produce the cellulose-based fibers.

It is therefore the object of the invention to obtain and produce cellulose-based plant-based fibers which have a high water-binding and retention capacity and a high emulsifying capacity.

It is a further object of the invention to obtain and produce cellulose-based plant-based fibers which are free of accompanying substances (other plant constituents) and which do not release any sensory perceptible flavors or colorants into an aqueous medium. Furthermore, it is also the object of the invention to provide a method with which the hornification of cellulose-based fibers can be prevented or reduced or reversed.

The object is achieved by the technical description and the examples of methods for obtaining and producing cellulose-based fibers by means of aqueous unlocking solutions containing amino acids and/or peptides.

The present invention therefore relates to unlocked, decompacted, cellulose-based fibers obtained from a plant-based starting material, wherein the unlocked and decompacted cellulose-based fibers have an aspect ratio after swelling in water from the longitudinal diameter to the transverse diameter of 1:1 to 1000:1 and have a water binding capacity of >200% by weight and a water retention capacity of >50%.

Furthermore, the present invention relates to a process for obtaining and producing unlocked and decompacted cellulose-based fibers whereby the process comprises the following steps:

a) providing a disintegrated or non-disintegrated plant-based starting material containing compacted cellulose-based fibers, compacted with at least one organic compound selected from:

readily water-soluble organic compounds comprising proteins and carbohydrates; and or poorly water-soluble organic compounds comprising complex carbohydrates; and or water-insoluble organic solids comprising lignin-rich shells, a1) disintegration of the non-disintegrated plant-based starting material as from step a) to obtain a penetrability of aqueous unlocking solutions and wettability of the compacted cellulose-based fibers by means of a thermal and/or a mechanical and/or an aqueous disintegration process, to obtain a dry or moist disintegrated plant starting material, b) impregnation of the disintegrated plant-based starting material from step a) or impregnation of the plant-based starting material from step a1) after thermal and/or mechanical and/or aqueous disintegration until obtaining a moisture content of greater than 20% by weight and complete hydration of the readily soluble organic compounds with an aqueous unlocking solution of dissolved unlocking substances containing at least one dissolved amino acid with a molar mass of less than 400 g/mol and a solubility of at least 35 g/L in water at 20° C. and/or peptides from 2 to 50 of these amino acids for unlocking the compacted cellulose-based fibers, c1) suspending and mixing the impregnated disintegrated plant-based starting material of step b) in an aqueous dispensing volume having a weight ratio to the dry matter of the starting material of 2:1 to 300:1 and decompacting the unlocked, compacted, cellulose-based fibers in the dispensing volume until a hydration volume of the unlocked cellulose-based fibers of >200% by volume is reached in order to obtain isolated unlocked, decompacted, cellulose-based fibers, c2) in the case of the presence of water-insoluble organic solids according to step a), separation of the unlocked, decompacted, cellulose-based fibers of step c1) from the water-insoluble organic solids, d1) separation of the unlocked, decompacted, cellulose-based fibers by filtration and/or centrifugation from the suspension of step c1) or c2) and obtaining unlocked, decompacted, cellulose-based fibers, d2) drying of the unlocked, decompacted, cellulose-based fibers.

Preference is given to a process according to the invention wherein the readily water-soluble organic compounds have a water solubility of >100 g/L at 20° C., preferably >140 g/L at 20° C., and the poorly water-soluble organic compounds have a water solubility of <100 g/L at 20° C., preferably of <75 g/L at 20° C.

Non-digestible carbohydrate polymers are the major constituent of non-resorbable dietary fiber. There is an inadequate dietary fiber intake associated with the diet of people living in industrialized countries due to modern food preparation. Cellulosic fiber derived from pulping lignocellulosic and milling stalks and husks of crops are also used in food preparations, but when more than 1 to 3 wt % is added, unwanted sensory perceptions are experienced when eating such food preparations and/or the quality of the food preparation is adversely affected. So for example, admixing 2% by weight of hydroxy-cellulose to a meatball preparation has a strong thickening effect, which causes the product to fall apart during cooking or when used in a pudding preparation caused an unacceptable solidification of the product. In the case of cellulosic fibers from the milling of stalks or husks, the addition of >3 wt % normally led to the perception of a flour-like solid and a disturbed mouthfeel with a reduction in the perceptibility of aroma characteristics that were decisive for a qualitative evaluation of the prepared products. Due to the resulting volume and consistency, it was not possible to provide more than 50% by weight of the daily recommended amounts of dietary fiber through the addition of hydroxy- or methyl-cellulose preparations to food.

In attempts to fill the supply gap of dietary fiber with cellulosic fibers made from delignified wood pulp or ligneous stalks and husks via an additive to food preparations, it was found that this was either impracticable or was accompanied by an impairment of intestinal activity.

Particularly, when supplementing cellulosic fibers obtained from stems and husks to a normal diet in an amount that equals an adequate amount for a high-fiber diet, disturbances of intestinal activity and stool consistency occurred, so that a sufficient a long-term supply of an adequate amount of roughage by using those cellulose fibers was largely not tolerated. Surprisingly, the processes according to the invention for obtaining cellulose-based fibers have been used to produce decompacted and functional cellulose-based fibers which have extremely advantageous effects in the preparation of foods and in the human digestive system.

The problem is solved by unlocked, decompacted and functional cellulose-based plant-based fibers, which are characterized by the formation of three-dimensional structures by the absorption of water, a water binding capacity of >200% by weight and/or water retention capacity of >50%, absence of readily water-soluble carbohydrates and proteins, absence of the release of flavoring agents or colorants into a water phase, and can be obtained from an aqueous disintegration and/or unlocking and/or purification process.

Functional in this context means that the cellulose-based fibers produced have adjustable properties, such as rapid hydratability of dried cellulose-based fibers in water, surface properties that ensure interaction with different media or allows uptake of microorganisms, which develop their biological activity herein.

Preferred are unlocked, decompacted, cellulose-based plant-based fibers, which are characterized by formation of three-dimensional structures by the absorption of water and/or a water binding capacity of >200% by weight and/or water retention of >50% and/or absence (<1% by weight) of readily soluble carbohydrates and proteins and/or the absence of flavoring agents or colorants that are released into a water phase.

Surprisingly, it has also been found that the cellulose-based fibers produced according to the invention make it possible to obtain ideal conditions for inclusion/uptake of substances/compounds or microorganisms to protect them from dehydration. It has been found that in cellulose-based fibers, produced in this manner, substances/compounds or microorganisms accumulate/adhere on their surfaces spontaneously in a highly advantageous manner and without relevant technical effort, or they can be deposited onto or incorporated into the geometric structures/interior spaces of the cellulose-based fibers.

Due to the high water binding capacity and the high water holding capacity, the incorporated compounds/substances/organisms are protected from dehydration which inactivates or destroys such compounds/substances/organisms, considerably longer than was the case with preparations of the prior art, such as cellulosic fibers, nutrient media, such as Gujar or Aglinate. Also, the mass transfer, which is required, for example, for the maintenance of cell metabolism, was still possible in a binding/introduction into/onto cellulose-based fibers produced according to the invention, while this was the case to a much lesser extent or not at all for the other materials investigated. The incorporated compounds/substances/organisms showed, even after 2 weeks of cool storage in a humid chamber, functionality or metabolic activity that was unchanged through the end of the experiment, which was not possible when stored with preparations of the prior art. Therefore, cellulose-based fibers prepared according to the invention are suitable for the adherence and/or incorporation of compounds/substances/organisms that are sensitive to dehydration in order to preserve them and/or to stabilize their integrity and functionality as well as to preserve them. In addition, it could be shown that the cellulose-based fibers onto/into which compounds/substances/organisms have been deposited are very well suited for the preparation of foodstuffs. For example, it has been shown that baker's yeasts were very stably placed in the interiors of the decompacted cellulose-based fibers and had the same metabolic activity after 14 days of storage in a vessel under refrigerated conditions after reactivation, as the same amount of yeasts at the starting point. Furthermore, it was easier to distribute the yeast cultures while making dough than was the case with fresh baker's yeast. In the baked goods prepared hereby a more pleasant mouthfeel/chewing sensation and a lower perceptibility of the yeast or the yeast-typical flavor was found compared to when using yeast alone.

Preference is given to cellulose-based fibers for up-take/incorporation/adherence of compounds/substances/organisms which are sensitive to dehydration and can be preserved by the uptake/incorporation/adhesion into/onto cellulose-based fibers.

Preference is given to cellulose-based fibers for keeping fresh and preserving compounds/substances/organisms.

Preference is given to cellulose-based fibers for maintaining or increasing the functionality and/or the growth of microorganisms.

Preferred are cellulose-based fibers for the preservation/incorporation/flavor control of compounds/substances/organisms for use in food.

Preference is given to cellulose-based fibers for binding odorants and flavoring agents. Non-digestible carbohydrates, which include the cellulose-based fibers of the present invention, account for the major component of the bulk of the dietary fiber in the average human diet. Not digestible means that these compounds can not be cleaved by enzymes of the human gastrointestinal tract, such as amylases, and thus be cleaved into C-6-sugar compounds that are absorbable. Thus, the cellulose-based fibers remain essentially unchanged in the intestinal contents and thus become part of the stool. In particular, by their ability to bind water they are important in regulating the consistency of the colon content. The water binding capacity of the intestinal contents also determines the passage time of the feces produced in the colon. The importance of a high-fiber diet for the prevention of bowel disease and intestinal transit problems has been clearly demonstrated in a large number of clinical studies. It was thus shown that the rate of colorectal cancer can be reduced by a high-fiber diet. Furthermore, a reduction of elevated cholesterol levels and associated cardiovascular diseases was demonstrated. Also known is a stool-regulating function of fiber-rich roughage in chronic constipation, which is particularly prevalent in the elderly. Furthermore, pro-biotic effects of a high-fiber diet are known, which result from the partial degradation of complex carbohydrates by the microbiome of the human colon. Such effects are attributed to a lower incidences of cancer outside the colon, e.g. by short-chain fatty acids or phytosterols that arise from the breakdown of complex carbohydrates or are released and can pass through the colon wall. It is therefore strongly recommended by the World Health Associations and the FDA to consume dietary fiber equivalent to a dry matter amount of fiber of 30 g per day. This goal is not achieved in the vast majority of dietary forms practiced in industrialized nations or in emerging economies. There is an inverse correlation between dietary fiber consumption and the incidence and severity of obesity and diabetes mellitus, as well as mortality. However, a practical implementability of the recommendations on dietary fiber content of the diet can not be enforce for various reasons, such as a lack offers for employees or an implicit social behavior, despite all the information and explanations known for this purpose. Also, country-policy appeals to the food industry have remained without sustainable effect due to the limited selection for roughage from the state of the art and the demands made on the sensory properties of the product by consumers.

Thus, there is a great need to provide roughage that can be added to or supplemented with food preparations that meet the sensory and functional demands placed on a nutritional product, thereby increasing the amount of dietary fiber in the foodstuff.

Surprisingly, it has been found that the cellulose-based fibers obtained and produced according to the invention are excellently suitable to completely cover the daily requirement of dietary fiber which should be consumed by humans. It could be shown in practical application that both the daily requirement of dietary fiber only from cellulose-based fibers according to the invention, as well as by using it as a supplement to a normal diet, is practicable and can be performed in an acceptable form by the consumer. For example, an otherwise roughage-free diet was prepared by using the produced cellulose-based fibers (28 to 36 g daily weight (dry weight)) together with proteins and minerals and consumed as an exclusive food in a satiating amount by subjects over a period of 4 weeks. The food preparation was rated good or very good by all participants and did not lead to any unwanted side effects. However, an average weight reduction of 5.3 kg was registered in all participants, despite a subjectively perceived sufficient and satisfying food intake. In another study in which a total of 15 g (dry weight) of the produced cellulose-based fibers per day were added to or blended into or prepared with the various foods consumed during the course of the day by the panelists, the practicability of using the cellulose-based fibers and the qualitative/sensory properties of the food prepared hereby have been rated as good to very good. Also in the participants of this investigation, an unintentional weight loss of 3.2 kg occurred on average. Remarkably, none of the participants had digestive problems, in particular no adverse changes in stool frequency and stool consistency.

In those subjects, an appropriate food preparation was attempted using the same amount of cellulosic products (cellulose derivates) made from wood pulp or stalks and husk pulp. In the study on the sole use of these preparations as source of roughage, the food preparations were largely considered to be non-consumable by the participants, so that this study was not feasible. In the study on the addition of cellulose fibers to a common diet, the study was prematurely discontinued by the majority of participants due to poor sensory evaluation or a significantly lower daily level of cellulose preparations was consumed than intended. There was no statistically significant weight reduction in the participants of these studies during the study period. In a further study, participants suffering from chronic constipation received cellulose-based fibers prepared according to the invention or cellulosic fibers over a period of 14 days in an amount between 8 and 15 g (dry weight) per day as a supplement to their usual diet. Participants taking cellulose-based fibers manufactured according to the invention showed an increase in stool frequency and a softening of stool consistency after 3 days, which continued over the rest of the course. All participants rated the addition of cellulose-based fibers as practicable and pleasant. A significant weight reduction of 900 g was documented among the study participants. In contrast, study participation of those who took cellulose preparations was prematurely discontinued in 30%. A positive effect on the stool frequency or stool consistency was reported by 12% of the participants; 56% of the participants reported no relevant effect and 32% of the subjects reported an adverse effect (in particular an increase in stool consistency). There was no weight reduction.

Surprisingly, it has thus been found that cellulose-based fibers can be recovered, purified and prepared by one of the methods according to the invention from various plant products and plant waste materials and that simultaneously the cellulose-based fibers are odorless and taste-neutral and have excellent functional properties in food products, as well as they have positive stool-regulating properties. It is therefore the object of the invention to provide methods and processes to obtain and produce of functional or functionalizable cellulose-based fibers.

Thus it was possible to show that by using cellulose-based fibers produced according to the invention flour could be saved by the same order of magnitude as the amount of cellulose-based fibers added. By cellulose-based fibers, which were coated with a leavening agent, such as yeast or sodium bicarbonate, on the inner surfaces, an increase in the baking volume and a more uniform distribution of the air chambers formed could be achieved. At the same time, baked goods which were made with the cellulose-based fibers had a higher resistance to indentations and, compared to the reference recipe, had a better mouthfeel and a more harmonious taste impression.

Furthermore, it has been shown that cellulose-based fibers produced according to the invention can be used as a fat substitute in food preparations. In this case, at least 50% by weight of the amount of fats and oils can be reduced to achieve the same preparation volume and equivalent or better sensory and qualitative characteristics, as is the case with preparations with the otherwise customary amounts of fats or oils.

DETAILED DESCRIPTION

Due to their common origin, the different parts of the constituents in plant seeds, grains or fruits, which consist essentially of the constituents proteins, soluble carbohydrates, oils/fats and complex carbohydrates, are gap-free connected with each other via hydrophilic and hydrophobic electrostatic forces, but also by covalent bonds. A selective and complete separation of the constituents is therefore not possible by mechanical methods. The term polymeric carbohydrates is understood to mean cyclic C-6 compounds which are linked to polymers 1→4-β-glucosidically and can not be cleaved by enzymes in humans or only in small amounts. They are therefore not split in the digestive tract of humans and carnivores and thus are excreted undigested again with the stool. It has now been found that aqueous solutions, in which amino acids and/or peptides are dissolved, are rapidly and completely absorbed by non-lignified plant-based starting materials, such as press residues of seeds and grains or ground products, such as flour from grains or kernels or from the pulp or the disintegrated organic mass of vegetables or fruits or tubers, in all of which the above mentioned constituents are present together in a dense/compacted composite, and that upon hydration allows complete separation of the various constituents. This result is surprising since the amino acid and/or peptide solutions cause only a small change in the surface tension of the aqueous solutions and substances which have a high surfactant activity, such as SDS, did not lead to a similar result. Furthermore, it was surprising that a disintegration/unlocking and separation of the constituents can be carried out at room temperature or even under cooled conditions and that for the separation of the constituents no relevant energy input is required. Since there is no need to use a mechanical disintegration process when carrying out an unlocking process alone, the filigree structures of the cellulose-based fibers present in the starting materials are not damaged or destroyed. In particular, these are responsible for water binding and retention properties that have existed in the starting materials. These tissue-like structures are obtained by separation according to the invention without mechanical division in the form of separable cellulose-based fibers with a broad distribution of dimensions. Furthermore, together with and from the cellulose-based fibers, in addition to oils/fats and proteins, colorants and flavoring agents are dissolved or detached, respectively, and can thereby be dissolved in an aqueous medium and separated from the cellulose-based fibers. Only after the separation of these components of the plant constituents from the compacted cellulose-based fibers is it possible to recognize the fine structures of these corpuscular structures by means of analytical methods, such as particle size determination or imaging methods, such as a light or electron microscopy and make it recognizable that these structures are coherent and three-dimensional. Imaging of the cellulose-based fibers has shown that these are filigree structures that form coral-like or web-like coherent 3-dimensional formations. It has also been possible to show that such cellulose-based fibers have numerous side groups or functional groups and compounds whose compositions differ from one species to another. Mass spectroscopic analysis has shown that there are also variable proportions of the elements nitrogen, phosphorus, sulfur, sodium, chloride, calcium, magnesium, zinc, copper, iron, manganese and other elements, in addition to carbon, oxygen and hydrogen. As is also shown below, the filigree, three-dimensional, tissue-like cellulose-based fiber structures obtainable by the processes according to the invention differ both chemically and in terms of their physical and performance properties compared to cellulose or cellulose fibers or cellulose derivatives, which are obtained, for example, from the pulping of wood.

Preference is given to the obtainment and production of cellulose-based fibers containing functional groups and compounds containing at least one of the elements nitrogen, phosphorus, sulfur, sodium, chloride, calcium, magnesium, zinc, copper, iron or manganese.

Preference is given to a process in which cellulose-based fibers having tissue-like 3-dimensional structures are obtained and/or produced, with an aspect ratio of 1:1 to 1:1,000.

Preference is given to cellulose-based fibers with tissue-like 3-dimensional structures. The unlocking solutions according to the invention preferably contain naturally occurring amino acids and/or peptides which consist of or contain these amino acids in a completely dissolved form in water. Preferably, this is a solution of one, two or more amino acid (s) and/or peptides (s), in the single and/or total concentration in a range of 10 µmol/1 to 3 mol/l, more preferably between 1 mmol/l and 1 mol/and more preferably between 0.1 mol/and 0.5 mol/l. These may be L- or D-forms or racemates. Preferred is the use of the L-form. Preferred are alanine, arginine, asparagine, aspartic acid, glutamine, glutamic acid, glycine, histidine, isoleucine, leucine, lysine, phenylalanine, proline, serine, threonine, tryptophan, tyrosine and valine. The amino acids arginine, lysine, histidine and glutamine are particularly preferred. Particularly preferred are cationic amino acids and amino acid derivatives such as arginine and its derivatives. The peptides which can be used according to the invention may be di-, tri- and/or polypeptides. The peptides of the invention have at least one functional group that can bind or bind a proton. The preferred molecular weight is below 500 kDa, more preferably <250 kDa, more preferably <100 kDa and particularly preferably <1000 Da. The preferred functional groups are in particular a guanidine, amidine, amine, amide, ammonium, hydrazino, hydrazono, hydroxyimino or nitro group. The amino acids may have a single functional group or more of the same class of compounds or one or more functional group (s) of different classes of compounds. The amino acids and peptides according to the invention preferably have at least one positively charged group or have a positive total charge. Particularly preferred are peptides with cationic functional groups. Preferably, the pH of the cationic amino acid or peptide solution ranges from 7 to 14, more preferably between 8 and 13, and more preferably between 8.5 and 12.5. In one embodiment, the pH can be adjusted to any pH range between 6 and 14 by the addition of an acid or a base. Acids and bases known in the art may be used, such as caustic soda or HCl. Particularly preferred peptides contain at least one of the amino acids arginine, lysine, histidine and glutamine in any number and sequential order. Particular preference is therefore given to amino acids and/or derivatives containing at least one guadinino and/or amidino group.

The guanidino group is the chemical residue $H_2N$—C(NH)—NH— and its cyclic forms, and the amidino group is the chemical residue $H_2N$—C(NH)— and its cyclic forms. Preference is given to guanidino compounds which, in addition to the guanidino group, have at least one carboxylate group (—COOH). Further, it is preferable that the carboxylate group (s) is separated from the guanidino group in the molecule by at least one carbon atom. Also preferred are amidino compounds which have at least one carboxylate group (—COOH) in addition to the amidino group. It is further preferred if the carboxylate group (s) is separated from the amidino group in the molecule by at least one carbon atom.

Also suitable are di-, tri- or oligopeptides as well as polypeptides which are composed of one, two or more amino acids. Preferred are short-chained peptides, e.g., RDG. Particularly preferred are peptides which consist of amino acids which have both hydrophobic and hydrophilic side groups, such as (letters according to the amino acid nomenclature) GLK, QHM, KSF, ACG, HML, SPR, EHP or SFA. Further particularly preferred are peptides which have both hydrophobic and cationic and/or anionic side groups, such as RDG, BCAA, NCR, HIS, SPR, EHP or SFA. Further examples with 4 amino acids are NCQA, SIHC, DCGA, TSVR, HIMS or RNIF or with 5 amino acids are HHGQC, STYHK, DCQHR, HHKSS, TSSHH, NSRR. Particularly preferred are RDG, SKH or RRC.

Preference is given to a process in which aqueous solutions of one or more amino acid (s) and/or of one or more peptides are used for obtaining and/or producing cellulose-based fibers.

Preference is given to a method in which aqueous solutions of one or more cationic amino acid (s) and/or of a cationic peptide or of several cationic peptides are used for obtaining and/or producing cellulose-based fibers.

Preference is given to a process in which the at least one dissolved amino acid according to step b) has a molar mass in the range from 75 g/mol to 350 g/mol and/or a solubility of at least 75 g/l in water at 20° C. and/or it is an α-, β- or γ-amino acid and/or proteinogenic and/or non-proteinogenic amino acid.

Preferred is a process in which one or more aqueous solution (s) having a pH between 7 and 14 is used for obtaining and/or producing of cellulose-based fibers.

Preference is given to a process in which the aqueous unlocking solution according to step a1) and/or step b) has a pH between 7 and 14.

In one embodiment, the aqueous solutions may contain auxiliary compounds, e.g. alcohols, antioxidants or surfactants. Preferred alcohols are methanol, ethanol, polyethylene glycol. Preferred surfactants are urea, thiourea, sodium lauryl sulfate and DMSO.

Preference is given to a process in which, in addition to one or more amino acid (s) and/or a peptide or a plurality of peptides, auxiliary compounds are contained in the aqueous solutions for obtaining and/or producing cellulose-based fibers.

It has been found that in order to obtain the cellulose-based fibers according to the invention it is necessary that the unlocking solutions containing amino acid and/or peptide solutions completely penetrate the plant-based starting material, that means the interfaces between the compacted cellulose-based fibers and the components/constituents to be separated are wetted and thus hydrated by the amino acid and/or peptide solutions. This may necessitate the initial disintegration of structures that prevent such wetting, e.g. because they are impermeable to water. This applies in particular to kernels or nuts. Here, a disintegration of one or more cladding structures can be done preferably by mechanical fragmentation, e.g. by pressing or impacting. A disintegration may also be required in water-containing starting materials, such as in carrots or tuber. Preferred for this purpose are mechanical and/or thermal processes. Mechanical methods which can be applied to the plant-based starting materials for disintegration include, for example, pressing, grinding or cutting procedures.

Preference is given to a process for obtaining and producing cellulose-based fibers, in which a disintegration of the plant-based starting material takes place.

The analysis of the ingredients/constituents present in the preferred plant-based starting material showed that the constituents contained herein can be grouped into:
- readily water-soluble organic compounds comprising proteins and carbohydrates; and or
- poorly water-soluble organic compounds comprising complex carbohydrates; and or
- water-insoluble organic solids comprising lignin-rich shells.

Therefore, preferred are decompacted cellulose-based fibers obtained from a plant-based starting material which, in addition to compacted cellulose-based fibers, contains at least one organic compound selected from:
- readily water-soluble organic compounds comprising proteins and carbohydrates; and or
- poorly water-soluble organic compounds comprising complex carbohydrates; and or
- water-insoluble organic solids comprising lignin-rich shells.

Further preferred is a process wherein the recovery and production of unlocked decompacted cellulose-based fibers is achieved from a disintegrated or non-disintegrated plant-based starting material containing compacted cellulose-based fibers compacted with at least one organic compound selected from:
- readily water-soluble organic compounds comprising proteins and carbohydrates; and or
- poorly water-soluble organic compounds comprising complex carbohydrates; and or
- water-insoluble organic solids comprising lignin-rich shells, Preference is given to a process for obtaining and producing cellulose-based fibers, in which disintegration is carried out by means of one or more chemical and/or physical processes which can be combined or carried out in chronological order.

Preference is given to a process for obtaining and producing cellulose-based fibers, in which disintegration of the plant-based starting material takes place by means of a thermal and/or mechanical treatment.

Preference is given to a process for obtaining and producing cellulose-based fibers, in which disintegration/unlocking of plant-based starting material takes place with or together with an aqueous solution for disintegration/unlocking of the starting material and its constituents.

Preference is given to a process for obtaining and producing cellulose-based fibers, in which disintegration of plant-based starting material takes place with or together with an aqueous solution of one or more amino acid (s) and/or of one or more peptides.

In a preferred embodiment, disintegration is accomplished by means of a thermal process, such as by heating the plant-based starting material in a water bath. In one embodiment, the thermal disintegration takes place in an aqueous solution for disintegration or unlocking of the starting material. Such a disintegration/unlocking process can be applied, for example, to all plant-based starting materials that have a closed shell/seed coat that substantially can not be penetrated by water. This process can also be used in plant-based starting materials, in which the cellulose-based fibers have thermolabile connections with each other or with other structures that can be disintegrated e.g. by a cooking process and thus are dissolvable.

Surprisingly, it has been found that especially sulfites accelerate the disintegration process. Thus, it was found that a 1 wt % solution of sodium sulfite, which was added in a volume ratio of 3:1 to a rapeseed press cake and a thermal disintegration was carried out at a temperature of 85° C., a softening of the particulate starting material was accomplished already after 20 minutes, while using a pure water phase, such a softening was not present even after 3 hours. Surprisingly, it was then found that with a simultaneous use of a 0.1 molar arginine solution and sodium sulfite in a 1 wt % concentration, the duration for obtaining of cellulose-based fibers could be further reduced, recognizable by a test of dispensability of the cellulose-based fibers in a dispensing volume. Further, it was found that the obtained fiber mass was markedly brighter when a sulfite or a surfactant was present in the aqueous unlocking solution, as compared to the sole use of an amino acid and/or peptide for disintegration. Preference is therefore given to the use of auxiliary compounds for disintegration, such as sulfites, sulfates, ionic and nonionic surfactants.

Preference is given to the use of sulfites for disintegration and/or unlocking of plant-based starting material, for accelerating the disintegration/unlocking and/or bleaching of the starting material.

In another preferred embodiment, disintegration and/or unlocking of the tissue-like structures takes place following drying of the plant-based starting material. Mechanical processes, such as a chopping or a grinding, are preferred here. This is advantageous because amino acid and/or peptide solutions can thereby be arranged more rapidly at the boundary layers within the plant-based starting material.

Disintegration and/or disintegration and unlocking of the plant-based starting material is/are preferably always to be provided if, by immersing the plant-based starting material into one of the amino acid and/or peptide solutions according to the invention or applying the latter, unlocking and obtainment of cellulose-based fibers is not or not completely possible.

Preference is given to a process in which the plant-based starting material is provided in step a1):

Disintegration of the non-disintegrated plant-based starting material to obtain a permeability of aqueous unlocking solutions and wettability of the compacted cellulose-based fibers by a thermal and/or a mechanical and/or an aqueous disintegration process, wherein a dry or moist disintegrated plant-based starting material is obtained.

In one embodiment, the amino acid and/or peptide solutions are preferably added in a mass ratio of between 0.3:1 and 3:1 to the plant-based starting material that can be penetrated by the solutions and mixed therewith, such that a complete wetting/impregnation of the organic starting material is ensured. However, it is also possible to select significantly larger volume ratios, in particular if the constituents of the starting material that are to be dissolved and separated from the cellulose-based fibers are to be dissolved and separated with this aqueous solution. Preferably, a mixing process is used to ensure complete penetration of the plant-based starting material. The temperature at which this takes place can be chosen freely, preferred are temperatures between 4° and 90° C., more preferably between 15° and 70° C. and more preferably between 20° and 45° C. The duration of the penetration phase naturally depends on the type and nature of the plant-based starting material. Preferred is a duration between 5 minutes and 24 hours, more preferably between 10 minutes and 12 hours and more preferably between 20 minutes and 6 hours.

Preference is given to a process for obtaining and producing cellulose-based fibers, in which complete penetration/wetting of the plant-based starting material is achieved with an aqueous solution of one or more amino acids and/or of one or more peptides.

Surprisingly, it can be checked by means of a very simple test procedure whether sufficient hydration or disconnection/detachment of the components of the plant-based starting material from/of the cellulose-based fibers has taken place by suspending a sample of the mixture in a sufficiently large volume of water. Sufficiently large means a water volume ratio of at least 5:1. In one embodiment, in a plant-based starting material which also contains lignin-based shell material, sufficient separability of the plant-based starting material from the cellulose-based fibers is accomplished if, after the mixing process in the water phase, rapid sedimentation of the lignin-rich shells takes place and the macroscopically visible cellulose-based fibers have no or only a slight tendency to settle/sediment, in the simultaneous absence of undissolved aggregates of the starting material. In another embodiment of the test study, which is used in particular in plant-based starting materials which does not contain lignin-rich shells, the suspension is filtered with a sieve, preferably with a sieve mesh size from 0.2 to 0.6 mm, after suspension in water, which is carried out as described above.

After physical removal of unbound water, resuspension of the cellulose-based fibers in water is performed. If, after sufficient hydration of the cellulose-based fibers, macroscopically visible fibers which have a low tendency to settle are present and the aqueous medium remains clear and colorless and at the same time there is an absence of aggregates of the starting material with undissolved readily soluble compounds on the cellulose-based fibers, sufficient detachment of the readily soluble constituents of the plant-based starting material has been accomplished. It has been found that even impregnation/wetting of the penetrable plant-based starting material, reaching a water content (moisture content) of >20% by weight, is sufficient to allow complete hydration of the readily soluble organic compounds.

Preference is given to a process in which aqueous unlocking takes place in step b): Impregnation of the disintegrated plant-based starting material from step a) or impregnation of the plant-based starting material from step a1) after thermal and/or mechanical and/or aqueous disintegration until a moisture content of greater than 20% by weight and complete hydration of the readily soluble organic compounds is achieved with an aqueous unlocking solution of dissolved unlocking substances containing at least one dissolved amino acid with a molar mass of less than 400 g/mol and a solubility of at least 35 g/L in water at 20° C. and/or peptides from 2 to 50 of these amino acids for unlocking the compacted cellulose-based fibers.

In a preferred embodiment, the obtainment of the cellulose-based fibers is accomplished by a rinsing process to separate the other constituents of the plant-based starting material from the cellulose-based fibers. This rinsing process can be done, for example, by adding a sufficiently large volume of water to the batch. Preferably, the ratio of the addition volume is more than 2:1, more preferably >4:1, and most preferably >10:1. The required volume depends on whether the specification characteristics (see methods) for the available cellulose-based fibers are achieved; this can easily be determined by analytical methods. In particular, the unlocked, decompacted cellulose-based fibers have a very high water binding capacity, which is preferably >100% by volume, more preferably >150% by volume, more preferably >200% by volume, even more preferably >300% by volume and particularly preferably >400% by volume. Unless the specification values are reached, the dispensing volume can be increased and/or the dispensing process is repeated in a further dispensing process, after prior separation of the cellulose-based fibers. Therefore, the dispensing process is performed until the required specification values are obtained. However, the dispensing volume is preferably less than 500:1, more preferably <300:1, further preferably <150:1, and further preferably <20:1. Preference is given to the use of an intensive mixer in this process step.

Preference is given to a process in which, following a complete hydration, which takes place in process step b), step c1) is carried out:

Suspending and mixing the impregnated disintegrated starting material of step b) in an aqueous dispensing volume having a weight ratio to the dry matter of the starting material of 2:1 to 300:1; and decompacting of the unlocked, compacted, cellulose-based fibers in the dispensing volume until a volume of hydration of the unlocked cellulose-based fibers of >200% by volume is achieved obtaining isolated unlocked, decompacted, cellulose-based fibers.

The rinse water is preferably removed by filtration. Particularly preferred is a filtration with a vibrating screen. Further preferred are curved screens and chamber filter presses. Also preferred is a separation of the rinse water with a decanter separator. A repetition of the rinsing process after removal of the free water phase from the cellulose-based fibers obtainable with one of the aforementioned techniques is preferred until the rinsing liquid is clear, colorless and odorless. In another preferred embodiment, the batch is placed in a sieve or other vessel with porous boundaries and water is flushed through until the rinse water is clear and colorless. Surprisingly, it has been found that the cellulose-based fibers which can be obtained and/or produced by the processes described herein are also low in taste and odor, or they were tasteless and odorless.

Preference is given to a process in which cellulose-based fibers are obtained and produced by impregnating the starting material with a solution containing dissolved amino acid and/or peptides by rinsing out soluble constituents of the plant-based starting material followed by removal of bound water which can be performed by a physical method.

Preference is given to a process for obtaining and producing cellulose-based fibers, in which the recoverable or producible cellulose-based fibers release no or almost no colorants and/or odors and/or flavoring agents to an aqueous medium in which they are suspended. These surprising properties of the recoverable or obtainable cellulose-based fibers can be determined by a visual inspection, e.g. by microscopy and by a smell and taste sensory evaluation. Also available are analytical methods of the prior art, such as turbidimetry, spectroscopy or HPLC.

Surprisingly, the cellulose-based fibers according to the invention can be almost completely retained by a sieve having a sieve mesh size which corresponds to a multiple of the mean diameter of the cellulose-based fibers. This is most likely due to a mutual entanglement of the complex three-dimensional structures of the cellulose-based fibers obtained. This greatly simplifies the rinsing out of other constituents of the plant-based starting material. In one embodiment, intermittent pressing/extrusion of the previously rinsed cellulose-based fibers is performed, thus, reducing the amount of water that is required to completely rinse the cellulose-based fibers. The rinsing process is complete and the cellulose-based fibers according to the invention are obtained when, after squeezing out the water, there is no release of soluble constituents in a water phase and the cellulose-based fibers show no or only a minimal tendency to settle after suspension in water. From the cellulose-based fibers produced according to the invention, no flavoring or coloring agents are dissolved out in water, which lead to a formation of taste or color. The decompacted cellulose-based fibers according to the invention are microscopically free of other constituents of the starting material and have three-dimensional structures with empty internal spaces. These three-dimensional structures have a coral- or sponge-like shape. The size dimensions vary depending on the starting plant-based material used. Preference is given to cellulose-based fibers having a maximum diameter of from 10 μm to 2,000 μm, more preferably from 20 μm to 1,000 μm and more preferably from 30 μm to 500 μm. Preference is given to cellulose-based fibers having a minimum diameter between 0.5 μm and 50 μm, more preferably between 1 μm and 30 μm and more preferably between 3 μm and 20 μm. Preference is given to a uniform distribution of the average cellulose-based fiber diameter over a diameter range between 5 μm and 500 μm, more preferably between 20 μm and 300 μm and more preferably between 40 μm and 200 μm. Preferred are cellulose-based fibers having an aspect ratio of maximum length and width dimensions between 1:1 and 1000:1, more preferably between 1:1 and 500:1, more preferred between 1:1 and 250:1, even more preferred between 1:1 and 180:1 and more preferred between 1:1 and 100:1. Preference is given to complex three-dimensional structures which are formed by the cellulose-based fibers.

Preference is given to a process in which disintegrated, decompacted, cellulose-based fibers are obtained which expand to three-dimensional structures upon the absorption/uptake of water.

Preferred are disintegrated, decompacted, cellulose-based fibers that form three-dimensional structures upon the absorption/uptake of water.

It has been shown that the cellulose-based fibers obtained according to the invention have the abovementioned specifications, in particular when complete or almost complete separation of all readily water-soluble compounds was accomplished. The preferred cellulose-based fibers have a content of readily water-soluble carbohydrates, proteins and flavoring agents or colorants preferably of <3% by weight, more preferably of 2% by weight, more preferably of 1% by weight and even more preferably of 0.5% by weight.

Preferred is a process in which unlocked, decompacted, cellulose-based fibers have a content of readily water-soluble carbohydrates, proteins and flavoring agents or colorants of <1% by weight.

Preferred are unlocked, decompacted, cellulose-based fibers having a content of readily water-soluble carbohydrates, proteins and flavoring agents or colorants of <1% by weight.

The disintegration/unlocking process according to the invention allows in a very advantageous manner the very easy separation of unlocked, decompacted cellulose-based fibers and other insoluble organic compounds. Non-woody starting materials often containing lignin-rich shells or husks or stalk materials which are not soluble by the process of the invention and remain stable as solid matter. These solids usually have a significantly greater volume and/or a higher specific gravity than the cellulose-based fibers according to the invention. This allows easy separation of these insoluble organic solids with prior art methods.

Preferably, a filtration process, e. g. by means of a vibrating or curved sieve or cyclone separation method, e.g. with a hydrocyclone is carried out. But it is also possible to use separation processes based on centrifugal acceleration, e. g. a sieving decanter. Therefore, in a method embodiment, the implementation of step c2) is preferred:

in the case of the presence of water-insoluble organic solids according to step a), separation of the unlocked, decompacted, cellulose-based fibers of step c1) from the water-insoluble organic solids.

In a preferred embodiment, in step d1), the removal of the bound water fraction from the cellulose-based fibers is carried out by a physical process known from the prior art. Preferably, the cellulose-based fibers which are obtained in a suspended form after process step c1) or c2) or c3) are obtained by a state-of-the-art filtration or centrifugal process. Preferred are sieve decanter or chamber filter presses. In an advantageous method embodiment, the obtainable fiber mass is also pressed out mechanically. The achievable residual moisture content depends on the process-specific requirements. Preferably, the unbound and parts of the bound water are removed. Preferably, a residual moisture content of between 30 and 200% by weight, more preferably between 40 and 150% by weight and even more preferably between 45 and 120% by weight is achieved.

Preference is given to a process in which step d1) takes place after step c1) or c2) or c3): Separation of the unlocked, decompacted, cellulose-based fibers by means of filtration and/or centrifugation from the suspension of step c1) or c2) or c3) and obtaining unlocked, decompacted cellulose-based fibers.

In another preferred embodiment, the cellulose-based fiber mass is passed from a suspension onto a porous material, thereby, applying a uniform film of the cellulose-based fibers. On the one hand, the bound water can escape through the pores and, on the other hand, a gas stream, preferably of heated air, can be passed through. As a result, a gentle drying of the resulting cellulose-based fibers is achieved. The drying by heating, or the passage of a hot air is preferably carried out at a temperature between 15° and 110° C., more preferably between 20° and 90° C. and more preferably between 35° and 75° C. In one embodiment, the drying is carried out by a freeze- and/or vacuum-drying. In another embodiment, spray drying is performed. As a result, very particularly voluminous cellulose-based fibers can be produced. In another embodiment, prior art processes for drying the cellulose-based fibers of the invention are used. Preference is given to thermal processes which involve drying at a low temperature, which is preferably <150° C., more preferably <120° C., more preferably <100° C., even more preferably <85° C. and particularly preferably <70° C. Also preferred are spray drying and vacuum drying. But also belt-/contact drying methods are preferred. The residual moisture content of the dried cellulose-based fibers is preferably between 8 and 35% by weight, more preferably between 10 and 30% by weight and more preferably between 12 and 25% by weight.

A method is preferred in which, after step d1), step d2): Drying of the unlocked, decompacted, cellulose-based fibers, it performed.

However, according to the method, it is also possible to use the cellulose-based fibers obtainable from step d1) without carrying out step d2). In a further method embodiment, after step c1) or c2) and/or after step d1) or step d2), a surface conditioning or functionalization process can be carried out in the optional process steps c3) and/or d3). For this purpose, the already unlocked and decompacted cellulose-based fibers mass is provided in a dry, partly dried, wet or suspended form and to add and mix these with one or more compounds/solutions/cultures. The appropriate process conditions must be determined specifically. Suitable compounds/microorganisms and the thereby obtainable properties of the conditioned/functionalized cellulose-based fibers are described below. Preference is given to a process in which step c3) and/or d3), which takes place after step c1 or c2) or after step d1) and/or d2), is carried out for the conditioning/functionalization of cellulose-based fibers, comprising the steps:

Providing an aqueous solution containing conditioning/functionalizing compounds comprising amino acids and/or peptides, carbon acids, carbonates, alcohols, sugar compounds, cellulose ethers, Suspending and dispensing the cellulose-based fibers from step c1 or c2) or after step d1) and/or d2), respectively, in the solution containing conditioning/functionalizing substances until surface conditioning with of the conditioning/functionalizing compounds on the inner and outer surfaces of the cellulose-based fibers is achieved, Phase separation of the conditioned/functionalized cellulose-based fibers by means of filtration and/or centrifugation, wherein in step e) conditioned and/or functionalized, unlocked, decompacted, cellulose-based fibers are obtained which have anti-static and/or hygroscopic, hydrophilic or hydrophobic and/or conductive surface properties.

Preference is given to a process in which cellulose-based fibers are obtained and produced in their natural form and/or function by an aqueous process, with solutions containing dissolved amino acid and/or peptides.

The object of the invention, the recovery of cellulose-based fibers, is accomplished by an aqueous process with which cellulose-based plant-based fibers can be obtained and produced.

According to the invention, the obtainment and production of plant-based cellulose-based fibers by a process consisting of a) providing a plant-based starting material containing cellulose-based fibers, a1) disintegration of the plant-based starting material from step a) by a thermal and/or mechanical disintegration process, b) impregnation of the disintegrated plant-based material from step a1) with an aqueous unlocking solution, c) rinsing out of soluble constituents of the plant-based starting material, d) removal of bound water by a physical process, e) obtaining cellulose-based fibers which, upon contact with water, form three-dimensional structures and release no or only minimal amounts of readily water-soluble carbohydrates and/or proteins and/or flavoring agents and/or colorants in an aqueous suspension.

It is preferred that the aqueous unlocking solution contains dissolved amino acids and/or peptides.

Therefore, the obtainment and production of plant-based cellulose-based fibers according to the invention is accomplished by a method that consists of the steps a) providing a plant-based starting material containing cellulose-based fibers, a1) disintegration of the plant-based starting material from step a) by a thermal and/or mechanical disintegration process, b) impregnation of the disintegrated plant-based material from step a1) with an aqueous unlocking solution containing dissolved amino acids and/or peptides, c) rinsing out of soluble constituents of the plant-based starting material, d) removing bound water by a physical method e) obtaining cellulose-based fibers which, upon contact with water, form three-dimensional structures and release no or only minimal amounts of readily water-soluble carbohydrates and/or proteins and/or flavoring agents and/or colorants in an aqueous suspension.

Preference is given to a process in which non-lignified (non-woody) plant-based starting material is used in process step a).

Preferred are unlocked, decompacted, cellulose-based fibers, obtainable from a non-lignified plant-based starting material.

The object of the invention is therefore to obtain unlocked decompacted cellulose-based fibers which, on the one hand, retain their natural physical properties and, on the other hand, are free of other readily soluble organic compounds and in particular of flavoring agents.

In a preferred embodiment of the method, in step b) impregnation of the disintegrated plant-based material from step a) or a1) with an aqueous unlocking solution containing dissolved amino acids and/or peptides, in which the at least one amino acid is a cationic amino acid and/or the at least a peptide contains at least one cationic amino acid.

In a preferred embodiment of the process according to the invention, the at least one dissolved amino acid according to step b) has a molar mass in the range from 70 g/mol to 400 g/mol, preferably from 75 g/mol to 350 g/mol, more preferably from 100 g/mol to 320 g/mol, more preferably from 140 g/mol to 300 g/mol and/or a solubility of at least 75 g/L in water at 20° C., preferably of at least 100 g/L in water at 20° C. and more preferably of at least 140 g/L in water at 20° C. and/or it is an $\alpha$-, $\beta$- or $\gamma$-amino acid and/or proteinogenic and/or non-proteinogenic amino acid.

Preferred is a method in which the one or more of the amino acids and/or peptides in step b) is/are one or more cationic amino acid (s) and/or peptides with cationic amino acids.

Preferred is a method in which the one or more cationic amino acid (s) is arginine and/or lysine and/or histidine and/or derivatives thereof.

In particular, it was possible to show that the water binding capacity and the water retention capacity are particularly high in an unlocking process in which cationic amino acids were present in the aqueous unlocking solution. Preferably, the amino acids are arginine, lysine and histidine.

Preference is given to a process in which cellulose-based fibers are obtained and produced which are free of odors and flavors.

Preference is given to cellulose-based fibers which expand to three-dimensional structures and contain no or only minimal amounts of readily soluble carbohydrates and/or proteins and/or flavoring agents and/or colorants.

However, the method is equally applicable to starting materials of plant-based origin, in which impregnation with an aqueous solution is already possible and therefore disintegration is not necessary in order to obtain the cellulose-based fibers according to the invention recoverable. This can be the case, for example, with press residues of an oilseed or fruits and vegetables or with dried fruit, peel products or plant materials which have been mechanically or microbially altered or have been dried and/or comminuted.

Therefore, according to the invention, the obtainment and production of plant-based cellulose-based fibers can be achieved by a method consisting of the following:

a) providing a plant-based starting material containing compacted cellulose-based fibers which can be penetrated/wetted by aqueous solutions, b) impregnation of the plant-based material from step a) with an aqueous unlocking solution containing dissolved amino acids and/or peptides c) rinsing out of soluble constituents of the plant-based starting material, d) removing bound water by a physical method e) obtaining decompacted cellulose-based fibers, which expand to three-dimensional structures upon contact with water and release no or minimal amounts of readily water-soluble carbohydrates and/or proteins and/or flavoring-agents and/or colorants in an aqueous suspension.

In a preferred process embodiment, in step b), the plant-based material from step a) is impregnated with an aqueous solution containing dissolved amino acids and/or peptides, in which the at least one amino acid is a cationic amino acid and/or the at least a peptide containing at least one cationic amino acid.

In a preferred embodiment of the process for obtaining cellulose-based fibers, the cellulose-based fibers according to the invention can be produced simultaneously. The cellulose-based fibers according to the invention are characterized by an origin of plant-based starting material according to any of the definitions disclosed herein, an aspect ratio of a longitudinal and transverse diameter of 1:1 to 1000:1 a water binding capacity of >200% by weight a proportion of chemical compounds and functional groups of >2.5% by weight which do not correspond to a polymeric carbohydrate.

In the case of the cellulose-based fibers according to the invention, at least two of the abovementioned characteristics are present at the same time.

Preference is given to a process in which unlocked, decompacted, cellulose-based fibers are obtained which contain more than 2.5% by weight of chemical compounds and functional groups comprising nitrogen, phosphorus, sulfur, sodium, chloride, calcium, magnesium, zinc, copper, iron and/or manganese, which do not correspond to a carbohydrate.

Preference is given to unlocked, decompacted, cellulose-based fibers containing more than 2.5% by weight of chemical compounds and functional groups, including nitrogen, phosphorus, sulfur, sodium, chloride, calcium, magnesium, zinc, copper, iron and or manganese, which do not correspond to a carbohydrate.

The cellulose-based fibers produced according to the invention are further distinguished by a very low fiber length weight, the coarseness, which is preferably <70 mg/100 m, more preferably <50 mg/100 m, more preferably <30 mg/100 m and even more preferably <20 mg/100 m, more preferably <15 mg/100 m, and most preferably <10 mg/100 m.

Preference is given to a process in which cellulose-based fibers having a length weight of <20 mg/100 m are obtained and/or produced.

Preference is given to a process in which cellulose-based fibers having a fiber length weight of <20 mg/100 m are obtained and/or produced which have not been subjected to a polymer-analogous reaction.

Thus, nature-identical cellulose-based fibers having a very low length weight, can be obtained, directly from an organic starting material and without a change in the polymeric structures, such as an ether-reaction, and with excellent colloidal properties.

An essential property of these functional cellulose-based fibers is their high water-binding capacity. So this is largely responsible for the stability and water retention capacity of vegetables and fruits, which consist for the most part of water, such as carrots or pumpkins. These functional properties can be retained by the obtainment and production of the cellulose-based fibers by the processes according to the invention, without the need for chemical modification of the cellulose-based fibers obtained. Such cellulose-based fibers are characterized in particular by a very high water-binding capacity and by their particularly high water retention capacity and their colloidal properties. The water binding capacity is preferably more than 200% by weight, more preferably more than 400% by weight, more preferably more than 800% by weight and more preferably more than 1000% by weight. In addition, a water retention capacity of preferably >50% by weight, more preferably of >80% by weight and more preferably of >120% by weight. The terms "water holding capacity" and "water binding capacity" are used synonymously herein.

Preference is given to a process in which, in process steps d) or e), cellulose-based fibers having a water binding capacity of >200% by weight and/or a water retention capacity of >50% by weight are obtained.

Methods for testing water binding capacity are known in the art. The water retention capacity may, among others, be tested by the cellulose-based fibers in the fully hydrated state but do not contain free water, by a layering of a thickness of 20 mm on a filter cloth. Next, a 10 cm diameter punch is placed on the mass with a defined mass weight (e.g., 1,000 grams). After 30 minutes, the residual moisture content of the compressed mass is determined. Another method is described under "Methods".

Preference is given to a process in which unlocked, decompacted, cellulose-based fibers are obtained from a plant-based starting material which has an aspect ratio after swelling in water of longitudinal diameter to transverse diameter of 1:1 to 1000:1 and a water binding capacity of >200% by weight and have a water retention capacity of >50%.

Preference is given to unlocked, decompacted, cellulose-based fibers obtained from a plant-based starting material having an aspect ratio after swelling in water of longitudinal diameter to transverse diameter of 1:1 to 1000:1 and a water binding capacity of >200% by weight and a water retention capacity of >50%.

According to the art, cellulosic pulping processes are accomplished by mechanical comminution of wood-based cellulosic material, i. e. made of wood or lignified plant components. This includes stems (stalks) and husks. As a result, it is possible to obtain high-purity cellulose fiber powders which have a defined size distribution of the fibers. It has been shown that pulping processes, such as those used for the production of cellulose according to the prior art, give fibrillar cellulose fibers which do not lead to a sensory or functionally satisfactory result. In contrast to fibrillar cellulose fibers, which are synthesized by plants for stabilizing and structural tasks and which are perceived as woody, husk-like or hard during chewing and therefore are not considered suitable for consumption, the cellulose-based fibers produced according to the invention, which are present in not lignified or lignifying plant materials, are responsible for the desired chewing and taste experience during consumption.

Thus, the cellulose-based fibers obtained and produced according to the invention are soft, nature-identical fiber materials that differ from fibrillar cellulose fibers, which are obtained, for example, from wood pulp, or from cellulose derivatives obtained by esterification and which therefore have a different chemical structure compared to the original form, are not perceived as pointed, hard or firm/unappealing in sensory perception on skin and mucous membranes In a preferred embodiment, a post-treatment of the obtained cellulose-based fibers takes place in order to confer further functional properties to the cellulose-based fibers.

In one embodiment, following the process step c1) or c2) and/or d1) or d2), the optional process step c3) and/or d3): conditioning/functionalizing the cellulose-based fibers is performed.

Preferably, a conditioning or functionalization is carried out in order to optimally adapt the wet or dried cellulose-based fibers to the application-specific conditions or to ensure a particularly rapid hydration in the various applications. In one embodiment, the surfaces of the cellulose-based fibers are made hygroscopic. Such techniques are known in the art. Thus, for example, glycerol or a sugar syrup or an amino sugar compound, which, for example, is dissolved in water, can be used, in particular if the cellulose-based fibers are to be supplied to a preparation of desserts or it can be an aqueous salt or acid solution, such as NaCl or acetic acid or a phospholipid and/or glycolipid solution, which are used, in particular, if the cellulose-based fibers are to be used for a sauce or meat preparation. In another embodiment, dissolved amino acids and/or peptides are used for conditioning. For this purpose, the decompacted cellulose-based fibers obtained in process steps c1) or c2) and/or d1) or d2) are placed and hydrated in a solution with the dissolved amino acids and/or peptides. Preferred amino acids are arginine, lysine and glutamate. In one embodiment, micro- or nano-emulsions are used for conditioning. Preference is given here to micro-emulsions or nano-emulsions which have been prepared from a guanidino- and/or amidine-group containing compound and an acid. Arginine and a carboxylic acid are preferred. Short-chain fatty acids such as lactate or adipic acid are preferred for hydrophobization of the surfaces.

Preference is given to a process for the production of plant-based cellulose-based fibers, in which hygroscopic conditioning of the inner and/or outer surfaces of the cellulose-based fibers is achieved by impregnation or immersion into a conditioning solution.

In a preferred embodiment, for this purpose, the cellulose-based fiber mass that is still wet from the previous process step, which has been dewatered by a mechanical method, such as a pressing or centrifugation with a preferred residual moisture between 5 and 100 wt %, more preferably between 10 and 80 wt % and more preferably between 25 and 60 wt %, is added to an acidic solution having a preferred pH range between 2 and 6, more preferably between 2.5 and 4, or to a basic solution having a preferred pH range between 8 and 14, more preferably between 8.5 and 12.5 or in an aqueous solution with a surfactant, such as DMSO, at a concentration of 0.1 to 20%, more preferably between 0.5 and 15%, preferably under stirring. Preference is given to the use of an intensive admixing process. Preference is given to the use of cationic or anionic amino acids and/or peptides as acid- or base-forming compounds. The duration of the conditioning is subject to individual requirements, preferred is a conditioning period of 1 minute to 3 days, more preferably from 1 hour to 24 hours. The temperature can in principle be chosen freely, preferably a temperature between 10° and 90° C., more preferably between 15° and 60° C.

Preference is given to a process for the production of plant-based cellulose-based fibers, in which the inner and/or outer surfaces are conditioned with an ionic and/or non-ionic surfactant.

Preference is given to the use of micro- or nano-emulsions for conditioning cellulose-based fibers.

Micro- or nano-emulsions can be used in any concentration and in any proportion with the cellulose-based fibers in the same way as described above.

In a further process variant, in process step c3) or d3), a reduction of pathogens, germs or toxins and/or bleaching takes place. For this purpose, compounds of the prior art can be used. Preference is given to aqueous solutions containing peroxides or chlorates. Preference is given to hydrogen peroxide or sodium hypochlorite. The required concentration and duration of exposure depend on the deactivation/decolorization to be achieved and must be determined individually.

Preferably, the conditioned cellulose-based fibers are subsequently copiously rinsed with water or a suitable solution mixture. Preferably, the conditioned and rinsed cellulose-based fibers are then dried and ground. In one embodiment, acceleration of the water reuptake after drying of the conditioned cellulose-based fibers is achieved by conditioning. This can be checked by e.g. the duration for the complete absorption of a volume of water, with which complete swelling of the dried cellulose-based fiber material is achieved. Preferably, the conditioning achieves an increase in the water reuptake rate of >100%, more preferably >200% and more preferably >300% compared to unconditioned cellulose-based fibers. In another embodiment, for example, the conditioning achieves an improvement in the adhesion of compounds, for example of sugar compounds or proteins. The adhesion/incorporation of compounds onto/into the cellulose-based fibers may be achieved as described elsewhere in this disclosure. Surprisingly, conditioning results in an improvement in the adhesion of compounds used for subsequent functionalization of the cellulose-based fibers. This is especially true for the use of micro- or nano-emulsions which are preferred for carrying out a conditioning.

Preference is given to a process for conditioning cellulose-based fibers in which, with the use of micro-emulsions or nano-emulsions, an improvement in a subsequent functionalization is achieved.

The change in the adhesion of compounds to the cellulose-based fibers can be understood by prior art methods, for example by dilution tests.

The cellulose-based fibers produced and dried according to the invention have a very rapid and complete hydratability. The hydratability can be recognized by the complete separability of the individual cellulose-based fibers, which do not exceed a maximum extension/diameter of 2,000 μm and in which there is absence of a granular or sharp/abrasive property in the sensory evaluation.

Functionalization of Cellulose-Based Fibers.

Surprisingly, the cellulose-based fibers obtained according to the invention can be functionalized very easily and effectively. In a preferred embodiment, the inventive method therefore contains optional process step c3) and/or d3): functionalizing the surfaces of the cellulose-based fibers, following the process step c1) or c2) and/or d1) or d2).

Preference is given to a process in which, after process step c1) or c2) and/or d1 or d2), the process step c3) and/or d3): functionalization of the surfaces of the cellulose-based fibers, is performed.

Suitable for this purpose are the still wet, partly dried or fully dried cellulose-based fibers obtained according to the invention with or without prior conditioning, as described herein. The cellulose-based fibers obtained and produced according to the invention are characterized by their high absorption capacity for functionalizing components, which is very likely based on the high binding capacity for water but also for lipophilic compounds (especially when using the dried cellulose-based fibers). Thus, it has been shown that a uniform and complete coating/loading of the cellulose-based fibers with proteins, carbohydrates, microorganisms or colorants from aqueous solutions or suspensions is possible. On the other hand, it could also be shown that oils and fats completely cover the inner and outer surfaces, provided that they were brought into contact directly or dissolved in a suitable solvent with the dried or partially dried cellulose-based fibers. The results from application onto or into the cellulose-based fibers differed significantly from that achieved with cellulose fibers. In comparison, a larger amount of compounds/substances could be immobilized onto or into the cellulose-based fibers produced according to the invention. When using cellulose fibers, higher concentrations of the compounds to be coated led to flaking or peeling or abrasion of the applied compounds after drying. This was virtually not the case with the cellulose-based fibers, in which at least a portion of the three-dimensional structures were completely filled with the compounds added or introduced. Therefore, it is precisely the cellulose-based fibers produced according to the invention which are very well suited to take up and trap a large amount of compounds/substances. Nevertheless, after drying the obtained and produced cellulose-based fibers could be processed as needed, e.g. into a powder. In this case, powders may preferably be produced by a milling process or by an impact crushing process. Very good results could also be achieved by spray drying, milling drying or freeze drying; therefore, processes for producing coated cellulose-based fibers which are obtained by means of spray drying, milling drying or freeze drying are preferred. However, granules or agglomerates can also be formulated by techniques known in the art. Such are particularly advantageous when a delayed release/detachment of the compounds or organisms applied to the cellulose-based fibers is desired. Thus, it could be shown that both water-soluble and fat-soluble vitamins were released only after a latency from the coated cellulose-based fibers in a suitable medium. This latency was significantly longer than that found with accordingly coated cellulosic fibers. Furthermore, it was to show that it is possible to adjust the binding of compounds/substances or living organisms to the surfaces of the cellulose-based fibers produced according to the invention. This can by accomplished, for example, by superficial coating with sugar/saccharide compounds or organic acids, such as citric acid or lactate, but also by surfactants, such as phospholipids or glycolipids or glycoglycerolipids or by chelating agents, such as EDTA. Preference is given to the application of a coupling layer with citric acid, ascorbic acid, EDTA or phospholipids.

Surprisingly, it has been found that the product properties of the cellulose-based fibers can be changed by the incorporation/adhesion of surface modifiers. For example, it has been shown that incorporation of the cellulose-based fibers obtained into aqueous solutions containing surface-active compounds leads, for example, to an increase in the volume expansion of the cellulose-based fibers and, at the same time, a markedly reduced rate of settling of such cellulose-based fibers in a liquid is achieved. Such effects could be achieved, for example, by sodium lauryl sulfate or DMSO by suspending the cellulose-based fibers in these solutions. Even after subsequent rinsing with water and drying, the cellulose-based fibers produced in this manner had a significantly larger volume and could be hydrated faster than cellulose-based fibers that have not been surface-modified after their obtainment.

In one embodiment, dried and powdered cellulose-based fibers are used for incorporation/adhesion of substances for surface functionalization and/or surface modifiers. Preferably, the powdered cellulose-based fibers are suspended in a solution/suspension of an aqueous or non-aqueous phase and stirred. The concentration of the compounds used for functionalization or surface modification is to be determined individually. The process of functionalization/surface modification preferably is maintained until complete swelling of the cellulose-based fibers has been achieved. This can be assessed, for example, on the settling behavior of the agitated fiber mass. In one embodiment the functionalized/surface-modified cellulose-based fibers are subsequently freed of unbound water, e.g. using a vibrating screen, and, if necessary, dried to a preferred residual moisture content of between 0 and 100% by weight, more preferably between 10 and 80% by weight and more preferably between 20 and 60% by weight using techniques of the prior art. If necessary, mechanical fragmentation of the dried cellulose-based fiber mass can then be carried out.

Preference is given to a process for obtaining and producing cellulose-based fibers in which a surface modification is carried out.

Preference is given to cellulose-based fibers having a surface modification.

Preference is given to a method in which the surface modification is carried out with a surface-active substance.

A modification of the properties of the cellulose-based fibers could also be effected by other compounds. Thus, a sensory perceptibility of obtained cellulose-based fibers can be significantly reduced by carboxylic acids, which were prepared in the form of micro- or nano-emulsions, when the cellulose-based fibers have been suspended herein. This also resulted in an increased absorption of lipophilic compounds, such as oils and fats. For example, it could be shown that cellulose-based fibers, which had been surface-modified with carboxylic acids, had a significantly increased oil absorption capacity. Surprisingly, it was found in experiments on the oxidation stability of carboxylic acids with double bonds, which adhered to the inner and outer surfaces of the cellulose-based fibers, that during the course of more than 8 weeks it was not possible to perceive an odor and flavor that typically occurs during oxidation of these carboxylic acids. Subsequent investigations on oils showed then further surprising effects. Thus, the addition of cellulose-based fibers that had been surface-modified with oleic acid to a paraffin oil which was stored in air for 12 weeks did not result in any sensory changes, while adding an equivalent amount of oleic acid to paraffin oil led to development of a clearly perceptible smell and taste (rancid/bitter) already after a short time. It was further surprising that in the case of a paraffin oil, to which oleic acid had been added, sensorially perceivable oxidation products did not form when cellulose-based fibers that had undergone surface modification were added simultaneously or immediately afterwards. The binding of free fatty acids and/or oxidation products onto/into the cellulose-based fibers could be found in further experiments, in particular for those cellulose-based fibers which had been surface-modified with hydrophobic and/or amphiphilic compounds, such as carboxylic acids, waxes, phospholipids, glycolipids, glycoglycerolipids or sterylglycosides. In one embodiment, lipophilic or amphiphilic compounds are brought onto/into the cellulose-based fibers by means of micro- or nano-emulsions.

The preparation of micro- and nano-emulsions is known in the art. Preference is given to nano-emulsions which consist of cationic amino acids and carboxylic acids. Arginine, lysine and histidine as well as oleic acid and linoleic acid are preferred. For the preparation of the preferred nano-emulsions, concentrations of the amino acids from 10 µmol to 0.6 mol, more preferably 50 µmol to 0.1 mol, are dissolved in water and mixed with a carboxylic acid in a ratio to the amino acid used of preferably from 0.01:1 to 1:1, more preferably 0.1:1 to 0.5:1 and stirred until a clear liquid is achieved. The micro- or nano-emulsions can be contacted in any proportion with wet, partly dried or dry cellulose-based fibers. By maintaining a sufficient contact time at a preferred temperature between 10° and 90° C., more preferably between 15° and 60° C., it can be ensured that the surfaces of the cellulose-based fibers have been completely wetted with the constituents of the micro- and nano-emulsions. Surprisingly, it could be shown that compounds which were soluble in the micro/nano-emulsions and were completely dissolved therein could be very evenly distributed in this form to the surfaces of the cellulose-based fibers. Preferred compounds which can be applied onto/into the cellulose-based fibers together with the micro/nano-emulsions, include, among others, carboxylic acids, waxes, phospholipids, mono-, di- and triglycerides, glycolipids, glycoglycerolipids, steryl glycosides or lipophilic colorants and flavoring agents. The respective concentration of the compound (s) to be dissolved in a micro-/nano-emulsion is to be determined in each case via solubility experiments. Preferred is a complete dissolution so that micelles or particles herein have a diameter of less than 200 nm. Such a surface coating gives rise to further extremely advantageous effects. For example, it has been shown that the oxidation stability of a lipid phase can be increased by such a surface modification of cellulose-based fibers. Thus, for example, a significant reduction of secondary oxidation products in camelina oil could be effected if the latter were admixed with cellulose-based fibers to which carotene or carotenoids had been incorporated/adhered. Such anti-oxidative effects could then also be demonstrated for the incorporation/adhesion of antioxidants onto/into the cellulose-based fibers. Such antioxidants are, for example, ascorbic acid.

Preference is given to surface-modified cellulose-based fibers for oxidation stabilization of lipid phases.

Preference is given to a process in which surface modification of cellulose-based fibers takes place by means of a micro-/nano-emulsion.

Surface-modified cellulose-based fibers also exhibited improved miscibility and stability with/from emulsions of lipid phases. It has been shown that cellulose-based fibers are outstandingly suitable for producing lotions, creams, ointments or pastes. Firstly, there is a very easy mixability of cellulose-based fibers into existing lotions/emulsions/creams or ointments, without destabilizing the water-in-oil or oil-in-water mixture. Such preparations retained the same turgor and shape significantly longer when exposed to air. Furthermore, the absorption behavior into the skin was significantly increased, the skin surfaces became fat-free more quickly, as was the case with the original preparations. Furthermore, only by admixture of cellulose-based fibers to lotions/creams/ointments or pastes it could be made possible to admixed aqueous solutions containing hydrophilic compounds or to admix substantially larger amounts, without subsequently causing separation. The stabilization of the formulations of lotions/creams/ointments or pastes achievable with the cellulose-based fibers was significantly better than formulations with cellulose fibers. The same applied to the skin's absorption behavior as well as the perception of the treated skin areas, which was more often described as "smooth" and "soft". Furthermore, it was shown that the moisture content of the skin and mucous membranes could be significantly increased compared to creams or lotions which did not contain the cellulose-based fibers produced according to the invention. This could be demonstrated, for example, by determining the skin electrical resistance or the electrical conductivity of the treated skin areas. The cellulose-based fibers can be admixed in any desired form to lotions/creams/ointments or pastes, for this purpose cellulose-based fibers having a residual moisture between 10 and 200% by weight are preferred, more preferably between 15 and 100% by weight, and more preferably between 20 and 80 wt %. In one embodiment, the preferred amount of cellulose-based fiber (DW) added to lotions/creams/ointments or pastes is between 0.0001:1 and 0.5:1, more preferably between 0.001:1 and 0.2:1, and more preferably between 0.01:1 and 0.1:1. The blending is carried out by prior art methods. If necessary, water or a solubilizer can be added to the formulation.

Preference is given to cellulose-based fibers for stabilizing lotions/creams/ointments or pastes.

Preference is given to cellulose-based fibers for improving the absorption behavior and/or the moisturization of/by lotions/creams/ointments or pastes onto/into skin and mucous membranes.

Surprisingly, it has been found that it is very easy to incorporate auxiliary compounds/active substances into lotions/creams/ointments or pastes by the adhesion/incorporation of compounds onto/into the cellulose-based fibers and that these are present in stable form. For example, it has been shown that a very stable and homogeneous introduction and distribution of light quantum adsorbents can be achieved in emulsions and lotions with the cellulose-based fibers. For this purpose, e.g. carotenes or ascorbic acid can be adhered/incorporated onto/into the cellulose-based fibers, which was accomplished by immersing the cellulose-based fibers into an organic solution with carotenes or an aqueous solution with ascorbic acid for 5 hours and then complete removal of the organic solvent or water or dried to a residual moisture content of 50 wt %. The cellulose-based fibers containing auxiliary compounds were then stirred into a lotion or cream for 3 hours. The preparations were applied to a radioluscent support in a defined thickness and the adsorption of UV radiation transmission was determined. In comparison with preparations in which the same preparation with cellulose fibers or cellulose ethers (only possible by using an organic solvent) or in which the compounds had been added to the lotions or creams in an appropriate concentration, the results indicated that the cellulose-based fibers achieved a much greater reduction in UV light quantum transmission.

Preference is given to cellulose-based fibers for adhesion/incorporation and/or stabilization of active substances in lotions/creams/ointments or pastes.

In further studies on the functionalizability of cellulose-based fibers obtained according to the invention, it has surprisingly been found that, in contrast to cellulose fibers, a coupling/functionalizing layer is achieved by impregnation/soaking of the cellulose-based fibers with dissolved coupling/functionalizing substances alone, so that it can be assumed that the bonding to the surfaces of the cellulose-based fibers obtained is largely via electrostatic forces. The cellulose-based fibers obtained in accordance with the present invention are capable of providing a wide range of reactive groups/compounds precisely because of the presence of a large number of compounds which are not polymeric carbohydrates and are functionalizable.

Preference is given to cellulose-based fibers which contain >/=2.5% by weight, more preferably >5% by weight, more preferably >8% by weight and even more preferably >15% by weight of functionalizable compounds/reactive groups in relation to the total mass.

It has been found that, due to the high chemical resistance of the cellulose-based fibers, it is also possible to treat the cellulose-based fibers with an acid or alkali in order to improve the incorporation of substances and compounds or immediately mix substances/compounds that are dissolved in an alkali or acid with them in order to adhere/incorporate them. In this case, the reaction temperature can be varied, since the cellulose-based fibers regain their shape and structure during cooling again even after a temperature increase to above 150° C. Compounds with which a surface coupling/functional layer can be made are known in the art. Preference is given to compounds possessing sulfur, phosphorus or OH groups, such as sulfonates, phosphates or alcohols.

A surface coating of the cellulose-based fibers with a coupling/functional layer which is effected by an electrostatic and/or covalent surface bond is preferred.

Preference is given to cellulose-based fibers having a surface coating as a coupling/functional layer for the electrostatic and/or covalent surface bonding.

Surprisingly, it has been shown that the cellulose-based fibers according to the invention are particularly suitable for the uptake/storage and cultivation of microorganisms. The preferred microorganisms are preferably useful organisms which are capable of producing and/or fermenting compounds/substances. Typical representatives of such microorganisms are, for example, glucose-degrading yeasts, such as the baker's yeast or lactose-degrading bacteria, such as *Bacillus bifidum*.

It has been shown that after incorporation/adhesion of yeasts into/onto cellulose-based fibers according to the invention or cellulosic fibers, respectively, which had been subsequently dried and then separated by grinding to individual cellulose-based fiber or cellulosic fibers, efficacy of fermentation was much greater after stirring the cellulose-based fibers in a sugar solution than was the case for cellulosic fibers. It has also been shown that, for example, anaerobic fermentations by microorganisms are much more rapid and effective when these microorganisms are incorporated/adhered into/onto the cellulose-based fibers and are added in this form to a fermentation mixture.

Preference is given to a process for the incorporation/adhesion of microorganisms onto/into cellulose-based fibers, to increase product output and/or fermentation performance. Preference is given to cellulose-based fibers for the incorporation/adhesion of microorganisms to increase product output and/or fermentation performance.

In one embodiment, the cellulose-based fibers are used for stabilization/storage/preservation of compounds/substances/organisms. In principle, all cellulose-based fibers produced according to the invention can be used for this purpose. Cellulose-based fibers of soy, rapeseed, corn or squash are preferred. For the incorporation/adhesion of compounds/substances/organisms cellulose-based fibers are preferred which have a residual moisture content of between 20 and 80% by weight. Preferably, the incorporation/adhesion is accomplished by suspending the cellulose-based fibers in a solution in which the compounds/substances/organisms to be incorporated/adhered are dissolved or suspended. The preferred exposure time is between 10 seconds to 24 hours, more preferably between 1 minute and 12 hours, and more preferably between 2 minutes and 6 hours, in which the cellulose-based fibers are present in the solutions/suspensions with the herein containing compounds/substituents/organisms. Preference is given to a slight agitation of the suspension with an agitator during the exposure time. Preference is given to a temperature between 5° and 90° C., more preferably between 15° and 75° C. and more preferably between 25° and 50° C. In a further preferred embodiment, cellulose-based fibers having a residual moisture content of <20% by weight are added to a solution/suspension with compounds/substances/organisms and hydrated therein, which leads to an incorporation/adhesion of the compounds/substances/organisms into/onto the cellulose-based fibers. In a further preferred embodiment, cellulose-based fibers which have a residual moisture content of >25% by weight are added to the compounds/substances/organisms which are present in dry or partially dried or agglomerated form and mixed, resulting in the cellulose-based fibers with incorporated/adhered compounds/substances/organisms. Preference is given to mixing by means of a stirrer or kneading stirrer. Preference is given to the incorporation/adhesion of organic compounds into/onto the cellulose-based fibers, with particular preference being given, for example, to vitamins, enzymes, antioxidants, furthermore microorganisms, such as, for example, yeasts, lactic acid-producing bacterial strains or algae. In a particularly preferred embodiment, cellulose-based fibers are used for the cultivation of microorganisms. It has been found that the proliferation and/or product output of yeasts and algae as well as bacterial strains can be markedly improved by adhesion to/incorporation into cellulose-based fibers compared to cultivation on/in culture media from the prior art.

For example, it has been shown that algae that have been incorporated into cellulose-based fibers produced a greater yield of triglycerides per unit volume than algae grown in a free liquid culture or attached to cellulosic fibers. Further, bakers' yeasts adhered/incorporated onto/into cellulose-based fibers could be shown to have a higher rate of reproduction than yeasts cultured in a fiber-free medium or yeasts attached to cellulosic fibers. The same was true for the metabolism of carbohydrates and the production of $CO_2$.

Preference is given to cellulose-based fibers for the cultivation of microorganisms/algae. Preference is given to cellulose-based fibers for improving the proliferation and production efficiency of microorganisms/algae which are adhered/incorporated onto/into the cellulose-based fibers.

Virtually all cellulose-based fibers according to the invention can be used as dietary fiber for human or animal nutrition. It may be a substitute for other dietary fiber and/or dietary fiber supplements of foods and food preparations or a diet. The cellulose-based fibers can in principle be consumed in any desired amount and added/admixed to food preparations. Preference is given to a consumption of inventively obtainable cellulose-based fibers of 0.01 g to 500 g (dry mass)/day, more preferably from 0.1 g to 250 g (dry mass)/day, more preferably from 1 g to 150 g (dry mass)/day and more preferably from 5 to 80 g (dry mass)/day. The cellulose-based fibers according to the invention can be consumed in any shape and consistency as a dietary fiber substitute or supplement. Preference is given to preparations with hydrogenated forms of the cellulose-based fibers, e.g. in liquid formulations, such as beverages, soups or sauces; or in solid formulations such as meatballs, dumplings or casseroles; or low-water formulations, such as pies or baked goods; or in dry formulations, such as chips or pastries. In principle, the cellulose-based fibers according to the invention can be added/admixed to all foods and all foodstuffs or processed or prepared with them. The amount that can be added to a food is not limited and depends on the formability of the individual preparation. Preferred is a preparation of the cellulose-based fibers according to the invention as dietary fiber and/or dietary fiber-enriched food preparation, which is prepared by a mixture of cellulose-based fibers with aroma/flavoring agents and/or carbohydrates and/or proteins and/or oils/fats/lipids and/or antioxidants/vitamins and/or colorants and/or other dietary fiber/roughage/stabilizers and preservatives. The mixtures can be made with dry starting components and/or with starting components which are wet and/or hydrated in an aqueous or lipid phase. In this case, any mixing equipment can be used and any temperature and any mixing or standing period can be selected. The preparation result may be prepared in directly obtained and raw form, in raw stored form, in cooked or fried or baked form, in a liquid to dry state. Thus, for example, ready-mixed mixtures can be produced with the cellulose-based fibers according to the invention by homogeneously admixing to a cellulose-based fiber mass, for example from kidney beans, seasoning mixtures from the prior art or adding a liquid seasoning to a dried and pulverized cellulose-based fiber mass until a homogeneous distribution has achieved and the mixtures are then offered for consumption in moist or dried form. In another embodiment, wet or dried cellulose-based fibers are mixed with proteins. The proteins may be of plant or animal or microbial origin and may be in dry or moist/hydrated form. Preference is given to a preparation in which dried and pulverized cellulose-based fibers prepared in accordance with the invention are mixed with a suspension of proteins until the free liquid has been consumed. Preferably, the resulting mass is subjected to belt drying and comminuted to a powder.

In another embodiment, cellulose-based fibers prepared according to the invention are used for the regulation of intestinal transit and/or stool consistency. In principle, all cellulose-based fibers according to the invention are applicable for this purpose. Furthermore, the aforementioned preparations can also be used for a regulation of intestinal transit and stool consistency. Preference is given to so-called instant formulations which can be solvated in a liquid medium and consumed in solvated form. So-called instant forms are, for example, powders or granules. Preferably, these are prepared with flavor/seasoning/sweeteners and/or stabilizers or soluble carbohydrates, by methods known in the art. In a preferred embodiment, the application of the cellulose-based fibers takes place in the form of a tablet or a capsule. It has been found that the cellulose-based fibers of the invention are particularly well suited for this purpose, since they can be brought into a very compact form. It has been found during a drying process of a moist mass of cellulose-based fibers that there is spontaneous formation of a condensation around a center of mass, so that a homogeneous continuous dry matter is formed.

As a result, the cellulose-based fibers can be condensed to very compact volume without relevant technical effort. It is advantageous that such condensed cellulose-based fibers, which have no hornification, can be hydrated only slowly and thus advantageously are completely hydrated and dispersed during the gastrointestinal passage only in the small and/or large intestine. As a result, in contrast to cellulose preparations from the prior art, an abdominal fullness feeling be avoided. The daily supply of cellulose-based fibers according to the invention for this application is preferably 1 to 50 g (dry weight)/day, more preferably 2 to 25 g (dry weight)/day and more preferably 3 to 15 g (dry weight)/day. In one embodiment, cellulose-based fibers are used as a dietary fiber additive or dietary fiber substitute. In one embodiment, cellulose-based fibers are used as regulators to effect an acceleration of the gastrointestinal passage and/or a softening of the stool. In one embodiment, cellulose-based fibers are used to treat constipation.

Surprisingly, it has been found that weight loss can be achieved by consuming cellulose-based fibers produced according to the invention even without a conscious change in the dietary habits. For this purpose, according to the invention manufactured cellulose-based fibers may be added to a regular diet, incorporated in them or are consumed with this, jointly or separately in a moist, of partially dried or dry form and over any period of time. In this case, applications in the form of capsules or tablets are possible. Preferred is the admixture of cellulose-based fibers produced according to the invention to the different food preparations. Preferred is a daily consumption of >5 g, more preferably of >10 g, more preferably of >15 g, more preferably of >20 g, more preferably of >25 g and particularly preferably of >30 g (figures as dry matter/dry weight). In addition, however, the cellulose-based fibers produced according to the invention can also be used specifically for weight-loss therapy. Preference is given to edible preparations in which the cellulose-based fibers and proteins produced according to the invention are used together or separately and in particular without the addition of fats or oils or are provided/prepared as foods. Preferably, the oral intake takes place at 2 or 3 times of the day. Preferably, for the purpose of weight reduction therapy >15 g/day, more preferably >30 g/day, more preferably >35 g/day, more preferably >40 g/day orally, more preferably 50 g/day (figures as dry matter) is consumed. Again, applications in the form of capsules or tablets are possible. The duration of the application is not limited and depends on the achieved and desired amount of weight reduction.

Preference is given to cellulose-based fibers for the treatment of constipation.

Preference is given to cellulose-based fibers for use as dietary fiber.

Preferable are cellulose-based fibers for use as a body weight-reducing dietary supplement. Cellulose-based fibers are preferred for regulating bowel activity and/or stool consistency.

Cellulose-Based Fibers

Most of the crops that are or may be grown for human or animal nutrition, and biomass that can be produced or are produced, are not used for food purposes because the products are considered to be non- or only partially edible. These include e.g. press residues of seeds and kernels, which remain after extraction of oils and fats. Another example is the trunk, e.g. of cabbage, and vegetables without special aromatic qualities, such as squash or celery. Furthermore, a large amount of fruits and vegetables is destroyed annually because of qualitative defects and/or insufficient freshness. Furthermore, most of the fruit and vegetable hulls and shells are not consumed and disposed of. Furthermore, biogenic starting materials, which are used as the starting materials for food preparations, e.g. for the production of wine, beer, or other alcoholic beverages or juices, are disposed of after their extraction. Surprisingly, it has been found that with the method according to the invention, all of these plant-based products can be used in a manner that is useful and beneficial for human nutrition. However, this is made possible only by the extremely advantageous effects of the method according to the invention. It has thus been possible to show that the use of the amino acid and/or peptide solutions according to the invention makes it possible to obtain and produce the cellulose-based fibers according to the invention. As a result, cellulose-based fibers can be obtained which have the same physico-chemical properties as were present in the organic context in which they were formed. These are in particular characterized by a very high water binding capacity, which is more than 20 times of its own weight as a common feature. They are also characterized by their particularly high water retention capacity and their colloidal properties. Thus, an increase in viscosity in an aqueous medium is achieved in a very reproducible and rapid manner, with a minimum sedimentation/settling rate of the hydrated cellulose-based fibers.

This is in particular due to the three-dimensional structure with a low specific weight. As a result, the cellulose-based fibers produced according to the invention achieve very good colloidal properties which can be used in a wide variety of areas. Thus, it was found that when used in soups and sauces in a weight range of 3-15 wt % (dry mass), without adding other thickening agents, a creamy to firm consistency could be achieved. The preparations exhibited a pleasant mouthfeel, even in the case of a high concentration of the cellulose-based fibers produced according to the invention, in the absence of a "sliminess" or a "mealiness", which was present when such a thickening effect with, for example, a cellulose derivative or a starch had been made.

Surprisingly, it has been found that the cellulose-based fibers obtained according to the invention can be functionalized with cellulose derivatives, preferably in process step c3) or d3). It has been shown that even small amounts of solvated cellulose derivatives are sufficient to cause an increase in the colloidal properties of the cellulose-based fibers produced. It could thus be shown that when a 1% by weight solution of methylcellulose, which had been mixed in a 10% by weight ratio with obtained cellulose-based fibers, and after a mechanical dewatering of the fiber mass had been carried out and the fiber mass had been dried and comminuted, solubility of those cellulose-based fibers when solvated in water was faster and resulted in a much more homogeneous consistency of soups and sauces compared to cellulose-based fibers which have been prepared without this functionalization. In principle, the same results were found when, instead of a cellulose derivative, a starch preparation was used.

Preference is therefore also given to a process in which, in process step c3) or d3), a functionalization with a cellulose derivative and/or a starch is carried out.

Thus, the invention also relates to processes for the functionalization of cellulose-based fibers. Furthermore, the invention also relates to functionalized cellulose-based fibers.

The cellulose-based fibers produced according to the invention have a very good emulsifying power in W/O or O/W mixtures, very probably by exposed hydrophobic cellulose structures. Another peculiarity with which the cellulose-based fibers produced according to the invention differ very markedly from cellulose fibers which originate from a grinding process of husks or stalks is their ability to stabilize the structure of food preparations, for example baked goods in baking processes. Two components that are very likely to occur in parallel, among others, can be assumed to be causative: 1. a skeletal function through the formation of multilocular contacts with other compounds of baked goods, such as proteins or carbohydrates, through the versatile side groups and the large-volume three-dimensional structures of the cellulose-based fibers and 2. the formation of gases, e.g. of water vapor, within these three-dimensional structures as well as their bonds/adherence thereto/herein. However, these properties are only obtained by the cellulose-based fibers if they have been obtained or prepared by one of the processes according to the invention, as could be shown in baking experiments.

Furthermore, it has been shown that only with the cellulose-based fibers according to the invention it is possible to incorporate and/or complex with microorganisms or chemical leavening agents which cause gas formation during a baking process, thereby providing an equal or significantly better baking result compared to the state of the art. In the case of cellulose-based fibers which have not been produced by one of the processes according to the invention, significantly worse results have been obtained than is possible according to the prior art (with the use of a wheat flour).

Thus, the cellulose-based fibers obtained and/or produced by the processes according to the invention differ considerably in their morphology, chemical constituents, physicochemical properties and the effects which can be achieved therewith in various applications compared to cellulose fibers which have been produced from stalk or husk materials, but also to cellulose derivatives, such as cellulose ethers. To preserve the extremely advantageous physical and sensory properties of the cellulose-based fibers, it is necessary that they are made obtainable in the form in which they fulfill/have fulfilled their physiological tasks. Surprisingly, it was found in comparative baking experiments that it is possible to partially or completely replace flour with cellulose-based fibers according to the invention, among others, in flour preparations of bakery products, such as bread rolls, bread, cakes and in flour products, such as pasta (e.g. noodles), crumble, sauces, without loss of volume increase, consistency and taste. A replacement of flour in food preparations is preferably carried out to >10% by weight, more preferably of >25% by weight, more preferably of >50% by weight, more preferably of >75% by weight, even more preferably of >90% by weight and most preferably of 100% by weight %. The cellulose-based fibers can be used in any form or consistency as a flour substitute. Preference is given to the use of dried cellulose-based fibers produced according to the invention having a residual moisture content of preferably <30% by weight, more preferably <20% by weight and more preferably of <10% by weight. Preference is given to the use of powdered cellulose-based fibers. Such cellulose-based fibers may preferably have been surface modified by any of the methods described herein.

Preference is given to the use of cellulose-based fibers which have been subjected to a hydrophilic or hydrophobic surface modification.

In another embodiment, cellulose-based fibers produced according to the invention were used as a flour substitute which have a residual moisture content of preferably 30 to 300% by weight, more preferably 40 to 200% by weight and more preferably 50 to 100% by weight. Such stirrable or spreadable cellulose-based fiber masses can be used in particular for the production of doughs, whereby the time for a swelling, as is the case with a flour, can be eliminated. Thus, it was possible to show that, for example, that a bread roll or a pizza dough could be produced with cellulose-based fibers according to the invention, wherein a replacement of the otherwise used flour content amounts to 80% by weight or 100% replacement. Both bakery products had a qualitatively comparable results compared to the original recipe, but in the tasting a better rating was found for the preparation with the cellulose-based fibers.

Preference is given to cellulose-based fibers for reducing and/or replacing flour/starch for food production.

Surprisingly, it has been possible to show that the use of cellulose-based fibers according to the invention also makes it possible to completely or partially replace oils and fats in the preparation of foodstuffs. It could be shown that the properties of oils and fats, which lead to characteristic physical and sensory effects in a food preparation, can also be obtained by the use of cellulose-based fibers produced according to the invention. So among others, it could be shown that a 90% by weight substitution of butter in the production of sweet crumbles or a 90% by weight substitution in the production of a butter cream did not lead to any affect the sensory characteristics compared to the original recipe. The taste experience was judged by experts as creamy, rounded and balanced, with a pleasant mouthfeel. It could be shown that even the complete replacement of fats or oils is possible without a loss of product quality. Preferably, the replacement of oils or fats by cellulose-based fibers produced according to the invention, in a food or food preparation, is >5% by weight, more preferably >10% by weight, more preferably >20% by weight, more preferably >30% By weight, more preferably >40% by weight, more preferably >50% by weight, preferably >60% by weight, more preferably >70% by weight, more preferably >80% by weight, more preferably >90% by weight, more preferably 100% by weight.

Preference is given to cellulose-based fibers which have undergone surface conditioning and/or surface functionalization.

Preference is given to the use of partially dry, dried or moist cellulose-based fibers according to the invention. Further preferred are partially dried cellulose-based fibers having a residual moisture of 15 to 80% by weight, more preferably from 20 to 60% by weight. When used as a partial substitute for oils or fats, the cellulose-based fibers, along with the oils or fats or separately therefrom, may be blended into the food or food preparation. The mixing ratios and mixing time required for the desired product specification must be determined individually.

Preferred are cellulose-based fibers for use as oil/fat substitutes.

It has been found that it is extremely advantageously possible to emulsify/stabilize oils and fats with the cellulose-based fibers according to the invention, so that they obtain a consistency which enables immediate application. In the prior art, oils or fats having a low melting point and/or low viscosity are subjected to thermal and/or chemical processes to increase the melting point/viscosity of the oils or fats. This can result in formation of products harmful to health. Alternatively, emulsifiers and/or stabilizers are added to the oils or fats, which also have harmful potential for health or lead to taste impairment. It has been found that the cellulose-based fibers according to the invention can be mixed with oils and fats in virtually any desired mixing ratio, forming stable mixtures having an increased viscosity and melting point. In principle, dry and powdered, partially dried or moist cellulose-based fibers can be used. Preference is given to the use of partly dried or moist cellulose-based fibers. Particularly preferred is a residual moisture content between 10 and 100% by weight, more preferably between 15 and 70% by weight and more preferably between 20 and 50% by weight. Preference is given to the use of cellulose-based fibers in which surface modification and/or surface functionalization and/or adhesion to the surface, for example with antioxidants or vitamins, has been carried out. Preference is given to intensive mixing of the cellulose-based fibers of the invention in an oil or fat; of particular preference is the use of homogenizers or high-performance shear mixers based for example on the rotor-stator principle. Preferred is a mixing time between 1 second and 3 hours, more preferably between 10 seconds and 1 hour and more preferably between 30 seconds and 10 minutes. The qualitative mixing result can be determined by methods from the prior art for determining the viscosity or the melting point. Preferred is an increase in the melting point between 0.2° and 30° C., more preferably between 0.5° and 20° C. and further preferably between 0.8° and 10° C. Preference is given to an increase in the viscosity between 0.1 and 500 cSt, more preferably between 0.5 and 300 cSt and more preferably between 1 and 200 cSt. Preference is given to the preparation of a highly viscous or solid mass with a homogeneous texture. Preferred is a consistency that is spreadable. It could thus be shown that the homogenization of milk fat and of rapeseed oil with cellulose-based fibers produced according to the invention, which were obtained from rapeseed or soy press cake, resulted in a butter with a melting point at 38° C. and a margarine with a melting point of 28° C., respectively, with an addition amount of cellulose-based fibers of 8 and 5% by weight. In a preferred embodiment, cellulose-based fibers produced according to the invention are mixed with oils or fats in order to produce a butter or margarine therefrom. The preparation of a readily spreadable preparation is preferred.

Preference is given to cellulose-based fibers for the preparation/formulation of butter and/or margarine.

Surprisingly, it has been found that the cellulose-based fibers produced are outstandingly suitable for formulating dissolved or soluble proteins. When drying proteins that are present in an aqueous solution, a hard mass is formed, which can only be crushed with high energy expenditure and incompletely. A comminution is necessary because the proteins in the dried state, which were very readily soluble before drying, are very difficult to solubilize/hydrate again. Therefore, fine grinding is necessary. In order to achieve a very fine particle size and to obtain an improved solubility compared to a finely ground protein preparation, according to the state of the art, the soluble or dissolved proteins are processed into granules or powders with a high expenditure/input of energy. Particularly suitable for this purpose is spray-drying, as a result of which easily soluble protein powders can be prepared. It was now possible to show that, in particular, dried and powdered cellulose-based fibers are very well suited for taking up the binding water of the dissolved or soluble proteins and thereby accumulating/incorporating proteins onto/into the cellulose-based fibers. Surprisingly, mixtures can be prepared thereby, which make it possible to formulate the dissolved or soluble proteins into readily water-soluble agglomerates or powders. In one embodiment, a suspension of aggregated proteins having a water content of from 10% to 300% by weight, more preferably from 20% to 200% by weight and more preferably from 30% to 100% by weight, is mixed with powdered cellulose-based fibers having a preferred mean size of the powder particles between 1 μm and 500 μm, more preferably between 5 and 200 μm, and more preferably between 10 and 100 μm, preferred is mixing with an agitator.

The mixture can in principle be carried out in any mixing ratio, preference is given to adding the liquid phase until a water content of between 20% and 120% by weight, more preferably between 25% and 90% by weight, more preferably between 28% and 60% by weight and more preferably between 30% and 50% by weight is achieved. The mixture should preferably be carried out until complete hydration of the cellulose-based fibers has been achieved. As a result, a dough-like mass is obtained, which is very easy to process and in particular does not tend to stick or be sticky, as is the case with the pure protein fraction. This also makes it possible to carry out drying processes which are unsuitable for drying the sole protein fraction, since this gives no or only slightly soluble protein agglomerates. Preferred is the drying of the mixture of proteins and cellulose-based fibers by applying on a belt-drying apparatus. The drying can then be carried out in a temperature range between 40° and 200° C., more preferably between 50° and 150° C. and more preferably between 60° and 120° C. Preference is given to a simultaneous use of vacuum equipment. The mixture may be comminuted or kept in motion during the drying process. This has the advantage that a granulate or powder is already present after drying. Alternatively, a grinding of the condensates/agglomerates can be carried out after the drying process. Surprisingly, a powder is obtainable from the dried mass that is very readily soluble in water, with complete hydration of the proteins contained therein. Preference is given to obtaining a protein powder which has a proportion of cellulose-based fibers produced according to the invention of between 1% and 95% by weight, more preferably between 10% and 80% by weight, more preferably between 15% and 70% by weight and more preferably between 20% and 50% by weight. The mean particle size of the powder is between 1 μm and 500 μm, more preferably between 5 μm and 300 μm and more preferably between 10 μm and 200 Linn. The obtainable mixtures are also characterized by an odor and/or taste neutrality, as a result of the adsorption of odorants and flavoring agents by the cellulose-based fibers produced according to the invention. The mixtures of proteins and cellulose-based fibers produced according to the invention are distinguished by their very good solubility, which corresponds to a formulation of the protein by spray-drying. Complete dissolution of the proteins from the mixture of proteins and cellulose-based fibers comprises 50% to 150% of the time that is required for the complete dissolution of the spray-dried proteins, more preferably within 70% and 130%, and more preferably within 80 and 120% of that time.

In principle, cellulose-based fibers can be obtained by the processes according to the invention which serves as suitable formulation matrix for all soluble or dissolved proteins. Preference is given to dissolved proteins from seeds of, in particular, rape, sunflowers, camelina, jatropha; in addition, from the unlocking of kernels, such as soya or beans, and also from nuts, such as almonds or hazelnuts; also grains such as wheat or oats; also made from lentils and peas or lupins. In principle, however, any other protein fraction can also be formulated by the cellulose-based fibers according to the invention. Especially suitable is milk protein. In a further preferred mode of application, protein from fish or marine animals are formulated with the cellulose-based fibers by one of the methods described herein. This has the enormous advantage in that it comes to a significantly lower expression of a fishy odor. In many formulations, in contrast to the dried protein mass, there was practically no more fishy odor perceptible. In another embodiment, proteins from microorganisms, such as algae or yeast, are bound to and/or agglomerated with the cellulose-based fibers. In one embodiment, the proteins which are formulated by one of the processes with the cellulose-based fibers according to the invention are prepared, for example, by swelling a disintegrated seed of rapeseed with an unlocking solution. Preferably, cationic amino acids and especially arginine are present in the unlocking solution. Following a reaction phase, a dispensing of the unlocked constituents of the plant material in a water phase is carried out, in which the proteins are then present almost completely in dissolved form. After separation of the remaining suspended constituents, which is preferably done with a sieve, an aqueous solution is obtained in which all readily water-soluble constituents of the starting material are present in dissolved form. By aggregating the proteins, which can be carried out for example by a change of the pH of the solution and/or a change in salinity and/or use of complexing agents, there is condensation of the dissolved proteins, which sediment in aggregates and can be condensed and separated with processes from the prior art. Preference is given to the use of such obtained and aggregated protein mixtures for formulation with the cellulose-based fibers produced according to the invention. Very particular preference is given to the use of cellulose-based fibers which have the same origin as the proteins formulated herewith. This is extremely advantageous, as it can produce of single-origin educts from proteins and cellulose-based fibers of an identical starting material that are completely or almost completely free of odorants and flavoring agents or leachable colorants and essentially do not contain undesirable compounds, such as insecticides, pesticides, fungicides or toxins.

Furthermore, with this method, excellent transportability and storability of the protein fractions can be achieved. Furthermore, it could be shown that storage stability (shelf life) was very good. Thus, even after 8 months, there was no qualitative change in the mixtures of proteins and cellulose-based fibers. In another preferred type of the process, the cellulose-based fibers according to the invention are used as crystallization nuclei of soluble or dissolved proteins. For this purpose, preferably partly dried or dry and powdered cellulose-based fibers are used by for example filling these in a rapidly rotating drum having a stripping device and the protein suspension is applied to the cellulose-based fibers by means of a spray device. Preferably, warm air flows through the drum. The process is finished when the resulting aggregates/granules have the desired dimensions. This method offers the advantage that a larger mass ratio can be produced between the attached/incorporated/deposited proteins and the cellulose-based fibers. Preferred is a mass ratio between protein and the cellulose-based fibers between 2:1 to 1000:1, more preferably between 10:1 to 500:1, and even more preferred between 20:1 to 300:1, of the agglomerates/condensates obtained by one of the methods.

Preference is given to cellulose-based fibers for the formulation of dissolved or soluble proteins.

Preference is given to condensates/agglomerates of proteins and cellulose-based fibers for improving the transportability and/or shelf life of proteins.

Preference is given to the production of condensates/agglomerates of soluble proteins with cellulose-based fibers.

Preference is given to condensates/agglomerates of cellulose-based fibers and proteins.

Sensory Effects of the Cellulose-Based Fibers

The cellulose-based fibers produced according to the invention are distinguished by particular sensory effects which differ considerably from those of the cellulose fibers which are recovered from husks and stalks, and from those of the cellulose ethers. The dimensions of the cellulose-based fibers according to the invention are distributed over a wide range between 10 μm and >1,000 μm and the median of the widest diameter dimension was between 100 μm and 500 μm. From studies on the perceptibility of corpuscular solids through the oral mucosa, it is known that particles with a diameter of more than 15 microns are already perceived as a solid.

From studies with cellulose fibers of different origin and fiber lengths, that were added to food preparations in increasing amounts, it could be shown that even cellulose fibers with a fiber length of <30 μm were perceived in the form of a dull taste sensation when exceeding a concentration of 0.5 wt %. At a concentration of >1% by weight, this sensation was found to be disturbing. With increasing fiber length of the cellulose fibers/cellulose ethers, the perceived disturbing sensations were present even at lower added levels. Cellulose ethers cause a slimy mouthfeel at a weight proportion of >1%, solutions with a weight percentage of >5% are generally solid gels which cause unwanted effects in preparations and are not edible. Unexpectedly, none of the investigated cellulose-based fibers produced according to the invention lead to such a perception, although they all had significantly larger dimensions than the cellulose fibers/cellulose ethers investigated. This was also the case when using large proportions by weight of the cellulose-based fibers according to the invention. Both, the moist and the dried cellulose-based fiber masses, when consumed alone, do not result in a dry, dull, hard, sticky or slimy mouthfeel, which was the case when cellulose fibers/cellulose ethers were consumed instead. Even with a high mass fraction (>15% by weight) and a moisture content of 80-100 wt %, the cellulose-based fibers according to the invention are in a past-like and spreadable form; solid gels are not formed. Accordingly, the sensory impressions perceived upon consumption of cellulose-based fibers produced in accordance with the present invention have been reported as soft or tender, silky, melting, fat-like, full and pleasing by the testers. The sense impression "soft" was associated with the absence of the feeling of corpuscular materials that is noticeable with the tongue or when chewing. An improvement in sensory effects could also be achieved with the use of the cellulose-based fibers of the invention in soups and sauces and milk dishes or water-based preparations, such as jams or jellies. Especially jellies were more spreadable and/or dissolved better in the mouth. Also fruit pulp became more homogeneous in consistency and full in taste, while potentially pronounced acidic components were suppressed largely sensory. Surprising was also the perceptible mediation of a fatty feeling. This has been demonstrated, for example, in savory sauce preparations, which are usually made with added fat, such as a coconut milk-based curry sauce or a hollandaise sauce. The replacement of the respective fat content by cellulose-based fibers led to a similar full-bodied, rounded, emulsifying and soft mouthfeel, as in the case of a preparation with a coconut milk or butter, while the use of cellulosic fibers from husks and stems or cellulose ethers, on the one hand, led to an adequate consistency of the sauces and on the other hand, caused an unbalanced to unpleasant mouthfeel and dull taste, or the preparation was not edible.

A better result in terms of consistency and taste sensation was also found, for example, in the production of ice cream with cellulose-based fibers. In the case of water-based ice cream preparations in particular, the taste result with the addition of cellulose-based fibers was more harmonious than when the original recipe was used. In addition, surprisingly, there has been an improved sensory perception in foods that are generally made with high proportions of oils or fats. For example, replacement of 50% by volume of the amount of oil/fat used in the original formulation by cellulose-based fibers, which had a residual moisture content of 70% by weight, resulted in a similarly pleasing, soft or melting mouthfeel of buttercream or mousse-o-chocolate, as in preparations with the added fat according to the original recipe. At the same time, the "heaviness" and "fattening sensation" caused by the large amount of fat in the preparations according to the original recipe were not present due to the use of cellulose-based fibers.

Preference is given to cellulose-based fibers which mediate/give a sensorially soft and/or fat-like sensory impression.

Preference is given to cellulose-based fibers as oil/fat substitutes in food preparations. Surprisingly, it was then found that cellulose-based fibers produced according to the invention do not encrust in a baking, roasting, or frying process with temperatures of more than 100° C. and/or have no or practically no signs of charring. Roasting experiments showed that cellulose-based fibers with a residual moisture content of 20% by weight, which were fried in a frying fat at 240° C., condensed to small golden yellow grains after evaporation of the bound water, which did not changed in their color and appearance even after the frying process was continued for 15 minutes. The mass was then in the form of loosely assembled granules with diameters between 0.2 to 1.5 mm, which were easily chewable in the mouth and could quickly no longer be perceived as particles in the mouth. In further experiments, a thickened mashed potato mass was formed into flat slices and coated with an approximately 1 mm thick layer of breadcrumbs, cellulosic fibers from stalks or husks and the cellulose-based fibers of soybeans and camelina produced according to the invention all of which were adhered on the surfaces by lightly "pressing". They were cooked by roasting, baking, grilling and frying. The respective studies were carried out for period of time which led to a significant charring of the breadcrumbs (dark brown discoloration and hardening).

It was found that when the foods were coated using cellulose-based fibers, there was no brownish or brown or black discoloration and thus no charring, whereas this was the case with the breadcrumb-coated foodstuffs. For coatings with cellulose preparations, there was only slight dark discoloration, but the coatings largely became detached during the cooking process. While the products prepared with breadcrumbs had a hard outer layer and tasted burnt, the cooking products coated with cellulose-based fibers according to the invention were crispy but not hard and could easily be chewed during the chewing process with a pleasant mouthfeel and without compromising the taste of the food. In repeated experiments it was shown that a coating of a food (including meat, tofu, fish, flour doughs) with dried and powdered cellulose-based fibers according to the invention allows a similar good cooking behavior and neutral taste without a dark discoloration or sensory change of the food. In a preferred application, cellulose-based fibers produced in accordance with the invention are used as release agents for roasted, baked, grilled or fried goods, in order to avoid browning, dehydration or other thermal damage to the baked goods. It has also been found that, in particular when using cellulose-based fibers which have a residual moisture content of more than 10% by weight, the food-preparation undergoes a lower degree of water-loss during the cooking process. Preference is given to the use of a moist and advantageously spreadable form, a preparation as a spreadable paste, e.g. in a formulation with an oil or marinade or preferably as semolina or in powdered form. But other preparations are possible also.

Preference is given to cellulose-based fibers as a release agent for cooked products, intended for a roasting, baking, grilling or frying process.

Following a tasting of the cellulose-based fibers according to the invention, the examiners found a long-lasting fruity taste. This could be reproduced in repeated investigations and was the case in particular after the tasting of cellulose-based fibers of pumpkins made according to the invention. Furthermore, the participants of tasting experiments surprisingly reported that, following the tasting of cellulose-based fibers produced according to the invention, there is a greater flow of saliva and bad breath no longer occurred. In a comparative study with cellulosic fibers from husks and stems as well as with cellulose ethers, it was found that, in contrast to the consumption of cellulose fibers or cellulose ethers, after consumption of more than 0.5 g (dry mass) of the cellulose-based fibers the sensation of increased saliva production was noticed. Furthermore, there was practically no development of unpleasant halitosis after consumption of the cellulose-based fibers, when the teeth were not cleaned for 24 hours, while after consumption of cellulose fibers, cellulose ethers or another diet, the majority of subjects reported unpleasant halitosis development during this period.

Preference is given to cellulose-based fibers for stimulating the salivation flow.

Preference is given to cellulose-based fibers for the reduction of unpleasant halitosis.

Surprisingly, it has then been found that cellulose-based fibers cause very particularly advantageous effects in the formulation and application of solutions, gels, lotions or creams applied to the skin and mucous membranes. For example, oils or fats required when formulating ingredients could be reduced or eliminated altogether. The obtained solutions, gels, lotions or creams were stable even after 6 months, i.e., that, for example, no segregation of ingredients occurred. Furthermore, the practical application showed that solutions, gels, lotions or creams were very easily rubbed into the skin and mucous membranes with a good spreadability, which was better than the original formulation. The sensory perception while rubbing in the solutions, gels, lotions or creams on the skin and mucous membranes was perceived as soft and pleasant by all study participants. Following application to skin or mucous membranes with a proportion of >0.1% by weight of cellulose-based fibers produced according to the invention, there was a perceptible and measurable increase in surface moisture, which decreased only slightly over the period of >6 hours. When the same study was carried out with preparations prepared with cellulosic fibers from husks or stems or cellulose ethers, there was some separation during storage, unpleasant sensations when spreading/rubbing in on skin and mucous membranes and there was only a minimal increase in the surface moisture of treated skin or mucous membrane areas.

Preference is given to cellulose-based fibers for the formulation of solutions, gels, lotions or creams for use on the skin and/or mucous membranes to reduce/replace oils and/or fats and/or increase the surface moisture of the skin and/or mucous membranes.

The object of the invention, the production of cellulose-based fibers, is accomplished by an aqueous process with which plant-based cellulose-based fibers can be obtained and produced in their natural form.

According to the invention, the obtainment and production of plant-based cellulose-based fibers by a process consisting of the steps
a) providing a non-lignified plant-based starting material containing cellulose-based fibers,
a1) disintegration of the plant-based starting material from step a) by a thermal and/or mechanical disintegration process,
b) impregnation of the disintegrated plant-based material from step a) or a1) with an aqueous unlocking solution,
c1) rinsing out soluble constituents of the plant-based starting material,
c3) adhering one or more functionalizing compound (s) and/or microorganisms onto the surfaces of the cellulose-based fibers
d1) removing bound water by a physical method
e) obtaining cellulose-based fibers which expand to three-dimensional structures on contact with water and release no or only minimal amounts of readily water-soluble carbohydrates and/or proteins and/or aromas and/or colorants in an aqueous suspension and/or release and/or take up inorganic and/or organic compounds and/or microorganisms. It is preferred that the aqueous unlocking solution contains dissolved amino acids and/or peptides.

Therefore, according to the invention, the obtainment and production of plant-based cellulose-based fibers by a method consisting of
a) providing a non-lignified plant-based starting material containing cellulose-based fibers,
a1) disintegration of the plant-based starting material from step a) by a thermal and/or mechanical disintegration process,
b) impregnation of the disintegrated plant-based material from step a) or a1) with an aqueous unlocking solution containing dissolved amino acids and/or peptides,
c1) rinsing out soluble constituents of the plant-based starting material,
c3) adhering one or more functionalizing compound (s) and/or microorganisms onto the surfaces of the cellulose-based fibers
d1) removing bound water by a physical method
e) obtaining cellulose-based fibers which expand to three-dimensional structures on contact with water and release no or only minimal amounts of readily water-soluble carbohydrates and/or proteins and/or aromas and/or colorants in an aqueous suspension and/or release and/or take up inorganic and/or organic compounds and/or microorganisms. Whereby the amino acids and the peptides in step b) are preferably cationic amino acids.

A further object of the invention, the use of cellulose-based fibers for the production of food and dietary supplements, is accomplished by an aqueous process with which plant-based cellulose-based fibers can be obtained and produced in their natural form.

According to the invention is the use of plant-based cellulose-based fibers for food preparation and/or as a food supplement, produced by a method consisting of
a) providing a non-lignified plant-based starting material containing cellulose-based fibers,
a1) disintegration of the plant-based starting material from step a) by a thermal and/or mechanical disintegration process,
b) impregnation of the disintegrated plant-based material from step a) or a1) with an aqueous unlocking solution,
c1) rinsing out soluble constituents of the plant-based starting material,
c3) adhering one or more functionalizing compound (s) and/or microorganisms onto the surfaces of the cellulose-based fibers
d1) removing bound water by a physical method
e) obtaining cellulose-based fibers which on contact with water expand to three-dimensional structures and release no or only minimal amounts of readily water-soluble carbohydrates and/or proteins and/or aromas and/or colorants in an aqueous suspension and/or release and/or take up inorganic and/or organic compounds and/or microorganisms. It is preferred that the aqueous unlocking solution contains dissolved amino acids and/or peptides.

It is preferred that the aqueous unlocking solution contains dissolved amino acids and/or peptides.

Therefore, the use of plant-based cellulose-based fibers is according to the invention, that are prepared by a method consisting of a) providing a non-lignified plant-based starting material containing cellulose-based fibers, a1) disintegration of the plant-based starting material from step a) by a thermal and/or mechanical disintegration process, b) impregnation of the disintegrated plant-based material from step a) or a1) with an aqueous unlocking solution containing dissolved amino acids and/or peptides, c1) rinsing out soluble constituents of the plant-based starting material, c3) adhering one or more functionalizing compound (s) and/or microorganisms onto the surfaces of the cellulose-based fibers d1) removing bound water by a physical method e) obtaining cellulose-based fibers which, when in contact with water, expand to three-dimensional structures and release no or only minimal amounts of readily water-soluble carbohydrates and/or proteins and/or aromatics and/or colorants in an aqueous suspension and/or release and/or take up inorganic and/or organic compounds and/or microorganisms.

Whereby the amino acids and the peptides in step b) are preferably cationic amino acids. Thus, a method and method variants can be provided with which functional decompacted cellulose-based fibers can be obtained and produced from a wide variety of plant-based starting materials. The method is particularly suitable for obtaining and producing functional cellulose-based fibers from non-lignified plant-based materials without need to use of a further process for digestion. In addition, the process according to the invention can also be applied to plant-based biomass, preferably to waste consisting of plant-based foodstuffs. Furthermore, cellulose-based fibers can be produced with the process according to the invention, which differ significantly from cellulose fibers as well as from cellulose ethers which derive from woody or lignified plant material, in particular because of their geometric structures and the physicochemical properties. This relates in particular to the functional properties of the cellulose-based fibers produced according to the invention, which leads to unexpected product properties when using the cellulose-based fibers.

In particular, a considerable improvement in the water-binding and retention capacity of products to which cellulose-based fibers produced according to the invention were admixed or used together with these could be shown. For example, foods that dry out easily, such as e.g. a fruit cake or cheese cake or baked products, such as bread or cake, are protected from drying-out much longer than with compounds of the prior art. Furthermore, mixtures, for example of aqueous and fat-based systems, can be formulated more easily and are more stable than is possible with cellulose fibers or cellulose ethers. In addition, compounds or substances or microorganisms can be absorbed/incorporated, transported and stored on and/or in the cellulose-based fibers produced according to the invention, whereby, for example, anti-oxidative or sunscreen compounds can be incorporated into dermatological preparations and stabilized herein. Furthermore, the cellulose-based fibers produced according to the invention enable the incorporation and/or adhesion of microorganisms and algae, resulting in further advantageous effects. Thus, for example, a significant increase in the proliferation and metabolic activity of microorganisms and algae can be achieved thereby, which, for example, can be significantly accelerate fermentation of milk to a yogurt or the formation of carbon dioxide for volume production in a baking preparation. In addition, microorganisms and algae can be cultivated, transported and stored by incorporation and/or adhesion into/onto the cellulose-based fibers produced according to the invention. Cellulose-based fibers produced according to the invention also cause extremely advantageous effects in the preparation of foods or foodstuff. For example, cellulose-based fibers produced according to the invention can be used as a substitute for both flour and starch, as well as for fats and oils, without there being any undesirable impairment of the sensory properties of the product. In addition, soluble or dissolved proteins can be formulated by the cellulose-based fibers produced according to the invention and processed much more easily than with processes from the prior art. Furthermore, by using cellulose-based fibers prepared according to the invention, weight loss can be achieved, as well as a regulation of bowel activity and stool consistency.

Definitions

Plant-Based Starting Materials

The term "plant-based starting material" as used herein includes all plant products containing cellulose. In principle, the plant-based starting materials may have any proportion of lignin and cellulose fibers, among other compounds. The preferred plant-based starting materials are non-woody/non-lignified plant-based materials characterized by a low level of lignin. In particular, the non-lignified plant-based materials referred to herein have a lignin content of <10% by weight. Such plant-based starting materials may be, for example, seeds, grains, kernels, beans, beet plants, vegetables, fruits, berries, cucumbers, blossoms and roots or tubers or nuts.

These may be in the form of unripe, ripening, ripened, overripe, aged or even damaged plant-based starting materials. Also suitable are contaminated or spoiled plant-based starting materials. The plant-based starting material may be in intact form, damaged, crushed, peeled, pressed, ground, or otherwise degraded, including but not limited to milled or ground flour, resulting, for example, from a mechanical extraction of oils, so-called press cake. These include plant-based starting materials which have previously undergone a thermal and/or liquid extraction process, e.g. with an alcohol or an organic solvent, such as hexane. Also included are plant-based starting materials in which a thermal treatment has taken place. These also include plant-based products that are obtainable from a digestion and/or fermentation process, in particular residues of those processes, such as brewery residues (e.g. in the form of spent grains or spent grain flour) or pomace in apple cider production or olive pomace or beet pulp, in particular after extraction of molasses. In addition, residues of cocoa beans are included.

Preference is also given to residues of press residues which are arise, for example, in the recovery of juices (for example apple, tomato or carrot juice) or pomace, e.g. of grapes or apples or extracts, as obtained in the production of jellies or liqueurs (e.g., blackberry jelly, cassis).

Further, products of plant-based starting materials derived from a peeling, dehulling or deseeding process may be used.

Under this definition fall in particular all plant seeds, such as linseed, poppy seeds, chia, amaranth, chili, tomatoes, anise, pea; Grains, e.g. of rapeseed, camelina, oats, hemp, wheat, buckwheat, rye, barley, maize, sunflowers, green spelt, jatropha; Fruit seeds/pits, e.g. from apples, pears, lemons, grapefruits, grapes, oranges, cherries, plums, apricots, peaches, whitty pear, medlars, mirabelle plums, rowanberries, pumpkins, melons, avocados; Legumes such as soybeans, field beans, mats beans, mung beans or kidney beans, peas, lentils such as e.g. Duckweed lenses, cocoa or coffee beans, lupines or sesame seeds; Vegetables such as cauliflower, broccoli, kohlrabi, zucchini, peppers, artichokes or okra; bulbous plants, such as carrots or sugar beet; Fruits, such as apples, pears, quince, bananas, breadfruit, mango, kiwi, *maracuja* fruit, melons, passion fruit, figs, pumpkin, pineapple, avocado, olives, mango, chayote, *guava*, papaya, tamarillo, *marmota* apple, grapefruit, oranges, lemons or grapes; Berries such as rose hips, gooseberries, blueberries, blackberries, strawberries, elderberries, currants, cranberries, mulberries, chokeberries, raspberries, blackberries, sandorn; tuberous plants and roots, such as potatoes, beetroot, *batata*, turmeric, cassava, horseradish, celery, radishes, ginger, arakascha, taro, wasabi, yacon, salsify, asparagus, parsnip, mustard, Jerusalem artichokes, cattail, swede, Siberian angelica, yam, yam root, sunflower root, devil's claw or ginko; as well as cucumbers, such as salad or pickled cucumbers, as well as eggplant or zucchini; Nuts, such as almonds, hazelnuts, peanuts, walnuts, cashew nuts, Brazil nuts, pecans, pistachios, chestnuts, sweet chestnuts, dates or coconuts. Furthermore, sugarcane.

Not meant are the lignin-rich shells of seeds, grains, fruits, vegetables or legumes. But also included are the stalk and root system; but not included are wax- and/or fiber-rich shells or foliage of these. Furthermore, the definition includes roots and ovaries, such as *ginseng* or beetroot; but not fibrous shells and ramifications. Also included are fruits such as apples, pears, quinces, plums, bananas; but not included are lignin-rich shells or husks of these. Also included are the blossoms of ornamental and crop plants.

Not included in the plant-based starting materials according to the definition are stems, branches, twigs or stems of trees, shrubs of useful plants.

The term "non-woody" refers to the above-defined starting materials in which a weight fraction of lignin polymer compounds of <15% by weight, preferably of <10% by weight and more preferably of <5% by weight and in particular of <0.5% by weight is present.

Cellulose-Based Fibers

The term "cellulose-based fibers" as used herein includes all of the solid structures of the plant-based starting materials consisting of a backbone of polymeric carbohydrate/cellulose structures having at least 2 of the following characteristics:
originates from a plant-based starting material,
an aspect ratio of a longitudinal and a transverse diameter of 1:1 to 1000:1
a water binding capacity of >200% by weight,
a proportion of chemical compounds and functional groups of >2.5% by weight that do not correspond to a polymerized carbohydrate.

The cellulose-based fibers according to the invention have three-dimensional spatial and surface structure. They can be present in a composite structure which can be divided into spherical or three-dimensional fragments by physical measures, such as mechanical comminution and/or thermal treatment. The cellulose-based fibers produced according to the invention are further distinguished by a very low weight per fiber length, the coarseness, which is preferably <70 mg/100 m, more preferably <50 mg/100 m, more preferably <30 mg/100 m and even more preferably <20 mg/100 m, more preferably <15 mg/100 m and most preferably <10 mg/100 m.

The cellulose-based fibers are water insoluble. The cellulose-based fibers produced according to the invention can be hydrated by water. The cellulose-based fibers according to the invention are not cellulose derivatives which have been prepared by a chemical process for polymer-analogous reaction.

In the original form, compacted cellulose-based fibers may exist in a disintegrated composite with other compounds or components, such as e.g. in a matrix that has been broken up and broken apart by pressing or crushing, such as in the case of pressed oilseed or ground grains or they are compacted in a stable composite structure, which prevents hydration/separation of the cellulose-based fibers, such as is the case in vegetables or fruits.

The cellulose-based fibers included in the definition are characterized by structural features and physical properties that are common to them. For example, they mainly consist of cellulose structures that are non-linear or form fiber bundles. In particular, they have spatial structures in the form of free fibers, nets (webs) or three-dimensional structures. The cellulose-based fibers according to the invention preferably have a planar and/or three-dimensional geometry. They may include or encapsulate pigments, or the pigments can be structural constituents of the cellulose-based fibers of the invention. However, other organic or inorganic compounds may also be constituents of the cellulose-based fibers or may be bound to them in that they are not detachable by an aqueous medium.

The cellulose-based fibers produced according to the invention are further characterized in that they have at least one of the following properties: three-dimensional structures through the uptake of water, a high water-binding and/or water retention capacity, an absence of readily water-soluble carbohydrates and proteins, and no transfer of flavoring or colorants into a water phase.

The cellulose-based fibers preferably consist of polymeric saccharide compounds containing functional side groups, such as SH—, OH—, NH— or COOH— groups, or are covalently linked to other compounds.

Cellulose-based fibers are, among others, functionalizable via physico-chemical interactions of the functional side groups with organic and inorganic compounds. Preference is given to cellulose-based fibers having a maximum diameter of from 10 µm to 2,000 µm, more preferably from 20 µm to 1,000 µm and more preferably from 30 µm to 500 µm. Preference is given to cellulose-based fibers having a minimum diameter between 0.5 µm and 50 µm, more preferably between 1 µm and 30 µm and more preferably between 3 µm and 20 µm. Preferably they exhibit uniform distribution of the average fiber diameter in a range between 5 µm and 500 µm, more preferably between 20 µm and 300 µm and more preferably between 40 µm and 200 µm. Preferably, cellulose-based fibers having an aspect ratio (maximum length and width) between 1:1 and 1000:1, more preferably between 1:1 and 500:1, more preferably between 1:1 and 250:1, even more preferably between 1:1 and 180:1 and more preferably between 1:1 and 100:1. Preference is given to complex 3-dimensional structures which are formed by the cellulose-based fibers.

The cellulose-based fibers have a content of readily water-soluble carbohydrates, proteins and flavoring or colorants, preferably of <3% by weight, more preferably of 2% by weight, more preferably of 1% by weight and even more preferably of 0.5% by weight.

The cellulose-based fibers produced according to the invention, which are obtained with the process steps d) or e), have these properties, which can be checked by methods of the prior art.

Disintegration/Unlocking

The term "disintegration" as used herein means all processes which lead to a separation of plant tissues or structures, whereby the structural components are completely wettable with one of the unlocking compounds which are present in an aqueous solution in the process of steps a) to d).

Thus, the definition includes all processes that result in the creation of cracks, voids or crevices of the starting material, up to achieving complete unlocking by exposure of the surfaces of the constituents of the plant-based starting material. It is crucial that the disintegration allows wetting of the surfaces of the constituents of the plant-based starting material with the compounds of the unlocking solution. Thus, by definition, disintegration is equivalent to the preparation of wettability of constituents of the non-woody plant-based starting material for the aqueous unlocking solutions and the compounds contained therein.

By the term "unlocking" herein is meant, the process of hydration, in which the aqueous unlocking solution is brought into contact with the constituents of the starting material, which cause that the soluble constituents can be completely separated from one another and from the non-soluble constituents (such as the cellulose-based fibers) in an aqueous phase. If in a process for disintegration also unlocking can be accomplished in the same process step, such for example, when using an aqueous solution containing unlocking compounds that are suitable for disintegration, the terms disintegration and unlocking can be used interchangeably. By hydration of the readily water-soluble compounds, the compacted cellulose-based fibers can thus also be unlocked. Thus, decompaction of cellulose-based fibers can be achieved by the hydration according to the invention.

Aqueous Unlocking Solution

The term "aqueous unlocking solution" is understood herein to mean an aqueous solution of one or more amino acid(s) and/or peptide (s) fully dissolved herein. Preferably, naturally occurring amino acids and/or peptides consisting of or containing these amino acids are in a completely water-soluble form. Preferably, it is a solution of one, two or more amino acid (s) and/or peptide (s), in the individual and/or total concentration in a range of 10 μm/l to 3 mol/l, more preferably between 1 mmol/l and 1 mol/l and more preferably between 0.1 mol/and 0.5 mol/l. These may be L- or D-forms or racemates. Preferred is the use of the L-form. Preferred are alanine, arginine, asparagine, aspartic acid, glutamine, glutamic acid, glycine, histidine, isoleucine, leucine, lysine, phenylalanine, proline, serine, threonine, tryptophan, tyrosine and valine. The amino acids arginine, lysine, histidine and glutamine are particularly preferred. The peptides which can be used according to the invention may be di-, tri- and/or polypeptides. The peptides of the invention have at least one functional group that can bind or bind a proton. The preferred molecular weight is less than 500 kDa, more preferably <250 kDa more preferably <100 kDa, and most preferably <1000 Da. The preferred functional groups are, in particular, a guanidine, amidine, amine, amide, hydrazino, hydrazono, hydroxyimino or nitro group. The amino acids may have a single functional group or contain several of the same class of compounds or one or more functional group (s) of different classes of compounds.

The amino acids and peptides according to the invention preferably have at least one positively charged group or have a positive overall charge. Particularly preferred peptides contain at least one of the amino acids arginine, lysine, histidine and glutamine in any number and sequential order. Particular preference is given to amino acids and/or derivatives which contain at least one guanidino and/or amidino group. The guanidino group is the chemical residue $H_2N-C(NH)-NH-$ and its cyclic forms, and the amidino group is the chemical residue $H_2N-C(NH)-$ and its cyclic forms. These guanidino compounds and amidino compounds preferably have a water distribution coefficient ($K_{OW}$) between n-octanol and water of less than 6.3 ($K_{OW}$<6.3). Particularly preferred are arginine derivatives. Arginine derivatives are defined as compounds having a guanidino group and a carboxylate group or an amidino group and a carboxylate group, wherein guanidino group and carboxylate group or amidino group and carboxylate group are separated by at least one carbon atom, which means at least one of the following groups is located between the guanidino group or the amidino group and the carboxylate group: $-CH_2-$, $-CHR-$, $-CRR'-$, wherein R and R' independently represent any chemical residues. Of course, the distance between the guanidino group and the carboxylate group or the amidino group and the carboxylate group can also be more than one carbon atom, for example in the following groups $-(CH_2)n-$, $-(CHR)n-$, $-(CRR')n-$, where n=2, 3, 4, 5, 6, 7, 8 or 9, as is the case, for example in amidinopropionic acid, amidinobutyric acid, guanidinopropionic acid or guanidinobutyric acid. Compounds having more than one guanidino group and more than one carboxylate group are, for example, oligoarginine and polyarginine. Other examples of compounds falling within this definition are guanidinoacetic acid, creatine, glycocyamine. Preferred compounds have as a common feature the general formula (I) or (II).

Preferred compounds have as a common feature the general formula (I) or (II)

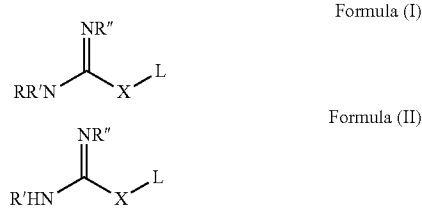

Formula (I)

Formula (II)

where

R, R', R", R'" and R"" independently from each other represent $-H$, $-CH=CH_2$, $-CH_2-CH=CH_2$, $-(CH_3)=CH_2$, $-CH=CH-CH_3$, $-C_2H_4-CH=CH_2$, $-CH_3$, $-C_2H_5$, $-C_3H_7$, $-CH(CH_3)_2$, $-C_4H_9$, $-CH_2-CH(CH_3)_2$, $-CH(CH_3)-C_2H_5$, $-C(CH_3)_3$, $-C_5H_{11}$, $-CH(CH_3)-C_3H_7$, $-CH_2-CH(CH_3)-C_2H_5$, $-CH(CH_3)-CH(CH_3)_2$, $-C(CH_3)_2-C_2H_5$, $-CH_2-C(CH_3)_3$, $-CH(C_2H_5)_2$, $-C_2H_4-CH(CH_3)_2$, $-C_6H_{13}$, $-C_7H_{15}$, cyclo-$C_3H_5$, cyclo-$C_4H_7$, cyclo-$C_5H_9$, Cyclo-$C_6H_{11}$, $-C\equiv CH$, $-C\equiv C-CH_3$, $-CH_2-C\equiv CH$, $-C_2H_4-C\equiv CH$, $-CH_2-C\equiv C-CH_3$, or R' and R" form the residue $-CH_2-CH_2-$, $-CO-CH_2-$, $-CH_2-CO-$, $-CH=CH-$, $-CO-CH=CH-$, $-CH=CH-CO-$, $-CO-CH_2-CH_2-$, $-CH_2-CH_2-CO-$, $-CH_2-CO-CH_2-$ or $-CH_2-CH_2-CH_2-$;

X represent $-NH-$, $-NR""-$, or $-CH_2-$ or a substituted carbon atom; and

L represents a C1 to C8 linear or branched and saturated or unsaturated carbon chain having at least one substituent selected from the group enclosing or consisting of —NH$_2$, —OH, —PO$_3$H$_2$, —PO$_3$H$^-$, —PO$_3^{2-}$, —OPO$_3$H$_2$, —OPO$_3$H$^-$, —OPO$_3^{2-}$, —COOH, —COO$^-$, —CO—NH$_2$, —NH$_3^+$, —NH—CO—NH$_2$, —N(CH$_3$)$_3^+$, —N(C$_2$H$_5$)$_3^+$, —N(C$_3$H$_2$)$_3^+$, —NH(CH$_3$)$_2^+$, —NH(C$_2$H$_5$)$_2^+$, —NH(C$_3$H$_7$)$_2^+$, —NHCH$_3$, —NHC$_2$H$_5$, —NHC$_3$H$_2$, —NH$_2$CH$_3^+$, —NH$_2$C$_2$H$_5^+$, —NH$_2$C$_3$H$_7^+$, —SO$_3$H, —SO$_3^-$, —SO$_2$NH$_2$, —C(NH)—NH$_2$, —NH—C(NH)—NH$_2$, —NH—COOH, or

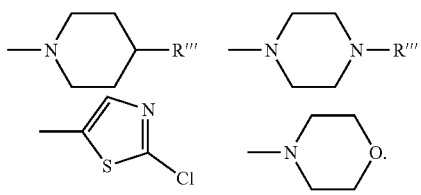

It is preferred that the carbon chain L is in the range of C1 to C7, more preferably in the range of C1 to C6, further preferably in the range of C1 to C5, and most preferably in the range of C1 to C4.

Preferably L represents —CH(NH$_2$)—COOH, —CH$_2$—CH(NH$_2$)—COOH, —CH$_2$—CH$_2$—CH(NH$_2$)—COOH, —CH$_2$—CH$_2$—CH$_2$—CH(NH$_2$)—COOH, —CH$_2$—CH$_2$—CH$_2$—CH$_2$—CH(NH$_2$)—COOH, or —CH$_2$—CH$_2$—CH$_2$—CH$_2$—CH$_2$—CH(NH$_2$)—COOH.

Also preferred are compounds of the general formula (III) as shown below:

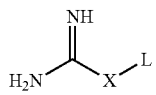

wherein the residues X and L have the meanings as disclosed herein.

Also suitable are di-, tri- or oligopeptides as well as polypeptides which are composed of one, two or more amino acids. Preferred are short-chained peptides, e.g. RDG. Particularly preferred are peptides which consist of amino acids which have both hydrophobic and hydrophilic side groups, such as (for example according to amino acid nomenclature) GLK, QHM, KSF, ACG, HML, SPR, EHP or SFA. Further particularly preferred are peptides which have both hydrophobic and cationic and/or anionic side groups, such as RDG, BCAA, NCR, HIS, SPR, EHP or SFA. Further examples with 4 amino acids are NCQA, SIHC, DCGA, TSVR, HIMS or RNIF or with 5 amino acids are HHGQC, STYHK, DCQHR, HHKSS, TSSHH, NSRR.

Particularly preferred are RDG, SKH or RRC.

Unlocking solutions according to the invention may contain further compounds which are completely dissolved herein. These may be compounds for adjusting the pH of the solution, in particular an acid or base, such as urea or triethylamine or acetic acid or uric acid, or compounds having surface-active properties, such as, DMSO or SDS. Also included herein are stabilizers such as antioxidants or reducing agents. Preference is furthermore given to compounds which permit decomposition of constituents of the starting material, preferred are compounds from the group of sulfites and sulfates and also carbonates. These are preferably initially introduced in a concentration of between 0.01 and 30% by weight in the unlocking solution.

Proteins

The term "proteins" as used herein means macromolecules composed of amino acids linked together by peptide bonds. The proteins referred to herein have >100 amino acids. They may be present in their primary structure, secondary structure or tertiary structure as well as in a functionally active form. In the case of the secondary structure, the spatial geometry may be in the form of an α-helix, β-sheet, β-loop, β-helix or may be present in random form as random-coil structures.

Carbohydrates

The term "carbohydrates" as used herein includes all C3 to C6 sugar molecules as well as compounds composed thereof. This includes but is not limited to: monosaccharides, such as hexoses, including glucose or fructose, and pentoses, including ribose and ribulose, and triols: glyceraldehyde, dihydroxyacetone; furthermore, disaccharides such as maltose, sucrose, lactose, as well as polysaccharides such as dextrans, cyclodextrins, starch or cellulose. In starch, amylose and amylopectin are to be distinguished.

While monosaccharides and most disaccharides and some polysaccharides are water soluble, higher molecular weight carbohydrates are water insoluble. Higher molecular weight carbohydrates, which are preferably linked together alpha-1,4-glucosidically and/or alpha-1,6-glucosidically, are herein considered to be complex carbohydrates. In addition to starch and cellulose, glycogen, chitin, callose, fructans, pectins, among others, belong to this group. This also means complex structures made of carbohydrate agglomerates, as is the case with a starch granule.

Aromas and Flavors

The term odor/aroma and flavoring agent are synonymously used herein with flavors. In virtually all organic mixtures of biogenic origin organic compounds are present, which lead to a sensory perception in the sense of a taste or a smell. The structural composition of these carbon-based compounds is heterogeneous. Some typical classes of compounds are alkaloids, alcohols, aldehydes, amino acids, aromatic hydrocarbons, esters, lactones, cyclic ethers, furans, furanoids, free fatty acids, flavonols, glycosides, ketones, saturated and unsaturated hydrocarbons, enamine ketones, ketopiperazines, isoprenoids, mono-terpenes, terpenes, cyclic terpenes, triterpenes, triterpenoids, tetraterpenes, sesquiterpenes, sequiterpenoids, sterols, phytosterols, purine derivatives, phenylpropanoids, phenols and/or hydroxycinnamic acid derivatives. These classes of compounds can be present both individually and in any composition.

Plant Pigments and Colorants

The term "colorant" summarizes organic compounds which can be present in starting materials of biogenic origin typically in different quantities and compositions side by side. By the term "plant colorants" herein are meant all coloring compounds. This concerns in particular the group of chlorophylls and their degradation products, such as pheophyline, chlorophyllide, pheophorbide, phyropheophytine, chlorine, rhodine and purpurine. In addition, however, there are also compounds that are grouped under the group of carotenes or carotenoids. However, there might be other classes of compounds, such as flavonoids, curcumins, anthrocyans, betaines, xanthophylls, which also include carotenes and lutein, including indigo, camphorol and xanthophyllins, such as neoxanthine or zeaxanthin.

Methods

Method of Providing Plant-Based Starting Material.

Depending on the different origin and production possibilities of the starting materials which can be used according to the invention, these can be present in different forms and states. For example, whole/intact seeds, grains, kernels, nuts, vegetables, fruits, flowers, ovaries or roots can be involved and/or wholegrain or partially disrupted, broken, comminuted, powdered, ground, crushed or pressed plant materials and/or plants materials which have partially or completely undergone a fermentative or disintegrative process, in particular by an autolysis/microbial degradation/chemical-physical reaction, and/or residues from agricultural production/food production or utilization. The broken, split, comminuted, powdered or liquidized or hydrated plant-based starting materials may be presented as continuous or discrete pieces or complexed, e.g. as pellets or molded compound or in a loose composite, such as granules or bulk or in isolated form, such as a flour or powder or in the form of a suspension. The consistency, shape and size of the plant-based starting materials is in principle irrelevant, but preferred are comminuted plant starting materials that allow easier unlocking. Preferably, maximum diameters of the dispersible particles/peaces of the plant-based starting materials are between 100 μm and 100 cm, more preferably between 0.5 mm and 50 cm, more preferably between 1 mm and 20 cm and more preferably between 2 mm and 5 cm. The form of the suitable plant-based starting materials is arbitrary, as well as the consistency, which may be hard or soft, or it may be in a liquid form. In this case, the starting material may have any desired temperature, preferably a heated starting material, as obtained, for example, following a pressing procedure. If the plant-based starting material does not fulfill the appropriate properties/requirements for one of the process operations according to the present invention, these conditions can be established by methods available from the prior art. These include, in particular, methods which enable and/or facilitate the unlocking of the plant-based starting material according to the invention. These include, in particular, mechanical processes with which the plant-based starting material can be comminuted. In this case, it may be necessary, in particular for process economization, to first comminute and then dry or to dry and then comminute the plant material. In one process embodiment, the comminuted and then dried plant-based starting material is comminuted to a certain particle size before process stage a), preferably particle sizes between 10 μm and 2 cm, more preferably between 30 μm and 5 mm. According to the invention, however, comminution can also take place during or after the addition of an unlocking solution.

In one process embodiment, lignin-containing components of the plant-based starting materials are first removed. These may be, for example, shell materials of the plant-based starting materials, such as seed coat, husks or shells, such as those of apple or grape seeds. For example, mechanical methods known from the prior art can be used for this purpose. In a further preferred embodiment of the method, a method for dissolving and/or disintegrating lignin before carrying out process step a) or a1) can be carried out. Such methods are known in the art, for example as a "Kraft method". For example, degradation or dissolving of lignin is achieved by boiling with a caustic solution.

The starting materials are filled into a suitable container, which can preferably be filled from above and has a closable outlet at the bottom.

Methods for Preparing and Using Aqueous Solutions for Disintegration and for Unlocking of the Starting Material The unlocking solutions according to the invention are prepared using the unlocking compounds according to the invention as defined herein. For this purpose, one or more of the compounds are dissolved in water, wherein the water may be a clarified process water, completely ion-free water and well or city water. For solvation it may be necessary to raise the temperature and/or continue mixing for up to 2 days. Preferably, a pH of the cationic amino acid or peptide solution ranges from 7 to 14, more preferably between 8 and 13, and more preferably between 8.5 and 12.5. In one embodiment, the pH can be adjusted to any pH range between 6 and 14 by the addition of an acid or a base. Acids and bases known in the art may be used, such as caustic soda or HCl.

Additives can be added to the solutions which improve or accelerate the unlocking and recovery of cellulose-based fibers or disintegrate and/or dissolve other constituents of the starting material. Such compounds include, but are not limited to, the following, such as: urea, NH3, triethylamine; ionic or nonionic surfactants such as SDS or DMSO; antioxidants or $NaSO_3$, sodium bisulfite, sodium sulfite. Preferably, the compounds are dissolved in water in a concentration of between 0.1 and 30% by weight, more preferably in a concentration of between 0.5 and 15% by weight, and most preferably between 1 and 5% by weight.

Furthermore, the unlocking solutions according to the invention can be combined with additives/auxiliary compounds which in particular improve the solubility of certain compounds of the starting material, these include, among others, alcohols, fatty acid esters, lactones.

The unlocking solutions can be prepared at any temperature and added to the starting material in the process steps a1), b) and c1), c2), c3), or d1), d2) and d3). The application can be carried out in droplets, dropwise or streams, continuously or discontinuously to, into and/or onto the starting material. In a preferred embodiment, this is done under exclusion of air and/or under inert gas conditions. The application is carried out by feeding a prepared unlocking solution in a controlled manner from a storage tank via a supply line to the starting material.

Methods for Carrying Out Method Step 1a): Disintegration of the Plant-Based Starting Material from Step a) by a Thermal and/or Mechanical Disintegration Method.

For carrying out the obtainment and production of disintegrated, decompacted cellulose-based fibers according to the invention, the cellulose-based fibers must be dissolved out of the organic matrix in which they were formed and decompacted, i.e., it is necessary to break/release/loosen the bonds of the cellulose-based fibers with each other and with other organic compounds in the original composite, so that the enclosed/embedded organic compounds can be released/separated by water. Thus, in order to prepare disintegration according to the invention the cellulose-based fibers physical and/or chemical processes must be used, thus the cellulose-based fibers can be dissolved out, or are leachable out of a solid and water-insoluble composite structures, or can be dissolved out of surrounding composite structures (e.g. shells) and therefore can be decompacted then. Preferably, thermal or mechanical methods are used as the physical methods by which disintegration is performed. Further preferred is the use of electro-magnetic waves, such as microwaves. The selection of the method depends on the water and/or oil content, the consistency and type of plant-based starting material.

In principle, thermal disintegration is advantageous if the plant-based starting material has a high water content, as in fresh fruits and vegetables. Here, the disintegration is preferably carried out by a transfer of thermal energy by water or water vapor. Preferably, pressurization is carried out at the same time.

A mechanical disintegration is particularly advantageous if the plant-based starting materials have a low water content and/or is enclosed in seed coat/shells that are impermeable to water. Furthermore, a mechanical method is preferable when another fraction of the plant-based starting material, such as oil, should be removed first.

In a preferred process embodiment, disintegration takes place in the case of plant-based starting materials, in that the starting material is completely or partially mechanically comminuted, placed in a water bath and heated until the proportion of the starting material, which essentially contains the recoverable cellulose-based fibers, is so soft that it decays to a mushy or liquid phase upon application of a slight force, e.g. by mashing with the fingers. This is particularly advantageous if, owing to the different strengths of various structures, following one of the aforementioned disintegration forms, the different structures, such as, for example, the mesosperm and the shell or seed coat, can very easily be differentiated from one another as layers and mechanically separated. In a preferred embodiment, the heating takes place together under pressure in an autoclave. In a preferred embodiment, plant-based shell/seed coat materials are removed before and/or after disintegration of the plant-based starting material.

In a particularly preferred embodiment, the plant-based starting material is disintegrated by prior introduction into an aqueous solution comprising an aqueous unlocking solution according to the invention. In principle, the volume or weight ratio can be chosen freely, but it is advantageous if the plant-based starting material is completely wetted by the unlocking solution. The duration of exposure to the unlocking solution depends on the plant-based starting materials used. Preferred is a duration between 1 minute and 48 hours, more preferably between 10 minutes and 14 hours and more preferably between 20 minutes and 6 hours. The temperature at which the exposure of the plant-based starting material is carried out with the aqueous unlocking solutions is, in principle, freely selectable. Preferred are temperatures between 5° and 140° C., more preferably between 10° and 120° C. and more preferably between 15° and 90° C. Further preferred is a previous and/or simultaneous and/or subsequent treatment of the plant-based starting material with compounds which cause disintegration or chemical reaction of lignin bonds. Preference is given to the use of sulfite and sulfate compounds. Particularly preferred is sodium bisulfite. This process step can be dispensed with or is unnecessary if the plant-based starting material is already present in a disintegrated form which qualifies for the use of process step b) and in which the implementation of process step a1) has no advantage over a further process sequence with process step b).

Methods for carrying out method step b): Impregnation of the disintegrated plant-based material from step a) or a1) with an aqueous unlocking solution.

In this process step, the wetting of the surfaces of the constituents within the plant-based starting material must be ensured. This can be done with prior art methods on intact or disintegrated plant-based starting materials.

Preference is given to placing the plant-based material to be unlocked into an aqueous unlocking solution.

For the economical use of the unlocking solution, it may be sufficient to spray the plant-based material to be unlocked with the unlocking solution during mixing, whereby wetting can take place without formation of a free water phase, which is usually the case when wetting is performed and which then has to be separated off preferably before the next process step. Preferably, a water volume ratio of the aqueous unlocking solution to the bulk of the plant-based material is between 0.3 to 30% by weight, more preferably between 0.5 and 20% by weight, more preferably between 0.7 and 10% by weight and more preferably between 0.8 and 5 wt %. In a variant of the method, the impregnation/wetting of the plant-based material with one of the unlocking solutions takes place during the application of one of the disintegration methods or immediately afterwards. In one process variant, the impregnation is carried out directly together with compounds that enable/accelerate disintegration of the plant-based starting material. This may also be the case even if, for example, the aqueous unlocking solution is used for disintegration in a thermal process. In the context of disintegration, wetting of the plant-based material with the compounds of the unlocking solution takes place here. In a preferred variant of the method, impregnation/wetting takes place under reduced or over-pressure conditions in a container suitable for this purpose. Preferably, the pressure is in the range of 1 mbar to 50 bar, more preferably from 10 mbar to 10 bar and more preferably from 100 mbar to 5 bar. In principle, the impregnation/wetting can take place at any temperature. Preference is given to simultaneous heating of the plant-based material in order to accelerate the wetting/soaking process. It is therefore preferred to carry out the process step at a temperature between 5° and 150° C., more preferably between 8° and 140° C., more preferably between 10° and 120° C. and more preferably between 15° and 90° C. It is preferred to carry out the process step with simultaneous increase in temperature and underpressure or overpressure. The preferred duration of the process step depends on the permeability and the degree of unlocking of a previous disintegration. Preferred is a duration between 10 seconds and 10 days, more preferably between 1 minute and 2 days, more preferably between 10 minutes and 24 hours, even more preferably between 15 minutes and 8 hours, and most preferably between 20 minutes and 4 hours.

For the execution according to the invention it must be ensured that the above-mentioned processes achieve a moisture content of >20% by weight in the plant-based starting material as well as complete hydration of the readily soluble compounds. The completeness of permeation and hydration can also be checked very easily by suspending, for example, a 1 ml sample of the unlocked plant material in 1,000 ml of water and stirring with a magnetic stirrer for 10 minutes at a rotation frequency of 300/min. If after stopping agitation there are fibers visible to the naked eye with a slow sedimentation tendency and at the same time shell parts or other constituents, such as starch granules or fragments of these are present without recognizable adhesions in addition to the isolated cellulose-based fibers in the sieve residue of the suspension, the duration of the impregnating/wetting phase is sufficient. In the process variants, the amino acid and/or peptide solutions used for unlocking are preferably added in a mass ratio of between 0.3:1 and 3:1 to the plant-based starting material which can be penetrated by the solutions, and mixed with it in order ensured complete wetting/impregnation of the organic starting material. However, it is also possible to select significantly larger volume ratios, especially if the constituents to be removed from the cellulose-based fibers are to be simultaneously dissolved and removed in an aqueous medium with this solution. In a variant of the method, a disintegrated starting material is provided. Preferably, a mixture is carried out with one of the unlocking solutions according to the invention, which ensures complete penetration. The temperature at which this takes place can be chosen freely, preferred are temperatures between 4° and 90° C., more preferably between 15° and 70° C. and more preferably between 20° and 45° C. The duration of the penetration phase naturally depends on the type and nature of the plant-based starting material. Preferred is a duration between 5 minutes and 24 hours, more preferably between 10 minutes and 12 hours and more preferably between 20 minutes and 6 hours.

Methods for Carrying Out Process Step c1): Rinsing Out of Soluble Constituents of the Plant-Based Starting Material and Decompacting the Cellulose-Based Fibers.

In this process step, the soluble hydrated constituents of the plant-based material that have been hydrated and thus have been partly dissolved/dissolved, are detached/separated from the surfaces of the cellulose-based fibers and transferred into an aqueous rinsing solution or suspended therein. Preference is given to the use of water as a rinsing solution. These may be tap, well, partially deionized or distilled water. In one type of process, the rinsing liquid is enriched with additives/auxiliary compounds, preferably with water-soluble compounds. Preferred additives are substances which cause a lowering of the water surface tension, such as DMSO. Particularly suitable additives for this process step are ionic and nonionic surfactants. In appropriate cases, a shift in the pH is made, for example with an acid or a base. In one process embodiment, alcohols are used as a rinsing liquid or as an additive. It is preferable to carry out this process step with a liquid volume which is large enough to be able to take up the dissolved soluble constituents of the plant-based material and to prevent re-adherence/incorporation of these constituents onto/into the cellulose-based fibers. Preferably, the use of a volume ratio of the rinse solution to the volume of plant-based material from process step b) is between 1:1 and 500:1, more preferably between 2:1 and 300:1, more preferably between 3:1 and 150:1, and even more preferred between 5:1 and 20:1. Preferably, the suspension is agitated, using methods known in the art. In a preferred embodiment, the suspension is pumped one or more times through nozzles or thin conduits to ensure a turbulent flow. This process preferably takes place under pressure. In a further preferred embodiment, a shear mixture, preferably with a rotor-stator shear mixing method or a colloid mill, is carried out. The required duration of the rinsing process depends on the starting material and the other process conditions. Preferred is a duration between 1 minute and 48 hours, more preferably between 2 minutes and 24 hours, more preferably between 3 minutes and 6 hours and more preferably between 4 minutes and 2 hours. The temperature of the suspension during the rinsing process can be chosen freely. Preferably, a temperature between 5° and 150° C., more preferably between 8° and 140° C., more preferably between 10° and 120° C. and more preferably between 15° and 90° C. From the prior art, there are processes and methods with which it is possible to check whether sufficient removal/separation of soluble constituents of the starting material has taken place in the process step. For example, for testing purposes, a volume of 5 ml of a filter residue of the suspension taken with a 0.6 mm sieve mesh from the agitated suspension of this step can be used, which is resuspended in 100 ml of distilled water and agitated with a high-performance shear mixer (e.g. Ultrathurrax) for 30 seconds at 10,000 rpm. Following this, the suspension is filtered with the same filter as before. The degree of turbidity of the filtrate is determined, for example with a turbimeter.

At a turbidity level of <20 FTU sufficient rinsing off/separation of the plant-based constituents has been achieved in this step of the process. Thus, it is ensured in this process step that separation of soluble constituents of the plant-based starting material from the cellulose-based fibers is preferably achieved to >90% by weight, more preferably >95% by weight, more preferably >97% by weight and more preferably >99% by weight, whereby cellulose-based fibers can be obtained in which there is a content of other adhering/incorporated soluble organic and/or inorganic compounds that is preferably <5% by weight, more preferably <3% by weight, more preferably <1% by weight. The unlocked decompacted cellulose-based fibers are present if they have a hydration volume of preferably >100% by volume, more preferably >150% by volume, more preferably of >200% by volume, more preferably of 300% by volume and most preferably of >400% by volume and are present in isolated/singular form.

Methods for Carrying Out Process Step c2): Separation of Water-Insoluble Organic Solids of the Starting Material.

The solid constituents of the starting material which are meant herein are organic compounds which do not correspond to the cellulose-based fibers according to the invention and which do not dissolve further as a result of one of the disintegration/unlocking processes according to the invention and are present as particulate structures, for example retrievable by means of filtration. Such organic solids include, in particular, seed coats/shells, skins, husks, hulls, stalks or bark material. Preferably, recovery of these solid constituents is accomplished by state-of-the-art filtration techniques. However, process techniques can also be applied in which a separation of the solid matter out of the liquid mixture is accomplished, for example by means of centrifugation, such as a sieve decanter or a cyclone separation technique. Preference is given to cyclone separation technique, as can be performed with a hydrocyclone.

Following process step c1) or c2), process step c3): "conditioning of the cellulose-based fibers", can be carried out. In a variant of the method, this is done by placing the wet or dried mass of cellulose-based fibers in a vessel together with a solution containing a conditioning fluid and keeping it therein for a period of preferably 30 seconds to 2 days, more preferably 1 minute to 1 day, and more preferably 5 minutes to 3 hours with continuous mixing. The subsequent removal of the free and optionally bound water phase then takes place in the next process step.

Instead or in addition, the optional process step c3: "functionalizing the surfaces of the cellulose-based fibers", take place. The process technology can be carried out as described above. In this case, an adhesion/introduction of substances/compounds/microorganisms onto/into the cellulose-based fibers in the moist or dried state of the cellulose-based fibers is carried out with preparations which contain the compounds/substances or microorganisms to be adhered/introduced.

In both optional process steps, any compounds may be present individually or in combination, at any pH and temperature, in the solutions intended for this purpose. It can be done at any positive or negative pressure for any duration.

Methods for Removing Bound Water from Cellulose-Based Fibers in Step d1) and d2)

Methods for separating free or bound water from/out of wet/moist materials are known in the art. In this case, the free water phase is the volume of water bound by the obtained and produced cellulose-based fibers on their outer surfaces, in particular by capillary forces resulting from the assembly of cellulose-based fibers, which can be separated from the cellulose-based fibers by gravity either by flowing off spontaneously, e.g. by isolating the cellulose-based fibers, or by mechanical methods, such as a filtration process. The bound water content consists of the volume of water, which is not separated by the aforementioned measures and can only be separated from the cellulose-based fibers by means of physical/thermal processes. Preferably, the separation of free water may be accomplished by filtration of the cellulose-based fibers by retaining them in a sieve. In a preferred method embodiment, the separation of free and/or bound water by a filtering of the cellulose-based fibers is carried out by means of a vibrational sieving process. Preferably, this is configured as a self-unloading swing/tumble screen. Preferably, a screen mesh size is used, which preferably guarantees retention of >90% by weight, more preferably of >95% by weight and more preferably of >99% by weight of the cellulose-based fibers from the rinsing liquid of process step c): "rinsing out of soluble constituents of the plant-based starting material".

The sieve mesh size can be selected, for example, by applying a sample of the process liquid of process step c) to sieves with different sieve mesh dimensions of a laboratory vibratory sieve analyzer and determine the number and size of the cellulose-based fibers found in the filtrate. Alternatively, for example, a curved screen or a belt screen for the separation task can be used, the appropriate sieve mesh dimensions are determined in an analogous manner. Another prior art method of performing process step d1) is chamber filter presses. This process technology is particularly suitable when separation of a free and bound water phase should take place immediately and in one operation. Hereby a high surface pressure can be exerted on the material retained by means of a filter fabric, whereby the main part of the free and bound water phase can be removed. Selection of the sieve mesh size of a suitable filter cloth is carried out in an analogous manner to the selection of a sieve. The pressurization applied at a pressing process of the filter residue depends on the desired residual moisture content of the cellulose-based fiber mass. Preferred are pressures between 10 $g/cm^2$ and 500 $kg/cm^2$, more preferably between 100 $g/cm^2$ and 100 $kg/cm^2$ and more preferably between 500 $g/cm^2$ and 50 $kg/cm^2$. Preference is given to a process in which first a screening of the cellulose-based fibers from the process water of process step c1) or c2) or c3) is performed by means of a sieve and in a further part of this process step bound and/or other free water is released/separated from the filter residues in a pressing device. Preferred press devices are also a belt filter press or a lifting punch filter press. Other pressing devices that are suitable for carrying out the method are screw press devices. In a preferred method embodiment, a decanter or sieve decanter is used to remove the free and bound water phase. But there are also other methods for the separation of free and/or bound water possible, such as by using a belt dryer or vacuum or freeze-drying.

Furthermore, centrifuge processes, such as centrifuges or decanters, can be used to carry out the process step. In one type of process, the cellulose-based fibers obtained are subjected to one or more further purification and/or conditioning and/or functionalization processes. For this, no or only partial removal of the free and/or bound water phase may be required. There are also applications in which a defined residual moisture is to be maintained. Preferably, a residual moisture content of between 30 and 200% by weight, more preferably between 40 and 150% by weight and even more preferably between 45 and 120% by weight is achieved.

In a process embodiment, the process step d2) is followed by the process step d1) or d3): "drying of the cellulose-based fibers".

This process step is to be used when the fiber mass obtainable from step d1) has a water content that is too high. Preference is given to thermal processes in which drying is carried out at a low temperature, preferably <150° C., more preferably <120° C., more preferably <100° C., even more preferably <85° C. and particularly preferably <70° C. Preference is given to air jet processes, agglomeration processes, spray drying or vacuum drying, and belt/contact drying processes. A residual moisture content of the dried cellulose-based fibers is preferably between 8 and 35% by weight, more preferably between 10 and 30% by weight and more preferably between 12 and 25% by weight.

Methods for Carrying Out Method Step c3) or d3): Conditioning the Unlocked, Decompacted, Cellulose-Based Fibers.

In this process embodiment, adhesion/incorporation of organic and/or inorganic compounds and/or microorganisms lining the inner and outer surfaces of the unlocked, decompacted cellulose-based fibers is achieved, whereby the obtainable cellulose-based fibers obtained specific properties. This can be done, for example, by spreading the wet, partly dried or already dry mass of cellulose-based fibers onto a belt filter and then by spraying, impregnating/wetting with a functionalizing solution or the solution is passed through it. Preference is given to a penetration of a gas/vapor phase through the mass of distributed cellulose-based fibers on a filter. Immediately thereafter or after any period of time, method step d1) or d2) can then be carried out either for the first time or repeatedly. In a variant of the method, the optional process step c3) and/or d3) is carried out by adding moist, partly dried or dried mass of cellulose-based fibers to a vessel together with a solution containing a conditioning solution and for a duration of preferably between 30 seconds and 2 days, more preferably between 1 minute and 1 day, and more preferably between 5 minutes and 3 hours, under continuous mixing. Thus, in process step c3) a surface conditioning and in process step d3) a surface functionalization can be performed. Surface functionalization may be accomplished by the same methods and solutions as performing surface conditioning (see below). In this case, for example, an adhesion/incorporation of substances/compounds/microorganisms onto/into the cellulose-based fibers, in the moist or partly dried state of the cellulose-based fibers with preparations, which contain the compounds/substances or microorganisms to adhere/incorporate. In a preferred embodiment, this is done by distributing the cellulose-based fiber mass on a belt filter and then spraying, impregnating or flowing a functionalizing solution onto/through this. Immediately after performing one or more of these process steps, the process step d1) and/or d2) can then be carried out for the first time or repeatedly, after any duration.

Production and Use of Cellulose-Based Fibers.

The cellulose-based fibers of the invention may be obtained in a moist form (that means with a proportion of free and/or bound water phase), partly dried form (that means absence of a free water phase in the presence of a bound water content) or in dry form (that means a residual water content of <5 wt %). They can be obtained in isolated form or as a malleable mass from the process steps. They are considered to be produced, if they have the specified product properties. Preference is given to the use in the form of a moist, spreadable and maleable composition having a preferred residual moisture content of from 20 to 100% by weight, more preferably from 30 to 85% by weight. Also preferred is a powdered or free-flowing consistency, with a residual moisture of 0 to 20% by weight, more preferably from 5 to 15% by weight.

For the production of additional product properties, the methods described herein for surface conditioning and/or surface modification and/or surface functionalization and/or incorporation of substances/compounds/microorganisms can be used. For this purpose, one or more of the optional process steps:

e1) production of surface conditioning and/or surface modification of cellulose-based fibers,
e2) production of surface functionalization of cellulose-based fibers,
e3) adhesion/incorporation of substances/compounds/microorganisms onto/into cellulose-based fibers,
following process step d) can be done.

The cellulose-based fibers according to the invention in hydrated form preferably have a maximum length of 10 μm to 2,000 μm. Preferably, they form/exist of three-dimensional structures with irregular boundaries/outer shape. Preferably, a broad distribution of the dimensions of the cellulose-based fibers is obtained. Preferably, the cellulose-based fibers have functional groups with which they can form electrostatic and/or covalent bonds with other compounds. These are preferably OH—, SH—, COOH—, $PO_4$— and/or NH— groups.

Preferably, the cellulose-based fibers have cyclic and/or aliphatic organic side groups, such as a fatty acid residues, but also sugar residues are preferred. Also preferred are cellulose-based fibers which have as side groups amino acids and/or peptides, such as cysteine or arginine.

This can be tested with prior art methods. For the determination of the fiber dimensions, for example, fiber analyzers are available, e.g. Fiberlab FS 300 (Valmet). The geometric spatial structure can be evaluated for example by means of cryo-TEM. The presence of functional groups on the surfaces of the cellulose-based fibers can be determined, for example, by titration, the determination of the conductivity or by mass spectroscopy (ICP-AES) of the combustion residue.

In a preferred embodiment, the dimensions of the obtained cellulose-based fibers can be reduced by mechanically comminuting the cellulose-based fibers. This can be done, for example, in cellulose-based fibers that are in a suspended and in a hydrated state in water by a high-frequency shear mixer/disperser or, if they are in the dried state, are ground e.g. with a cutting or grinding mill.

Methods for the Hydration of Cellulose-Based Fibers.

In the case of cellulose-based fibers in which, for example, after their obtainment or production, removal of free and/or bound water was carried out, the re-uptake of water can be made possible or accelerated by various methods. In one variant of the method, the cellulose-based fibers to be hydrated are placed in an electrolyte-free and ion-free water. In a further preferred embodiment, the water into which the cellulose-based fibers to be hydrated are placed, is heated, preferably to between 30° and 99° C., more preferably to between 45° and 80° C. and more preferably to between 50° and 65° C. Preference is given to a base pH of an aqueous solution in which hydration of cellulose-based fibers takes place. A solution of cationic amino acids and/or peptides is preferred. Particularly preferred are arginine solutions. The preferred arginine solutions have a concentration of dissolved arginine or arginine derivatives between 10 μmol and 0.6 mol/l, more preferably between 100 μmol to 0.3 mol/l and more preferably between 1 mmol and 0.1 mol/l. Preference is given to the use of additives/auxiliary compounds which have surfactant properties, for example SDS or DMSO, but also to other ionic and/or nonionic surfactants. In a preferred embodiment, the cellulose-based fibers are mechanically dispensed. Stirring devices are preferred for the dispensing process. Further preferred are shear force mixing devices such as rotor-stator shear mixers or colloid mills. The cellulose-based fibers suspended in water and to be hydrated are preferably dispensed by a shearing force mixer for 2 seconds to 15 minutes, more preferably for 10 seconds to 5 minutes, and more preferably for 30 seconds to 2 minutes, at any temperature. With the hydration processes, partial or complete hornification of cellulose-based fibers can also be partially or completely reversed.

Method for Testing the Water Retention Capacity and the Hydration Volume.

The water retention capacity may be determined by prior art methods. In one of the methods, water content is determined by suspension of a 0.5 g sample in 50 ml of distilled water in a 100 ml Erlenmeyer flask. After agitation for 1 hour at 20° C., the free water phase is removed using a G3 glass frit; together with the glass frit, the sample material is centrifuged at 2,000×g for 15 min. The amount of centrifuged liquid and the sample weight are determined. The water retention value (ratio) (WRR) is calculated according to the following formula $$WRR(\%) = \frac{\text{Sample wett material mass} - \text{sample dry mass}}{\text{Sample dry mass}} \times 100$$

The hydration volume can be determined by using the obtained decompacted cellulose-based fibers (e.g. 100 g with a water content of 100% by weight) and mixing in a water phase with a neutral pH and a volume ratio to the solid mass of the fibers of >1,000:1 using an intensive mixer for 3 minutes and then allowing the unbound water phase to drain through a sieve with a sieve mesh size of 50 μm. After 1 hour, the volume of the cellulose-based fiber mass is determined. This is followed by mechanical dewatering and drying of the material to a residual moisture content of <10% by weight. Then, the volume is determined and the volume ratio calculated.

Methods for Surface Treatment/Modification of Cellulose-Based Fibers.

The cellulose-based fibers according to the invention can be functionalized with processes from the prior art with functional compounds which are electrostatically and/or covalently bound to the cellulose-based fibers. The effects that can be achieved with such a functionalization include, among others, surface effects that may be summarized as anti-static, hydrophilic, hydrophobic, oleophilic, amphiphilic, electrostatic with a positive and/or negative surface charge, hygroscopic and/or conductive. The establishment of multiple combinations of the aforementioned surface properties is possible. The desired surface property and the selection of the compounds which can be used depend on the application of the functionalized cellulose-based fibers. Preference is given to electrostatic bonds to OH— groups, for example by alcohols or polyalcohols, polyvalent alcohols, amino alcohols, further amines, e.g. betaine, furthermore amides, imides, imidazoles, triazoles, melamine, creatine, creatinine, carnitine, furthermore organic acids, such as acetic acid, tartaric acid, lactic acid, malic acid, mandelic acid, gluconic acid, nitriloacetic acid, furthermore fatty acid esters, mono-/diglycerides, phospholipids, glycolipids, glyceroglycolipids, amino acids (especially arginine, lysine and histidine as well as glutamine and glutamic acid), mono-, di- or polypeptides such as the RDG peptide.

Furthermore, sugar compounds, such as dextrose or fructose, but also macromolecular compounds can be used for surface functionalization, for example polysaccharides, such as polydextrins or starch. Furthermore, cellulose derivatives can be used, such as methyl-, ethyl- or hydroxycellulose, as well as combinations of these are possible.

However, surface functionalization can also be carried out by adhesion/incorporation of reactive or reaction-promoting compounds onto/into the cellulose-based fibers, for example with carbonates, such as sodium bicarbonate or silicates, such as sodium metasilicate. Further preferred is the adhesion/incorporation of compounds onto/into the cellulose-based fibers in the form of micro-/nano-emulsions. Particularly preferred is the use of nano-emulsions of cationic amino acids or peptides, such as arginine or lysine with organic acids such as linolenic acid or ascorbic acid.

The compounds used for surface functionalization are to be dissolved in a suitable solvent (e.g., water, ethanol or acetone) and in an adequate concentration.

If necessary, pretreatment of the surfaces, for example to increase the reactivity, can be carried out using methods from the prior art, such as for example an alcohol, an oxidizing or reducing agent, such as an acid, an alkali or $H_2O_2$. If desired, a covalent carrier layer can be adhered/incorporated/coated with, for example by a silane, such as, for example, APTMS. In principle, moist, partly dried or dry cellulose-based fibers can be used for surface coating.

Preference is given to dried cellulose-based fibers. The cellulose-based fibers to be coated can be placed in a solution with coating compounds contained herein or placed in a device where a solution with coating compounds contained therein flows through them. In a preferred embodiment, the surface coating is carried out in an autoclave at an elevated temperature and pressure. If necessary, it may be necessary to apply high-energy radiation before and/or after surface functionalization and/or to expose the cellulose-based fibers to an elevated temperature.

Methods for Using Cellulose-Based Fibers.

The cellulose-based fibers according to the invention can be used in a fresh form or after storage and in moist (that means with a proportion of a free and/or bound water phase), partly dried (that means absence of a free water phase in the presence of a bound water content) or in dry form (that means a residual water content of <5% by weight). They can be used in the forms described above in isolated (singulated) form or as a malleable mass. Preference is given to the use in a form of a moist, spreadable and malleable composition having a preferred residual moisture content of from 20 to 100% by weight, more preferably from 30 to 85% by weight. A cellulose-based fiber mass produced by a preferred process is preferably completely free of germs, spores or microorganisms, unless they have been adhered/incorporated in one of the process steps. Therefore, moist or partly dried preparations of the cellulose-based fibers are stable (shelf life) preferably for >2 days, more preferably for >5 days, more preferably for >12 days and more preferably for >21 days after their preparation or after thawing from a frozen phase and under cooled conditions (e.g. at 6° C.) and can be used for foodstuffs. Cellulose-based fibers can be prepared and used in any of the previously described forms in a wet or partly dried state as a fresh product, under refrigerated conditions (e.g. at 6° C.), with or without evacuation of air, in suitable packaging for food preparation. For use, the partly dried or moist cellulose-based fibers are preferably dissolved in water at an arbitrary temperature, admixed to an aqueous preparation, or mixed/contacted with other materials for food preparation.

Preference is furthermore given to storage and use in powdered or pourable consistency, with a residual moisture from 0 to 20% by weight, more preferably from 5 to 15% by weight. Preparations of cellulose-based fibers produced in this manner can be stored practically indefinitely, since there is no risk of perishability in dry storage. In order to ensure the rapid hydration/water absorption of the dried cellulose-based fibers, it is advantageous to finely grind the dried cellulose-based fibers. Preference is given to cutting or grinding mills. Preferably, the dried cellulose-based fibers are provided in a powdered form, with a particle size of preferably <300 µm, more preferably <200 µm and more preferably of <100 µm, for the different applications.

For use in applications, the dried cellulose-based fibers can be used in the dried form, e.g. for use as bread crumbs or in a pharmaceutical formulation or in a hydrated form. In the latter case, the hydration can be carried out, for example, by adding the dried cellulose-based fiber preparation to water, causing it to swell; the swollen mass can then be used for the application as it is or is freed of the free liquid phase by filtering and then using it. On the other hand, hydration that is induced while being in the aqueous medium of the application is also possible.

Cellulose-based fibers according to the invention can be used in various food preparations. In one embodiment, convenience or instant preparations/mixtures are prepared herewith. This can be done by bringing together and mixing the cellulose-based fibers in one of the aforementioned forms with the other components of the preparation in undissolved and/or water-dissolved form. Using the form in which the aforesaid mixture has been obtained, that means in dry, partly dried or moist form, the mixture may then be packaged or formulated or is brought into another form, for example by drying by means of a stream of warm air and subsequent mechanical comminution to a defined particle size.

Applications

The embodiments of processes according to the invention can in principle applied to all plant based starting materials. These may be present in the form of unripe, ripening, ripened, overripe, aged or even damaged plant based starting material. Contaminated or spoiled plant-based starting materials can also be used to produce cellulose-based fibers according to the invention. The plant based starting material may be fully intact, damaged, crushed, peeled, pressed, ground or otherwise disintegrated. In particular, coarse meal or flours is suitable. In particular, coarse meal, which arise for example after a mechanical extraction of oils, so-called press cake, is also suitable. Also suitable are plant based starting materials which have previously been subjected to a thermal and/or liquid extraction process, e.g. with an alcohol or an organic solvent such as hexane. Also plant based starting materials, in which a thermal treatment has been carried out, are suitable. This also includes plant based products that are obtainable from a digestion and/or fermentation process, especially if they are residues, such as brewery residues (for example in the form of grain or grain flour), or pomace from apple cider production or olive pomace. In addition, residues of cocoa beans or sugar beet are included.

Preference is also given to residues of press residues which are found, for example, in the recovery of juices (for example apple, tomato or carrot juice) or pomace, e.g. of grapes or apples or extracts, as obtained in the production of jellies or liqueurs (e.g. blackberry jelly, cassis).

Further, products of plant-based starting materials derived from a peeling, dehulling, or deseeding process may be used.

The plant based starting materials which can be used for one of the processes according to the invention, or from which the cellulose-based fibers according to the invention can be obtained and produced, therefore comprise all vegetable seeds, such as linseed, poppy seeds, chia, amaranth, chili, tomatoes, anise, pea; Grains, e.g. of rapeseed, camelina, oats, hemp, wheat, buckwheat, rye, barley, maize, sunflowers, green spelt, jatropha; Fruit seeds/pits, e.g. from apples, pears, lemons, grapefruits, grapes, oranges, cherries, plums, apricots, peaches, whitty pear, medlars, mirabelles, rowanberries, pumpkins, melons, avocados; Legumes such as soybeans, field beans, mats beans, mung beans or kindey beans, peas, lentils such as e.g. Duckweed lenses, lupines or sesame; Vegetables such as cauliflower, broccoli, kohlrabi, zucchini, peppers, artichokes or okra; Bulbous plants, such as carrots or sugar beet; Fruits, such as apples, pears, quince, bananas, breadfruit, mango, kiwi, *maracuja*, melons, passion fruit, figs, pumpkin, pineapple, avocado, olives, mango, chayote, *guava*, papaya, tamarillo, *Marmota* apple, grape fruit, oranges, lemons or grapes; Berries such as rose hips, gooseberries, blueberries, blackberries, strawberries, elderberries, currants, cranberries, mulberries, chokeberries, raspberries, blackberries, sandorn; tuberous plants and roots, such as potatoes, beetroot, *batata*, turmeric, cassava, horseradish, celery, radishes, ginger, arakascha, taro, wasabi, yacon, salsify, asparagus, parsnip, mustard, Jerusalem artichokes, cattail, swede, Siberian angelica, yam, yam root, sunflower root, devil's claw or ginko; as well as cucumbers, such as salad or pickled cucumbers, as well as eggplant or zucchini; Nuts, such as almonds, hazelnuts, peanuts, walnuts, cashew nuts, Brazil nuts, pecans, pistachios, chestnuts, sweet chestnuts, dates. Furthermore, sugarcane.

The cellulose-based fibers produced according to the invention can in principle be used in all areas of life as well as in industrial processes and process sequences. The cellulose-based fibers according to the invention are particularly suitable for applications of human nutrition. In particular, they are suitable as a dietary food additive for calorie-reduced food preparations. In addition, the cellulose-based fibers according to the invention are suitable for dietary weight reduction.

Additionally they are a substitute for soluble carbohydrates, such as pectins or starch or used for the reduction thereof in food preparations. Furthermore, they can be used as a substitute for or for the reduction of oils or fats in food preparations. The cellulose-based fibers according to the invention are suitable for regulating intestinal activity and for altering/softening stool consistency. Further, they can be used as a dietary anti-oxidant. The cellulose-based fibers can likewise be used in animals for stool regulation and dietary weight reduction. Furthermore, cellulose-based fibers according to the invention are suitable for the thickening and stabilization of liquid or flowable foods and food preparations. Cellulose-based fibers prepared according to the invention increase the water-binding and retention capacity of food preparations. As a result, these cellulose-based fibers are also suitable for keeping the water content in foods or food preparations longer or keeping them fresh and reducing the risk of dehydration. Furthermore, the produced cellulose-based fibers can be used to introduce and/or stabilize substances/compounds or microorganisms in food or food preparations. As a result, for example, labile compounds, such as vitamins or antioxidants, can be stabilized/distributed in food or preparations. Furthermore, micro-organisms can be introduced into foods which exhibit increased metabolic activity, such as yeasts or lactic acid-splitting bacteria. These properties of such cellulose-based fibers can also be used to cultivate algae or other microorganisms and use them to produce substances/compounds or gases with increased efficiency. Cellulose-based fibers prepared according to the invention are particularly suitable for the preparation of lotions/creams/ointments or pastes for applications on skin or mucous membranes. In doing so, they enable improved water retention on the surface of the skin and mucous membranes as well as improved emulsifiability of hydrophilic and lipophilic compounds as well as the incorporation of compounds such as antioxidants or sunscreen compounds and lead to improved smoothness of the skin and mucous membranes. Furthermore, the cellulose-based fibers are very well suited as release agents for food products/food, which are cooked at high temperatures with direct or indirect heat, such as roasting, baking, grilling or deep-frying. Thus, cellulose-based fibers produced according to the invention can be used as release agents or as substitutes for breading/breadcrumbs, for example in the preparation of meat or fish as well as meat or fish products, potato or dough preparations. Further, cellulose-based fibers of the present invention are useful for formulating or preserving other nutrients or nutritional ingredients. This is the case in particular in the production of protein products, such as protein concentrates or isolates. However, preparations with oils/fats and/or soluble or complexed carbohydrates or aromas and flavors can be prepared and/or formulated and/or stored with the cellulose-based fibers according to the invention. Furthermore, cellulose-based fibers according to the invention are suitable for effecting a long-lasting moisturizing feeling on mucous membranes. Therefore, cellulose-based fibers are particularly suitable for treating a dry oral mucosa. In addition, cellulose-based fibers prepared according to the invention are suitable for reducing odors, in particular they are applicable for reducing or avoiding halitosis.

EXAMPLES

Unless otherwise stated, the following analytical procedures were used in the investigations:

The crude protein content of the samples was determined according to LMBG § 3 5 L 03.00-27, via the determination of nitrogen by the Dumas method. To convert the nitrogen content into the crude protein content of the samples, the factor 6.25 was used. The determination of nitrogen was carried out with the Leco system FP-528.

The fat content of the samples was determined according to Caviezel® with the DGF standard method K-I 2c (00). Fat content determination was carried out with a Buchi B-815 extraction unit as well as a Buchi B-820 fat estimator.

Droplet or particle sizes were determined by non-invasive laser light backscatter analysis (DLS) (Zetasizer Nano S, Malvern, UK). For this purpose, 2 ml of a liquid to be analyzed were filled into a measuring cuvette and inserted into the measuring cell. The analysis on particles or phase-bordering droplets is automatic. It covers a measuring range from 0.3 nm to 10 µm.

A quantification of the turbidity (turbidimetry) of the water phases (aqueous emulsions) was also carried out by means of a scattered light detection, in which the re-entry of a scattered beam at 90° was detected with a measuring probe immersed in a sample volume of 10 ml (InPro 8200-measuring sensor, M800-1 transmitter, Mettler Toledo, Germany). The measuring range is 5 to 4000 FTU. There were always duplicate determinations per sample.

The water binding capacity (WBC) of cellulose-based fibers was determined at room temperature. The implementation of the method was based essentially on the AACC method 56-20. For example, a 2 g sample to the nearest 0.01 g was weighed into a centrifuge tube and mixed with 40 ml demineralized water for one minute with a test tube shaker. After 5 min and after 10 min, the mixture was vigorously mixed with the test tube shaker for 30 seconds. It was then centrifuged at 1,000*g at 20° C. for 15 min. The supernatant was decanted. The centrifuge tube was then again weighed. The weight of the water-saturated sample was determined.

The fat-binding capacity of the cellulose-based fibers was determined at room temperature. For example, a 3 g aliquot was dispersed in a graduated 25 ml centrifuge tube in 20 ml of oil (commercial corn oil). The mixture was then centrifuged at 700*g for 15 min. The volume of unbound oil was determined. The oil binding capacity is given in ml of oil/g cellulose-based fibers.

The hydratability of partly dried or dried fiber fractions was determined by adding 10 g of the material, preferably in the form of a powder or granules, in 100 ml of water (30° C., pH 7) and leaving it for 15 minutes. Subsequently, the mixture was agitated and representative samples were removed from the suspension to be examined for the presence of the qualifying feature (QM) as follows: 1. Microscopic smear preparation: QM: complete separation of cellulose-based fibers and the absence of adhesions of constituents, 2. fiber analysis by means of a fiber analyzer (FiberLab FS300, Valmet). QM: presence of corpuscular (3-dimensional) fibers with a maximum extension of <2,000 µm, 3. sensory QM: absence of graininess. Complete hydration of cellulose-based fibers was present when the QM were met.

All investigations were carried out under normal pressure conditions (101.3 Pa) and at room temperature (25° C.) unless otherwise stated.

Example 1

Investigation of Unlocking Processes for the Recovery/Obtainment of Cellulose-Based Fibers For each 1 kg of A) rapeseed press cake, B) corn grits, C) whole soybeans, D) sugar beet pulp after extraction of molasses, the following tests were carried out:

Aqueous unlocking by placing materials A) and B) in a bath of the unlocking compounds at a temperature of a) 25° C. and b) 60° C. for 60 minutes each under continuous stirring; disintegration of materials C) and D) inserted in the unlocking solutions in an autoclave at 125° C. for 15 minutes. The following were used as unlocking solutions: 1.) water, 2.) 0.1 N sodium hydroxide solution, 3.) aqueous solution of arginine 0.3 molar, 4.) aqueous solution of lysine 0.3 and glutamine 0.2 molar, 5.) 30% sulfuric acid solution, 6.) 15% solution of sodium bisulfite with NaOH at pH 10, 7.) 25% solution of SDS.

Subsequently, the free liquid was removed from the resulting mixtures by centrifugation, so that a dimensionally stable mass was obtained. To separate dissolved constituents, the masses were solved/suspended in 10 l of water and finely dispensed with a mixer for 10 minutes. Subsequently, a separation of the water phase was carried out by a vibrating screen with a screen mesh size of 100 µm. From the fractions obtained, samples were taken for analysis. The drip-free masses were weighed and then dried in a drying oven. From the weight difference between the wet and dried mass, the water binding capacity was calculated. The wet samples were analyzed microscopically for the structure of the cellulose-based fibers and the degree of caking/clumping with other organic components. The resulting dry material was analyzed for the content of readily soluble carbohydrates and proteins (see example methods). The number of cellulose-based fibers (pcs) per gram of wet mass, the maximum volume and the aspect ratio were analyzed with a fiber analyzer (FiberLab FS300, Valmet).

Results:

An unlocking of the starting materials by water could not be achieved. With a base (2.) a partial unlocking of the starting materials A) and B) at room temperature was possible, but not with the unlocking solutions 5-7. An unlocking to a large extent could be achieved with the unlocking solution 2. at elevated temperature (A) b) and B) b)) and thermal disintegration (C) and D)). At elevated temperature or disintegration, the degree of unlocking was low to moderate when unlocking solutions 5-7 were used. Unlocking solutions 3 and 4 provided complete unlocking and decompaction under all experimental conditions. Microscopically, the methods in which macroscopic complete dissolution of soluble constituents had not been achieved showed the presence of solid particles and/or fiber structures that were partially trapped by other organic compounds or components as well as the presence of aggregation with other fibers structures or organic compounds. Furthermore, such cellulose-based fibers aggregates formed very large and compact structures. In the chemical analysis, soluble carbohydrates and proteins were detected in the sieve residue, thus, indicating macroscopically incomplete unlocking. In the unlocking experiments, which were carried out with unlocking solutions 3 and 4, microscopically complete separation of soluble constituents was present in all experimental procedures (the filtrate solutions passed through a sieve with a sieve mesh size of 20 µm without residue formation), thus allowing decompacted cellulose-based fibers to be obtained.

The volume of drip-free masses obtained after treatment with unlocking solutions 3 and 4 was significantly greater than the volumes of unlocking masses after the other unlocking procedures. Accordingly, the water binding capacity was significantly lower (80-190% by weight) after these processes than in cellulose-based fibers obtained with unlocking solutions 3 and 4 (680-850% by weight). Correspondingly, it was found in the chemical analyzes that in the mass of cellulose-based fibers obtained after use of the unlocking solutions 3 and 4, a residual content of readily water soluble carbohydrates of <1 Gew % and of proteins of <0.5 wt % was present. In the other unlocked products, the levels of readily soluble carbohydrates and proteins were between 15 and 37% by weight. The dried preparations with a residual content of readily soluble carbohydrates and proteins of >2% by weight were very hard and could not be ground to a fine powder. The solubility in water was minimal, only a small number of isolated cellulose-based fibers were detected in the dissolving liquid.

In contrast, the preparations which had been obtained after drying of product from unlocking solutions 3 and 4 could be milled to a fine powder. The resulting powder was easily solved/hydrated in water to yield a soft mass upon separation of unbound water. The analysis of the dimensions and number of cellulose-based fibers obtained from an unlocking process with unlocking solutions 3 and 4 showed a broad and uniform distribution of isolated fibers in a range between 20 µm and 600 µm with the number of fibers ranging from 550 to 237 pcs/g and an aspect ratio of 2.5:1 to 22:1. The fiber length weight was between 0.8 to 2.5 mg/100 m.

Example 2

Investigation of the Production of Cellulose-Based Fibers by Mechanical Disintegration For the experiments, 1 kg of each of the following starting materials were used: A) soybean meal, B) oat flakes, C) grape seed flour.

The following process steps were carried out:

V1) Milling of the starting materials to a mean grain size of 100 μm. This was followed by air classification with a fine classifier (Netsch CFS 5);

V2) milling of the starting products to a mean particle size of 100 μm. This was followed by addition to an aqueous solution in which the following compounds were present in dissolved form: a) arginine 0.2 molar, b) histidine and lysine in each case 0.1 molar, c) polyarginine 0.1 molar and glutamic acid 0.1 molar, d) $NH_3$.0.2 molar, e) KOH, 0.2 molar, f) urea 0.3 molar, for all in a weight ratio of 1:3, so that the starting material was completely immersed in the aqueous solution for 4 hours. Then the entire reaction mixture was rinsed with water in a volume ratio of 1:10 using a hand blender. The suspension was passed through a screen with a sieve mesh size of 200 μm. The sieve residue was rinsed twice with the same volume of a water phase and the sieve residue was then rolled out on a porous PP film in a layer thickness of 1 mm and dried. Subsequently, the dried masses were ground.

V3) The starting materials are added to the following aqueous solutions in an uncrushed form: a) arginine 0.3 molar, b) polylysine 0.2 molar, c) polyglutamate 0.2 molar and histidine 0.4 molar, d) triethylamine 0.2 molar, e) NaOH, 0.2 molar, f) urea 0.3 molar. The addition volume of the aqueous solutions was chosen so that complete wetting of the starting material had just occurred. The batches were allowed to stand for 24 hours. Then the mixtures were admixed in water in a volume ratio of 1:10 and mixed with a hand blender. Thereafter, the suspensions were passed through a sieve with a sieve mesh size of 100 μm. The sieve residues were rinsed out twice with the same volume of a water phase and were then rolled out on a porous PP film in a layer thickness of 1 mm and dried. Subsequently, the dried masses were ground.

Of the dry masses respectively obtained, chemical analyzes were carried out on the content of readily soluble carbohydrates and proteins (according to Example 1). For this, 50 g of each powdered fiber mass was hydrated in 500 ml of water at a temperature of 30° C. with continuous stirring for 1 hour. Then, 100 ml was filled into a narrow-base graduated cylinder and the sedimentation (settling) time in which the visible fibers had fallen below the 50 ml mark was determined.

Furthermore, samples were taken for an analysis of the cellulose-based fiber dimensions (analysis according to Example 1). The remaining suspension was concentrated (dewatered) so that a residual moisture of 20-30% by weight was obtained. The resulting paste-like masses were tasted by 4 experts. The following properties were assessed: (intrinsic) taste, graininess, mouthfeel, sensation during swallowing.

Results:

The fiber fractions of unlocking study V1 still contained larger amounts of readily soluble carbohydrates (24-36% by weight) and proteins (18-29% by weight), which were present in compacted form. The fiber masses of unlocking studies V2 and V3 prepared with unlocking compounds a)-c) had residual levels of readily soluble carbohydrates and proteins of <0.5% by weight. After use of the compounds d)-f) for unlocking, contents of readily soluble carbohydrates of 12-22% by weight and of proteins of 14-25% by weight were contained in the resulting fiber masses. The fiber fraction, which had been obtained from unlocking study V1, could only be partially rehydrate after drying and there was a very rapid sedimentation after being added to the measuring cylinder. The powdered fiber fractions prepared from unlocking studies V2 with the unlocking compounds d)-f) were partially hydrated sufficiently, while in case of the powdered fibers of the unlocking experiment V3, which were carried out with the unlocking compounds d)-f), only small proportions were hydrated. The determined sedimentation time at V2 was 15-25 minutes and at V3 4-10 minutes for unlocking products obtained with these unlocking compounds. In contrast, complete hydration of the powdered material of unlocking experiments V2 and V3 carried out with the unlocking compounds a)-c) was registered. The solvated (hydrated) cellulose-based fibers of these unlocking fractions showed a very low sedimentation rate in a measuring cylinder, so that solvated cellulose-based fibers had settled to below the 50 ml mark only after 12 to 27 hours. The fiber length averaged between 150 and 300 μm, the fiber diameter was between 11 and 19 μm. The fiber length weight was between 1.2 and 5.1 mg/100 m.

The tasting of the wet fiber material from unlocking study V1) revealed that there was a considerable load of aroma and flavoring substances which corresponded to those of the starting materials. The fiber fraction from unlocking studies V2 and V3, which were carried out with unlocking compounds d)-f), also showed, albeit to a lesser intensity, aroma and flavor of the starting material. However, they were inedible due to an intense smell or taste of the unlocking compound that have been used. In contrast, in the fiber fractions from unlocking studies V2 and V3 obtained with the unlocking compounds a)-c), no aroma or flavors were present, so that the smell and taste were judged neutral. Furthermore, cellulose-based fibers which had been obtained in the experiments V2 and V3 with the unlocking solutions a)-c) had no graininess, a pleasant mouthfeel and a pleasant sensation during swallowing.

Example 3

Investigating on the Disintegration of Plant Material to Obtain Cellulose-Based Fibers In each case, 4 kg of the following starting materials were used for the investigations: 1. squash (butternut), 2. carrots, 3. celery, 4. soy kernels. The materials 1-3 were divided into 1-2 cm thick slices or pieces. In each case half of the starting materials were disintegrated together with 1.5 l each of the following unlocking solutions in an autoclave in series 1 over 15 minutes at 121° C. and in series 2 over 5 minutes at 140° C., then samples were taken for the analysis. In experimental series 1.1 and 2.1, a thermal disintegration was first carried out by performing the same experimental procedure with water as in experiment 1 and 2. The softened masses obtained from test series 1.2 and 2.1 were freed from dripping water and samples were taken for analysis and then added in an equal weight ratio to the different unlocking solutions and mixed herein with a hand blender for 5 minutes.

The following unlocking solutions were used: a) water, b) sodium hydroxide 0.2 molar, c) urea 0.2 molar, d) arginine 0.2 molar, e) polylysine and histidine 0.2 molar, f) arginine 0, 1 molar and sodium sulfite 1% by weight. The soft masses obtained after the thermal disintegration of test series 1 and 2 were, together with the residual water, were mixed with water in the ratio 1:3 and mixed with a mixer for 5 minutes. The hydrated homogeneous mixtures were filtered to remove free water, which was done immediately in test series 1 and 2 and after 4 hours in test series 1.1 and 2.1, respectively, with a chamber filter press, so that a residual moisture of the condensates between 70 and 90% by weight was achieved. These were suspended/dispensed in a weight ratio of 1:10 with water with the mixer for 2 minutes, so that a finely divided suspension was present. This was passed through a purée sieve. The permeate was concentrated by means of a fine sieve (sieve mesh size 100 µm) and further condensed to a residual moisture content of 70% by weight. The same was done with the filter residue. From the fractions obtained, analyses were carried out to determine the content of readily soluble carbohydrates and proteins (according to Example 1). Furthermore, tasting according to Example 2 was carried out.

Results:

In all investigations of the test series 1 and 2, in which pure water had been used as the unlocking solution, large aggregates were still present, which could not be divided/dispensed by the subsequent dispensing process. The passage through a purée sieve was then only partially possible and with low yield. The amount of the fiber fractions that could be separated by passing the material through a purée sieve was significantly lower for the samples obtained with the unlocking solutions b) and c) than was the case for the samples obtained with the unlocking solutions d)-f). Correspondingly, the amount of filter residues when using the unlocking solutions b) and c) was greater than when using the unlocking solutions d)-f). Correspondingly, both, the fiber fractions of the permeate and the solids in the filter residue, contained more soluble carbohydrates and proteins using unlocking solution b) or c) (12.5 to 27.8% by weight) than was the case when unlocking solutions d)-f) were used (0.1-0.4% by weight).

A similar result was found in the analysis of the experimental series 1.1 and 2.1. When using unlocking solutions b) or c) soluble carbohydrates and proteins were present in significantly higher concentrations (16.2 to 37.2% by weight) than was the case when using unlocking solutions d)-f) (0.2-0.5 wt %). In the latter, the maximum lengths of the cellulose-based fibers averaged between 180 and 350 µm, the minimum diameter between 12 and 21 µm. The fiber length weight was between 1.0 and 5.4 mg/100 m.

The tasting of the cellulose-based fibers obtained from the permeate showed that in all test series samples which had been obtained with unlocking substances d)-f) were virtually odorless and tasteless, while the other samples had a characteristic (intrinsic) odor and taste. In addition, the samples obtained with the NaOH solution had a soapy taste. The average diameters the cellulose based fiber-fraction present in the permeate when using unlocking solutions b) and c) were in the range from 500 to 850 µm (range 10 µm to 2200 µm) and those after using unlocking solutions d)-f) were between 250 and 350 µm in a range between 10 and 1,800 µm. There was no relevant difference between the dimensions the cellulose based fiber-fraction of test series 1 or 2 and 1.1 or 2.1 after use of unlocking solutions d)-f), while measured dimensions tended to be larger after the use of unlocking solutions b) or c). In f), the obtained cellulose-based fibers were brighter than those of the other fiber masses.

Example 4

Production of Cellulose-Based Fibers by Unlocking Compounds

For each study, 500 g of the following starting materials were used: 1) rapeseed press cake, 2) soy press cake, 3) jatropha press cake, 4) carrots, 5) pumpkin, 6) celery. The unlocking solutions used were: a) arginine 0.1 molar, lysine 0.1 molar, glutamic acid 0.1 molar; b) polylysine 0.3 molar, c) arginine 0.3 molar; d) histidine 0.2 molar, lysine 0.1 molar, valine isoleucine peptide 0.2 molar.

The starting materials were treated according to one of two routes:

Route A) Loading the starting materials 1)-3) into one of the unlocking solutions in a weight ratio of 1:1.5 over 4 hours at 25° C. Thereafter, the mass was dispensed in tap water in a weight ratio of 1:8 by means of a colloid mill with which an intensive mixing was carried out for 5 minutes. The mixture was then placed on a vibrating sieve with a sieve mesh size of 200 µm and the sieve residues were separated and condensed with a filter press to a residual moisture content of 70 to 90% by weight. The resulting press residue was then suspended and dispensed twice in a 1:10 weight ratio in tap water for 3 minutes, and then as described before was first dehydrated with the vibrating screen and then with the filter press.

Route B) Loading starting materials 4)-6) chopped into 2 cm thick pieces into the unlocking solutions in a weight ratio of 1:0.8 in a container placed in an autoclave. This is pressurized to 1.8 bar and heated to 125° C. for 5 minutes. Then removal of shell/membranous portions in the materials 5) and 6). A free water phase is removed by means of a vibrating screen. The sieve residues are intensively dispensed by mixing in a weight ratio of 1:10 in a water tap by means of a colloid mill for 5 minutes. The individual mixture was then placed on a vibrating screen having a sieve mesh size of 200 µm and the sieve residues were separated and dewatered with a filter press to a residual moisture content between 70 and 90% by weight. The resulting press residue was then suspended and dispensed twice in a 1:10 weight ratio with tap water with a hand blender for 3 minutes, and then dewatered first with the vibrating screen and then with the filter press, as previously described.

From the cellulose-based fiber masses obtained, samples were taken for the determination of readily soluble carbohydrates and proteins (determination according to Example 1) and for the determination of the number of cellulose-based fibers and their dimensions (analysis according to Example 1). Furthermore, samples were taken to examine the sensory properties. The investigations were carried out immediately after the obtainment of the cellulose-based fibers and after a 3-week storage at 6° C. The sensory evaluation was carried out by 4 experts, among others, for the following properties: sensory taste neutrality, softness in chewing, mouthfeel, sensation during swallowing.

Results:

By using the unlocking solutions, without any simultaneous disintegration of the starting material, cellulose-based fibers could be obtained from all starting materials and freed from the other constituents of the starting materials. Thus, between 0.1 and 0.3% by weight of soluble carbohydrates and between 0 and 0.3% by weight of proteins were detected in the resulting cellulose-based fiber fractions. The dimensions of the cellulose-based fibers obtained from route A) tended to be slightly larger than those obtained from the process of route B) (mean maximum diameter 120 µm to 360 µm vs. 40 µm to 290 µm; distribution of maximum diameter between 20 µm and 1480 µm vs. 10 µm and 980 µm). The fiber length weight was between 0.8 and 3.1 mg/100 m. All obtained cellulose-based fibers were sensorially evaluated as to be neutral, that is odorless and tasteless. There was also no difference for the perceived softness of the cellulose-based fiber masses during chewing, which was rated very soft in all fractions. The mouthfeel produced by the obtained cellulosic-based fibers was rated as very good in all fractions. Even when swallowing the cellulose-based fibers produced, there were no unpleasant impressions. The results of the evaluation of the samples after a long-term storage was virtually unchanged from the initial assessment.

Example 5

Process for Purifying Cellulose-Based Fibers.

Here, 1 kg of each kernels, fruits and vegetables, which were not or no longer suitable for use in food was used: 1) moldy carrots, 2) apples with fouling, 3) softened avocado with putrid smell, 4) Jatropha nuts after aging for several years with a rancid odor.

The materials according to 1) to 3) were first placed in a disinfecting bath (DMSO 10% by weight, ethanol 20% by weight) for 2 hours and then rinsed with water. For all materials wet grinding was carried out with a colloid mill by adding one of the following unlocking solutions in a volume ratio of 2:1:a) arginine 0.1 molar, leucine-alanine 0.1 molar; b) histidine, poly-arginine; c) lysine 0.2 molar, valine 0.1 molar, glutamine 0.1 molar; d) arginine 0.1 molar, lysine 0.1 molar, leucine 0.1 molar; e) NaOH 0.1 normal; f) $H_2O$. The suspensions were fed to a purée sieve to separate uncut materials having a particle size of >5 mm. The permeate was placed in an autoclave and disintegrated at 120° C. and a pressure of 2 bar for 6 to 10 minutes. Subsequently, the resulting masses were homogenized in a ratio of 1:3 (v/v) with water by means of a shear mixer for 2 minutes. The viscous suspensions obtained were filled in PP filter cloths and squeezed out in a chamber filter press under a pressure of 400 kg/m$^2$ for 5 minutes. Subsequently, the filter residue was homogenized twice with a dispensing volume of 6 liters each with the blender and dehydrated as before with the filter press. The obtained cellulose-based fiber material was taken for analysis of the cellulose-based fiber dimensions and cellulose-based fiber length weight (according to Example 1), the content of proteins and readily soluble carbohydrates (according to Example 1) as well as for a culture to determine a microbial colonization.

Results:

The obtained cellulose-based fiber fractions after use of the unlocking solutions a) to d) had a mean diameter of 150 µm to 400 µm of the individual cellulose-based fibers, with a distribution between 105 µm and 1,500 µm. The fiber length weight was between 1.4 and 3.9 mg/100 m. Levels of protein and soluble carbohydrate contents were determined to be <0.5% by weight. In contrast, the mean diameter of the fiber material received when using the unlocking solutions e) and f) was 850 µm or 1,200 µm at a distribution between 150 µm and 3,400 µm. In those the contents of readily soluble carbohydrates and proteins were between 12 and 35% by weight. The microbiological investigations showed that no growth of bacteria or fungi occurred in all samples obtained with the unlocking solutions a) to d) within an observation period of 2 weeks. On the other hand, starting materials 1 and 2 treated with the unlocking compounds d) and e) exhibited mold formation, and in the starting material 3 putrefaction bacteria could be detected, and further, preparation 4 had a rancid odor. This was not the case for the cellulose-based fibers obtained with the unlocking solutions a)-d).

Example 6

Investigation of Production of Cellulose-Based Fibers from Disintegrated Plant Material The following plant-based products were tested for the obtainability and production of cellulose-based fibers which are odorless and tasteless: A) vegetables: celery, cauliflower (BK), carrots (RR), pumpkin (K); B) Fruits: Apples (Ap), Quinces (Qu).

The starting materials were roughly cut and softened in a water bath for 30 minutes to 2 hours at 90-95° C., so that the fragments could be mashed with fingers. Peels, seed coats and husks were then removed and the still hot fragments minced with a shear mixer (Ultrathurrax 25T, Germany) for 2 minutes at 10,000 rpm. Thereafter, addition of tap water in a ratio of 8:1 to 12:1, then re-homogenization with the shear mixer for 5 minutes was performed. After that, water was removed by means of a chamber filter press. Then 300 g each of the resulting compositions having a residual moisture content of <80% by weight were mixed with 500 ml of each of the following solutions with the shear mixer as described above: 1) water, 2) arginine 0.3 molar, 3) lysine and histidine 0.3 molar, 4) arginine, lysine-glutamine 0.3 molar, 5) lysine-alanine, benzylglutamate 0.3 molar, 6) SDS 0.3 molar. After 3 hours, the mixtures were each mixed with water in a ratio of 1:8 to 1:15 with the shear mixer and then dewatered with the chamber filter press. The dispensing process was then repeated. Subsequently, samples were taken for analysis and tasting. The remaining mass was placed and spread on screen plates and dried at 60° C. for 2 hours. The resulting dry masses were finely ground with a cone mill. Finally 10 g of each of the resulting powders were subjected to solution (hydration) experiments by placing them in 200 ml of cold water in a tall beaker. In the central area of the beaker was a propeller stirrer, which slightly agitated the liquid at 50 rpm. The time until no solid on the glass bottom was recognizable was determined. The stirring was then stopped and the time determined until no cellulose-based fibers were detectable above the 120 ml mark of the liquid column. Subsequently, the cellulose-based fibers were dewatered by means of a filter press to a residual moisture content of 70-80% and tasted. The tasting included an odor and taste test by 4 experts. They performed a sensory examination on, among others, taste neutrality, softness, mouthfeel and sensation during swallowing.

Results:

The preparations prepared with unlocking solutions 1 and 6 had very low and greatly retarded solubility (solvability) as well as a faster settling rate than was the case with dried and ground cellulose-based fibers prepared with unlocking solutions 2-5. During the tasting, the cellulose-based fibers produced by the unlocking solutions 2-5 had consistently complete taste neutrality and had a high degree of perceived softness, a pleasant mouthfeel, and an undisturbed sensation during swallowing. In the fractions prepared with the unlocking solutions 1 and 6, there were a characteristic (intrinsic) taste and smell, and there were significantly lower ratings for softness and mouthfeel than in the evaluation of the cellulose-based fibers prepared with unlocking solutions 2 to 5. Furthermore, by swallowing of preparations 1 and 6 there was a scratchy feeling in the throat.

Example 7

Investigation of the Surface Coatability and the Establishment of a Surface Functionalization Layer in Cellulose Fibers and Cellulose-Based Fibers.

Cellulose fibers derived from the husks and stems of wheat (WF) and bamboo (BF) and having a fiber length of <75 µm as well as cellulose-based fibers from soybeans (SK), rapeseed press cake (RPK) and apples (AF) obtained according to the preparation process of Example 4 and ground to a fine flour after complete drying were used. Samples of each of the powdered fibers were reserved for analysis and 2 g from each were added to 50 ml of an aqueous solution of A) polyethersulfone (10%), B) PEG 200 (15%), C) sodium lauryl sulfate (2.5%), D) a nano-emulsion of arginine 0.2 molar and oleic acid 0.1 molar and E) water and stirred for 3 hours. Subsequently, the fiber masses were separated from the solutions by means of a fine sieve and dispersed twice in water for 5 minutes and then dewatered. Finally, they were dried in a vacuum oven at 45° C. for 48 hours. The resulting dry masses were re-ground and then split into fractions which, like the reserved samples of starting materials, were placed in fluorescent dye solutions having a hydrophilic (green fluorescent protein (GFP)) or hydrophobic (Nile red) compound hydrated/solvated therein for 2 hours and then abundantly rinsed with water. The binding of the fluorescence markers was quantified by means of a suspension of the labeled fibers by means of a flow-through fluorescence analyzer and normalized to the detected particle number.

Results:

The investigated cellulose-based fibers had a higher coverage rate for the hydrophilic as well as for the lipophilic fluorescent dye, as was the case for the uncoated cellulose fibers (SK+160%, RPK+180%, AF+120%) before the surface coating was performed. After surface modification, there was a marked increase in the surface coverage of cellulose-based fibers, which compared to cellulose fibers was greater by 360±35%, 220±40%, 420±41%, 680±23% for A), B), C) and D), respectively, for the lipophilic marker and was greater by 480±60%, 550±35%, 260±50% and 180±35% for A), B), C) and D), respectively, for the hydrophilic marker; in comparison to cellulose-based fibers that had not been surface-modified, there was an increase after surface modification of 120%, 100%, 240%, 310% for A), B), C) and D), respectively, for the lipophilic marker and by 250%, 320%, 140% and 90% for A), B), C) and D), respectively, for the hydrophilic marker.

Example 8

Investigation on the Production of Cellulose-Based Fibers from Organic Starting Materials.

The manufacturability of cellulose-based fibers which have a residual content of readily water-soluble proteins and/or carbohydrates which is <1% by weight and which do release any odorants, flavorings or colorants to an aqueous medium was investigated in variously pretreated starting materials.

Experimental series I. An organic mass was used in which cellulose-based fibers were enriched after extraction of soluble proteins that was obtained from soy beans and unpeeled kidney beans. For pre-processing, the soy beans or unpeeled beans had been mechanically comminuted and placed in a solution of poly-arginine and histidine, or lysine and polyglutamate for 4 or 8 hours. The organic mass, with a solids content of 40% by weight (dry weight), was suspended in water in a volume ratio of 1:10 or 1:5, followed by intensive mixing and finally filtration with a screen mesh size of 100 µm. The screen residue consisted predominantly of cellulose-based fibers, but larger aggregates of shell materials as well as complex organic components (starch) were included herein. The fiber masses were suspended in water in a volume ratio of 1:10 and transported by a pump through a hydrocyclone (Akavortex, AKW, Germany). The fraction from the upper outflow was collected and filtered (sieve mesh size 100 µm) by means of a bow sieve. The sieve residue was analyzed and used for the study.

Experimental Series II. Thermally disintegrated plant material, in which cellulose-based fibers were still combined into large aggregates, was used for the unlocking process. Here, the starting materials were quince, carrot and celery, which had been subjected to thermal treatment in a water bath at temperatures between 90° and 98° C. for 1 to 3 hours and comminuted with a hand blender to a homogeneous mass. In the analysis of the homogenate, aggregates of >2,000 µm were present in a proportion of >15% by weight. Furthermore, there was a characteristic (intrinsic) smell and taste. The masses were dewatered by means of a chamber filter press to a residual moisture content of 50-80% by weight. The resulting masses were suspended in a weight ratio of 1:5 in an aqueous solution containing a) arginine 0.3 molar, b), poly-lysine, urea 10%), c) arginine 0.1 molar+ $Na_2SO_3$ 1%; thereafter the suspensions were treated in an autoclave for 8 and 16 minutes at a temperature of 120° C. The resulting material of the unlocking process was filtered and exhaustively rinsed twice with water. From the final sieve residue, samples were taken for analysis.

Experimental Series III. Mechanically disintegrated plant material with a high proportion of colorants was unlocked. For this purpose, a puree of beetroot, the fiber fraction of an unlocking process of sunflower seed press cake with an arginine solution and the fiber fraction of an aqueous unlocking process of a maize meal were used. The starting materials were first dehydrated to a residual moisture content of 40 to 70% by weight. Then the masses were suspended in aqueous solutions containing a) poly-arginine, urea 5%; b) Lysine 0.3 molar, SDS 2%, histidine 0.3 molar; c) arginine 0.1 molar, DMSO 2%, in a weight ratio of 1:5 to 1:10 with a hand blender. The suspensions were stirred in a series of experiments (T60) for 24 hours at 60° C. and treated in another series (T120) for 8 minutes at 120° C. in an autoclave. The resulting suspensions were filtered and rinsed twice with water. From the final sieve residue, samples were taken for analysis.

The analyses carried out included the analysis of the size distribution of the cellulose-based fibers, the content of readily water-soluble proteins and carbohydrates (according to Example 1), investigations on the leachability of colorants (testing by incorporation of the test fraction in water and aqueous surfactant solutions for 48 hours with subsequent filtration and spectroscopic analysis of the filtrate) and a sensory evaluation by 4 experts according to the criteria of Example 4.

Results:

Experimental Series I: The cellulose-based fibers separable by means of a cyclone separation technique were virtually without visible or measurable residues of shell/seed coat materials or aggregates of other constituents of the starting material, e.g. of starch complexes. Furthermore, a selection of large-volume cellulose-based fibers were obtained, which had a narrower diameter spectrum than that which was present in the starting material.

Experimental Series II: The analysis of the obtained cellulose-based fibers showed that the treatment resulted in a comminution of complexes of cellulose-based fibers, by which the diameter spectrum had clearly shifted to the left, particles with a diameter of >2,000 µm were not present or in a proportion of <0.1%.

Experimental Series III: From the obtained masses of cellulose-based fibers of both test series T60 and T120 no colorants could be leached out by aqueous solutions.

The cellulose-based fibers obtained in test series I to III had a content of readily water-soluble proteins and/or carbohydrates of <0.1% by weight.

In all obtained cellulose-based fiber masses, the odor and taste neutrality were given in the as determined in the sensory examination. Furthermore, it was found for all preparations obtained that they are very soft in a masticatory process, convey a pleasant mouthfeel and that there is no malaise when swallowing the preparations.

Example 9

Investigation of the Colloidal and Emulsifying Properties of Cellulose-Based Fibers.

30 g each of the dried cellulose-based fiber of: peas (EF), oilseed rape (RF), carrots (KaF), oats (HF) and pumpkin (KüF), which are subjected to a separation or purification step with one amino acid and/or peptide solutions of the present invention, according to Examples 1-4 were prepared, and each 30 g of powder of plant cellulose fibers, prepared from husk and stem mass of oats (HC) and wheat (WC), with a fiber length of 90 µm and each of 3 g of hydroxymethylcellulose MHS 300,000 P4 and 90SH-100,000 were dissolved in 1 liter of tap water at 25° C. for 30 minutes under continuous stirring.

For comparison, the cellulose-based fiber-containing compositions of Examples 1-3 (RF-V, KaF-V, HF-V, KüF-V), in which the unlocking was not carried out with an amino acid and/or peptide solution, were performed in parallel. Immediately thereafter, at constant temperature, the viscosity of the suspension was determined 3 times with a viscometer (Krüss, Germany) and the mean was calculated. Thereafter, the water content of a 0.5 g sample was determined and it was suspended in a 100 ml Erlenmeyer flask containing 50 ml of distilled water. After agitation for 1 hour at 20° C., the free water phase is removed using a G3 glass frit; then, together with the glass frit, the sample material is centrifuged at 2,000 g for 15 min. The amount of centrifuged liquid and the sample weight are determined. The water retention value (WRR) was calculated as indicated under "Methods". The remaining mass was resuspended in tap water under agitation at 25° C. and agitation was paused every 5 minutes to determine the viscosity, this was done consecutively 4 times. Subsequently, the suspensions were filled into a graduated measuring cylinder. After 24 hours, the distance between the water surface and the water phase boundary layer in which a colloidal suspension was visible was determined (S24); the result was verified by turbidity measurements. Thereafter, the suspension was well mixed, and 5 ml of olive oil was added to 200 ml of the resulting suspension and stirred with a propeller stirrer for 10 minutes at 500 rpm at a temperature of 30° C. Subsequently, the time was determined in the stance phase, to which a phase separation began (S O/W).

Results (numerical results in Table 1):

Cellulose-based fibers obtained with the inventive separation or preparation processes with amino acid and/or peptide solutions showed very good hydratability which was comparable to that of hydroxy celluloses. While a highly viscous gelatinous solution was formed in cellulose preparations, hydrated cellulose-based fibers gave suspension with a low-viscosity. Cellulose-based fibers which had not been obtained with an amino acid and/or a peptide solution showed inadequate hydratability. Also cellulose fibers resulted in suspensions in water, but the fibers settled rapidly. The cellulose-based fibers produced according to the invention resulted in a higher viscosity of the suspensions than cellulose fibers and cellulose-based fibers which had not been treated with the amino acid and/or peptide solutions. The water retention capacity could not be determined for the cellulose preparations due to the method. The WRR was significantly higher in the cellulose-based fibers produced according to the invention than in the cellulosic fibers and also greater than in cellulose-based fibers which had not been produced according to the invention. The restoration of the colloidal properties could be achieved with the cellulose-based fibers produced according to the invention just as quickly as with hydroxy-celluloses; however, in the cellulose fibers and in cellulose-based fiber material not produced according to the invention, a much longer time was required. In cellulosic fibers and cellulose-based fibers material that were not produced according to the invention, a phase separation occurred very rapidly after mixing with a lipophilic phase, while a mixture that was stable for the longest time was achieved with the cellulose-based fibers produced according to the invention.

Example 10

Investigations on the Surface Coverage (Adherence) of Microorganisms and Compounds as Well as their Long-Term Stabilization.

Cellulose-based fibers that were dried (TB) and those containing a residual moisture of 50 wt % (NB) of soybean (SF) and beans (BF), which were prepared according to example 1 (arginine process c)) 4 (in which amino acid and/or peptide solutions have been used) were suspended in water and mixed with baker's yeast (BH), a sourdough kit (ST) containing, among others, *Saccharomyces cerevisiae*, *Lactobacillus plantarum* and *Lactobacillus brevis*, and further with a solution of dissolved sodium bicarbonate (NHC) and stirred at 25° C. (BH+ST) or 10° C. (NHC) for 2 hours (coating A). Subsequently, the cellulose-based fibers were dewatered with a chamber filter press to a residual moisture content of between 40 and 50% by weight. Thereafter, the fiber masses were suspended in various solutions (coating B): 1) vitamin C 10% by weight, 2) citric acid 10% by weight, 3) oat protein concentrate (60% by weight) 10% by weight suspension, 4) soy protein isolate (90 wt %) 10 wt % suspension with glucose 3 wt %, and stirred for 10 minutes at 10° C. Then the cellulose-based fiber fractions were dewatered using a filter press. The same treatment procedure was carried out with cellulose fibers made from a milling of oat (HC) and bamboo (BC) stalk and husk material and having a fiber length of 75 µm. The still wet fiber masses were each spread on a vibrating screen. During the drying process, the vibration function was activated and warm, dry air (40° C.) was passed through the screen from below. Particles smaller than 200 µm that passed through the screen were collected. A sieve residue remaining after complete drying was ground with a disk mill to a particle size of <100 µm. The respective sieving and milling fractions were combined and separated, after which they were sorted out by a sieve with a screen size of 100 µm. All fiber materials were sampled for chemical and microscopic analysis.

Baking tests were carried out with cellulose-based fibers coated with BH (test series 1), ST (test series 2) and NHC (test series 3).

Test series 1: In each case 50 g of the individual preparations were placed in a mixture of 50 ml of water and 50 ml of milk with 2 g of sugar at a temperature of 25° C. for 1 hour and occasionally stirred. The suspensions were each added with 200 g of a wheat flour and 1.5 g of salt and kneaded into a homogeneous dough and formed into rolls. The baking process was started after the dough was allowed to stand for 2 hours and all samples were prepared using the same conditions.

Test series 2: In each case 100 g of the individual preparations were placed for 2 hours in 150 ml of water at a temperature of 25° C. Each mass was added to 250 g of a bread flour mixture and 2 g of salt and kneaded into a homogeneous dough and formed into a loaf of bread. The baking process was started after 24 hours and carried out for all samples under the same conditions.

Test series 3: 10 g each of the individual preparations were mixed with 250 g corn flour, 10 g sugar, 1 g salt and then 250 ml milk, 1 egg and 40 g butter were incorporated, so that a viscous homogeneous dough was formed, which was filled into molds. The baking process was started after 10 minutes and carried out for all samples under the same conditions. To obtain reference preparations, the test series were also carried out with yeast (VS1), sourdough (VS2) and NHC (VS3) instead of the preparations using cellulose-based fibers. After cooling the bakery samples were measured and the baking volume (BV) was determined, then the surface condition (crispiness, surface area texture) (OFB) and resistance to indentations (EDS) was determined, then the baking samples were diced and the fineness and distribution the entrapped air chambers was determined then (LEK). The quantitative measurements were set in relation to the results of the reference baking samples and are given as relative values in Table 2. Finally, there was a taste testing by 4 experts, who judged, among others, the chewiness, the fineness of the chewed material and the mouthfeel as rated on a scale from 1 (very low/very bad) to 10 (very high/very good). The medians of the evaluations of the bakery samples are given in Table 2 (SBW). The same evaluation was made on the baking results made with the identical preparations, which were stored under exclusion of air for 2 months.

Results (numerical results in Table 2):

Microscopically, it was possible to document a high adhesion density of the yeasts and bacteria in and on the cellulose-based fibers coated with the different methods. In contrast, cellulose fibers showed only a low amount of adhering yeasts and bacteria on the surfaces. The chemical analysis showed that cellulose-based fibers had absorbed more sodium bicarbonate than cellulose fibers. The baking samples made with the cellulose-based fibers were easy to process into a soft dough, which is not the case with cellulose fibers. Baking results with cellulose-based fibers of Test Series 2 and 3 exhibited less sticking to the baking pan than was the case for the reference samples or those baked with cellulose fibers. In the baking trials, using cellulose-based fibers, there was a significantly greater baking volume and a more homogeneous distribution of the air chambers than the reference bakery results, as well as found in baking results made with coated cellulose fibers. Also, the sensory and physical properties of the baking results made with coated cellulose-based fibers were better or comparable to those of the reference samples and significantly better than the baking results made with coated cellulose fibers.

With the preparations of coating B, the same baking tests were carried out after 2 months under dry storage conditions. It was shown that compared to coating A of cellulose-based fibers there was virtually no difference in the quantitative and qualitative assessments of the baking results. In contrast, the quantitative and qualitative baking results of cellulose fibers made 2 months after coating B were worse than those achieved with coating A.

Example 11

Studies on the Fermentative Activity of Microorganisms on/in Cellulose-Based Fibers and Cellulose Fibers.

Cellulose fibers from the corn (MF) and wheat (WF) stalks with a fiber length of 100 μm as well as cellulose-based fibers from kidney beans, jatropha and pumpkin, which were prepared according to Example 4, were used for the investigations.

For loading with microorganisms, in each case 2 g (dry weight) of the fiber masses was suspended in aqueous suspension in which A) *Lactobacillus gasseri*, B) *Bifidobacterium longum* or C) baker's yeast were suspended in a cell count of 500,000/ml for 2 hours in an agitated bath at 30° C. Subsequently, filtration of the pulp masses was done with a 100 μm sieve mesh size and then the filter residues were pressed to a moisture content of 70-80% by weight. After that, the fiber masses were again suspended in 500 ml of water twice and each time re-filtration and dewatering of the residue was performed. Finally, drying of the resulting fiber mass after being spread onto a filter cloth in a drying oven at 40° C. After drying, the coherent aggregates are comminuted by grinding with a grinding mill to form particles of <0.3 mm. In each case 1 g of the ground fiber materials are added to the following nutrient media: skimmed milk for the preparations having been exposed to (loaded with) A) and B) and a glucose solution for preparations loaded with C). The suspensions were stirred continuously at 30° C. For process control, the pH of the suspensions was monitored and the values determined after 1 and 3 hours. As a reference experiment, a suspension containing the same number of the microorganisms as had been used to load the fibers was added to the nutrient media in a series of experiments. The course of the pH measurement result was used as the reference value and the pH values obtained with the fiber preparations were set in relation herewith.

Results:

Compared to the enzymatic activity of microorganisms added directly to a nutrient solution, the enzymatic activity of the microorganisms which had been loaded (adhered/incorporated) onto/into the cellulose-based fibers developed differently over time, with the activity after 1 hour being between 55% and 75% of the activity of the reference experiment and after 3 hours being between 180% and 240% of the activity in the reference experiment. For cellulose fibers (MF and WF) which had been subjected to a similar loading of microorganisms, the activity of the microorganisms was between 22% and 35% after 1 hour and between 60% and 75% after 3 hours as compared to the reference tests.

Example 12

Studies on the Formulation and Stability of Protein Preparations with Cellulose-Based Fibers.

For the investigations, the following carrier materials (TM) were used: cellulose-based fibers of soybean (SF), sunflower (SBF) and pumpkin (KF), prepared according to Example 4, as well as cellulose fibers from wheat hulls (WF) and methylhydroxypropylcellulose and hydroxyethylcellulose (MC 1 and MC2). These were loaded with the following protein concentrates (PK) (protein content): soy protein (SP) (80% by weight), rapeseed protein (RP) (60% by weight) and milk protein (MP) (90% by weight). The PK of RP and SP had been prepared by an unlocking process in which the press residues were unlocked with an arginine solution after oil extraction with a screwing press and then dispensed in an aqueous dispensing phase. After separation of the solids with a vibrating sieve (cascade filtration using a 200 µm and 20 µm sieve mesh size), the protein-containing permeate was treated with an organic acid (including citric acid), resulting in an aggregation of proteins, which were obtained by filtration and then freed from free water up to a residual moisture content of 50-70% by weight, so that a spreadable material was obtained. Part of the protein fraction thus obtained was spray-dried which then had a powdery consistency. The MP corresponded to a commercially available powdered milk protein concentrate.

The combination of the TM with the PK was carried out according to the following modalities: 1. TM with a moisture content of 70-80% by weight and PK with a residual moisture content of <5% and 2. TM with a residual moisture content of <5% by weight and PK with a moisture content of 80-90% by weight are kneaded together. Dry weight ratios of 1:5 (TM:PK) were used in all approaches. The substances were mixed by means of a kneading/stirring device until a fine-to-coarse-grained mixture having a residual moisture content of <40% by weight was obtained. This was dried at a temperature of 50° C. until a residual moisture of <8% by weight. This was followed by fine grinding with a grinding mill. From the obtained powdered mixtures, samples were taken for analysis. This included a microscopic examination as well as investigations on the hydratability of the solids and the colloidal properties. Furthermore, food preparations were prepared from the resulting mixtures of substances and their physical and sensory properties were evaluated. The following dishes and their preparation were prepared/carried out: A) patty: broth and spices dissolved in water were added to the powdered preparations (80 g per serving) in an amount of aqueous broth that was required to give a homogenous mixture when mixed to produce a soft, non-sticky and malleable mass; B) Cheesecake: 300 g of the powdered preparations plus 200 g of sugar and flavors and lemon juice were mixed by means of a stirrer with a quantity of water which allowed an easily stirrable homogeneous dough to be obtained. Egg white that had been whipped was folded into the mixture to obtain a dough, which was then filled into a shortcrust pastry form (preparation according to Example 16); C) Foam cream: to 50 g of the powdered preparations, water in which sugar, vanilla sugar, and vanilla flavor were dissolved, was admixed in an amount until a readily flowable homogeneous mass was formed, followed by homogenization with a hand blender until a foaming mass had formed. After that, steam was introduced into the foam mass until a stable mass was obtained.

The preparations A) and B) were cooked under standardized conditions, preparation A) was tasted in the heated state, preparation B) in the cooled state after 6 hours and preparation C) was tasted immediately after receipt by 4 experts who rated, among others, the following properties on a scale from 1 (very poor/low) to 10 (very good/much): for A): product cohesiveness (PZ), chewability (Z); for B) product cohesion (PZ), stickiness (K); for C) creaminess (S), fattening sensation (M); all products were evaluated for sensory impressions such as granularity/graininess (FK) and mouthfeel (MG).

Each 100 g of the powdered preparations was stored under exclusion of air for 6 and 12 months and then examined for microbial colonization, as well as the physical properties (e.g. consistency, flowability) and the water absorbency, the later were compared with those that had been documented for the preparations immediately after production. Furthermore, preparation experiments were repeated with the stored samples.

Results (excerpts of the numerical results of the sensory evaluation are shown in Table 3): It was not possible to mix either of the cellulose preparations and the protein preparations with any of the two modalities to a uniform mass; there was formation of lumpy inclusions, which could only partially be dissolved by adding a large volume of fluid and a long exposure duration; therefore the planed subsequent investigations were not carried out.

In the analysis of the powdered preparations obtained, the following fractions of the compositions were determined: protein content 58 to 76% by weight, insoluble carbohydrates 24 to 41% by weight, soluble carbohydrates 0.2 to 2.3% by weight, fats <0.01 to 0.8% by weight. In the microscopic analysis, it was found that for both preparation modalities of the protein-carrier preparations, proteins were included within the cellulose-based fibers as well as agglomerated with them. There were only a few particles of proteins that were not bound to cellulose-based fibers or were agglomerated with each other. In contrast, the proteins were predominantly in condensed (agglomerated) form when using cellulose fibers derived from husks or stalk material was used as TM. Protein condensates encapsulated cellulose fibers; furthermore cellulose fibers were present, in which a detachment of the protein coating was recognizable.

In formulation A), cellulose fibers from husks or stalk material caused a stickiness, whereas this was not the case when using cellulose-based fibers as TM. Patties made with cellulose-based fibers as TM exhibited the best cohesion and best chewability, while patties made with cellulose fibers from husks and stalk material broke and cracked during cooking and formed hard aggregates, which led to a negative evaluation during the tasting.

In the preparation of preparation B), incorporation of whipped egg white was significantly easier to achieve in doughs made with cellulose-based fibers as TM, and there was a more uniform distribution of air bubbles, as compared to doughs made with cellulose fibers from husks or stalk material, where this was not the case. After cooking, preparations made with cellulose-based fibers as TM exhibited significantly greater cohesiveness of the dough mass and less stickiness than was the case with preparations using cellulose fibers from husk or stalk material. In the preparation of preparation C), there was no stabilization of the foam cream mass by the steam treatment when cellulose fibers made from husk or stalk material were used, whereas in the case of preparations made with cellulose-based fibers very good stabilization was achieved. In the sensory evaluation, the preparations in which cellulose-based fibers were used as TM were judged to be significantly more creamy while giving lower perception of fattening sensation than was the case in preparations made with cellulose fibers from husk and stalk material.

There was no chance in physical properties of samples that had been stored over 12 months. There was no microbial load on the samples. The solvability in (uptake of) water of the stored preparations and the qualitative and sensory properties of the preparation products, which had been prepared with the stored samples corresponded to the results given here, which were obtained with these preparations immediately after their preparation.

Example 13

Investigation on the Industrial Production of Baked Goods Made from/with Cellulose-Based Fibers.

The large-scale production of the following preparations was performed: A) chips, B) biscuit and C) gingerbread. Preparation of raw masses:

A) 100 kg of cellulose-based fibers from soybean meal (preparation according to Example 3 (with an arginine solution)) having a moisture content of 70% by weight is combined with 3 kg of a seasoning mixture by an automatic kneading/stirring machine for 2 hours and mixed to a homogeneous dough. The dough mass is pumped by means of a screw pump into a filling device, with which a defined volume of the mass is placed into the molds of a device. After filling, the mold is closed by a vapor permeable counterpart, so that the dough masses are formed into 3 mm thin slices (diameter 5 cm) within this all around form that is sealed upon closure. Subsequently, the entire mold plate is heated to 140° C. for 5 minutes. By opening the forms the chips fall out and are conveyed by belt into an oven in which they are heated to 180° C. for 2 minutes. The cooled chips are then packaged in an anhydrous nitrogen atmosphere, air and vapor tight. In all, 31 kg of chips was obtained. A visual, tactile and sensory examination was performed after storage periods of 2, 6 and 12 months. The appearance remained unchanged, as well as the fracturability and the surface texture. In the tasting, the consistency was rated crispy at all times and a pleasant mouthfeel was indicated. There was no change in the taste characteristics over the course of storage.

B) 50 kg of cellulose-based fibers from corn (preparation according to Example V2 b)) with a residual moisture content of <20% by weight is folded under a whipped mass consisting of 40 kg of egg white and 10 kg of egg yolk and 35 kg of powdered sugar and flavors and 200 g sodium bicarbonate which have been whipped with one another. The flowable dough was filled into bakeware with a diameter of 30 cm, 2 cm high and baked at 180° C. for 20 minutes. After cooling, the biscuits were removed and packaged airtight and vapor-tight under a nitrogen atmosphere. A visual, tactile and sensory examinations were performed after storage periods of 2, 6 and 12 months. The appearance remained unchanged, as well as the resistance to indentations and the surface texture. The consistency was judged to be slightly crispy at the tasting at all times, and the mouthfeel was stated to be soft and rounded. There was no change in the taste properties during storage.

C) 50 kg of cellulose-based fibers of kidney beans (prepared according to Example 4) with a residual moisture of <25% by weight were mixed with 50 kg of ground almonds, 10 kg of chopped candied lemon peel and candied orange peel and 500 g of sodium bicarbonate and a seasoning mixture. The mixture was kneaded under 60 kg of a mass made of eggs and powdered sugar. The dough was portioned after a rest period of 2 hours and rolled flat on baking trays to a height of 1 cm and baked at 180° C. for 20 minutes. After cooling, the dough portions were cut into pieces and packaged air- and vapor-tight. Visual, tactile and sensory examinations were performed after storage periods of 2, 6 and 12 months. The appearance remained unchanged, as well as the resistance to indentations and the surface texture. The consistency was rated at the time of tasting as tender-crispy and a full mouthfeel was stated. There was no change in the appearance, the resistance to indentations or taste properties during storage.

Example 14

Investigation of the Use of Cellulose-Based Fibers as Sugar Substitutes.

The sugar content of the following food products: A) fondant, B), marzipan, C) nougat, D) jam was replaced by 50% (series R50) and 90% (series R90) by the following products: cellulose-based fibers (prepared according to Example 2 V2 a) and Example 3 V1 d)) of pumpkin (KF) and apples (AF), cellulose fibers from wheat husks (WF) and hydroxycellulose (HC). Manufacturing instructions:

A) Original fondant recipe: Swelling of 12 g of gelatin in 60 ml of water which is then gently heated, admixing 10 ml of glycerin, 1 g of salt and flavorings and 90 g of molten hydrogenated coconut oil under stirring. To the mixture 1,000 g powdered sugar is mixed in and finally kneaded into a homogeneous dough. For the preparations with cellulose-based fibers and cellulose fibers from husk material, the formulation is changed by exchanging 50 or 90% by weight of the original amount of powdered sugar for the preparations which had a residual moisture content of 20% by weight, or 5 and 9% by weight, of cellulose ethers. The dough masses obtained are stored airtight over 24 hours and then processed after renewed kneading and evaluated, respectively.

B) For the production of noble marzipan, marzipan almond paste is kneaded with powdered sugar in a weight ratio of 7:3 to a homogeneous mass; deviating from this, preparations containing the tested preparations are prepared by exchanging 50% or 90% by weight of the original amount of powdered sugar by cellulose-based fibers and cellulose fibers from husk material, respectively, which had a residual moisture content of 30% by weight.

C) To make frosting, 500 g powdered sugar was admixed to 10 ml clarified lemon juice until a homogeneous highly viscous mass was formed. Deviating from this, preparations are prepared with the investigated preparations by exchanging 50 or 90% by weight of the original amount of powdered sugar by cellulose-based fibers, and cellulose fibers made from husk material, respectively, which had a residual moisture content of 40% by weight.

D) To make jam, 1000 g of fresh fruit (strawberries) and 500 g gelling sugar (type 2:1) are brought to a boil in a pot and then stirred for 5 minutes on low heat. Deviating from this the original amount of sugar was exchanged by cellulose-based fibers and cellulose fibers from husk material by 50 or 90% where cellulose ethers had a residual moisture content of 10 wt % or 5 and 9 wt %.

As reference products, preparations with the indicated amount of sugar were prepared and evaluated. The preparations were investigated after 24 hours twice in a blinded manner by 4 experts. The following sensory parameters were scored according to a rating scale of 1 (very low/very poor) to 10 (very high/very good): a) sweetness intensity (SI), mouth melting sensation (SG), mouthfeel (MG), spreadability/processability (V), dimensional stability (FS). Results (numerical data are given in Table 4):

Cellulose preparations proved to be unsuitable for the preparation of the preparations B) and C), as there were sticky, unprocessable masses. The test series R90 could not be completed with the cellulose preparations WF and HC, since the preparations A) and D) could not be processed herewith. The sensation of sweetness was slightly reduced by using the cellulose-based fibers and greatly reduced by using cellulose fibers from husks and by cellulose preparations. Cellulose-based fibers improved the processability of the preparations with increasing exchange ratio of the sugar used. The mouth sensation could be improved by using cellulose-based fibers compared to the reference products of the preparations A) to C), whereas mouth sensation was adversely deteriorated when using cellulose fibers. A marked improvement over all reference products was found in the mouth sensation, which increased with increasing proportions of the cellulose-based fibers, while it was adversely deteriorated by cellulose fibers and cellulose preparations (where applicable) compared to the reference products. In preparations C) and D), a significantly better dimensional stability was obtained by using cellulose-based fibers than in the case of the reference product or preparations which had been prepared with cellulose fibers.

Example 15

Investigation of the Use of Cellulose-Based Fibers as a Flour or Starch Substitute.

The content of flour (MG) (wheat flour type 405) or starch (SG) (corn starch) of the following food products: A) pizza dough, B) pasta dough, C) potato dumplings, D) waffles was reduced by 50% (series R50) and 90% (test series R90) by exchange with the following preparations: cellulose-based fibers (prepared according to Examples 3 V2) e) and 4) of camelina (LF) and soybean (SF); cellulose fibers from oat husk (HF); and methylhydroxypropyl cellulose (MHC). Production instructions: A) to each 500 g of flour, 250 g of water, 10 g of yeast, a pinch of salt and 3 tablespoons of olive oil were mixed and kneaded into a homogeneous dough; B) to each 300 g of flour, 1 pinch of salt, 3 eggs and 2 tablespoons of olive oil were added and kneaded to a firm dough; C) to each 100 g of cornstarch, 500 g of pre-cooked and crushed potatoes, 1.5 g of salt, 2 egg yolks, 50 g butter and spices were added and kneaded to a moldable dumpling dough; D) to each 300 g of corn starch, 2 g of sodium bicarbonate, 50 g of sugar, 100 g of butter, 100 ml of milk and 3 tablespoons of vegetable oil were added and stirred to a homogeneous flowable batter. In each case a reference product according to the original formulation was prepared. For the experiments the weights for MG or SG were exchanged against the powdered preparations (for MHC 5% by weight of the respective MG or SG) (test series 1: residual moisture <10% by weight). Following the cooking process, which was carried out in the same way for all preparations, the preparations were examined for appearance, surface condition and sensory properties by 4 experts. The consistency, the crispness (preparations A) and D)), the cooking stability of the product and the taste experience were evaluated. The following sensory parameters were scored according to a rating scale from 1 (very low/very poor) to 10 (very high/very good): a) mealiness (flouriness) (MI), mouth stickiness (MK), mouthfeel (MG), chewability (Z), dimensional stability (FS).

Results (numerical results of test series 1 are given in Table 5):

Preparations made with cellulose-based fibers as a substitute for flour or food starch showed less sticking and stickiness to molds or preparation tools than do the preparations that had been prepared with flour or starch or cellulose fibers made from husk material or those prepared with cellulose preparations. Preparations with MHC were sticky. In the cooking process, the preparations which had been prepared with cellulose-based fibers had a greater cross-section in the preparations A) and D) and a lower detachment of dough components of the preparations B) and C) compared to the other preparations. The rating of the expert tasting gave a better result for all parameters assessed for the preparations made with cellulose-based fibers as compared to those of the other preparations. In the case of the individual evaluations of features, this particularly concerned a lower sensation of a mealiness, a more comfortable chewability, a lower stickiness when chewing the preparations and the absence of a dry mouthfeel. The results of test series 1 and 2 were nearly identical.

Example 16

Investigation on the Use of Cellulose-Based Fibers as a Fat Substitute.

The fat content (butter or margarine) of the following food products: A) Shortcrust pastry, B) Buttercream, C) Nougat, D) Chocolate glaze was replaced by 50% (Series R50) and 90% (Series R90) against the following preparations: cellulose-based fibers (prepared according to Example 1 with arginine, method c) and Example 2 V3 a)) of kidney beans (KBF) and of maize (MF), cellulose fibers of bamboo stalk mass (BF), hydroxycellulose (HC). Manufacturing instructions:

A) 100 g sugar, 200 g margarine, 300 g flour and 1 g salt are kneaded together to a homogeneous mass and allowed to rest for 2 hours; B) 250 g of butter are stirred until fluffy and then 250 g of powdered sugar and 2 egg yolks and aromas are added; C) 300 g of hazelnuts are roasted at 180° C. for 15 minutes and then ground to a powder. 300 g of powdered cane sugar is melted in a pan and the nut powder is stirred in until coated. The still warm mass is kneaded together with 100 g cocoa butter and 200 g cocoa mass to a homogeneous mass; D) 200 g block chocolate is melted and then 250 g soft butter, 200 g melted palm fat and 250 g powdered sugar, 50 ml water, 0.5 g salt and flavors mixed and stirred at low heat until a homogeneous viscous-flowing mass has formed. In deviation preparations with the investigated preparations are prepared by 50 or 90% by weight of the original amount of fats being exchanged by the preparations which had a residual moisture content of 10% by weight (series 1) or had a residual moisture content of 30% by weight (series 2), respectively. For hydroxycellulose (HC), 10% of dry matter were used, that means 5 and 9% by weight. If necessary, water was added to the preparations or they were hydrogenated in order to achieve a comparable consistency.

The evaluation of the preparation A) was carried out after cooling after the standardized baking process, those of the preparations B) and C) immediately after their preparation and that of the preparation D) 24 hours after application to a cake base. Evaluation was done for: Preparation A): brittleness, softness; Preparation B), C) and D): Homogeneity, dimensional stability after extrusion from a spout with a fine star-shaped icing tip, spreadability. All evaluations were performed blinded by 4 experts. The following sensory parameters were rated according to a rating scale from 1 (very low/very bad) to 10 (very high/very good): Creaminess (CI), mouth stickiness (MK), mouth melting sensation (SG), fattening sensation (MI), dimensional stability (FS).

Results: (numerical results of test series 1 are given in table 6):

Cellulose-based fibers caused a lower brittleness of the preparation A) compared to the original formulation or a fat replacement by cellulose fibers from stalk mass or by methylcelluloses. There was the same softness as when using the full amount of fat and a greater softness compared to preparations in which cellulose fibers or methylcellulose had been used. For preparations B), C) and D), the greatest homogeneity was present in preparations made with cellulose-based fibers as compared to the use of the other preparations. Extrusion through a spout with a narrow outlet went well and was evenly possible only by preparations where cellulose-based fibers have been used. In comparison, when using formulations according to the original formulation, a much higher effort was required and when using cellulose fibers, no uniform extrusion result was achievable. The sensory evaluation in terms of melting feeling and creaminess gave an equally good or better (experimental series R90 in preparations A), B) and C) for MF and KBF) evaluation for preparations made with cellulose-based fibers as compared to preparations which had been prepared according to the original formulation, whereas the preparations made with cellulose fibers or with the methylcellulose preparation had markedly lower ratings of these sensory properties. Compared with preparations that had been prepared with the original formulation, preparations prepared with cellulose-based fibers, had a significantly lower fattening sensation (especially in the preparations B), C) and D)) and had a lower mouth stickiness (especially in Preparations C) and D)), as the preparations prepared according to the original formulation or prepared with the other preparations. These properties were also less pronounced (especially in the R90 series) than was the case when using cellulose fibers or methylcellulose. The results of test series 1 and 2 were largely consistent.

Example 17

Investigation on the Freshness Preservation of Food Preparations

The amount that food preparations drying out was investigated on the following preparations: A) dumpling dough, B) pasta dough, C) noble marzipan, D) butter cream from Examples 14-16. From the doughs/preparations according to the original formulation as well as with the cellulose-based fibers and cellulose fibers, made of husks or stems, as well as cellulose preparations, spheres 1 cm in diameter were formed and weighed. The preparations were stored for 48 hours at 25° C. under room air conditions. They were then weighed and the surfaces examined for their appearance, consistency and properties.

Results:

Preparations made with cellulose-based fibers had a significantly lower weight loss (=loss of water) than was the case with the other preparations. The surfaces of these preparations showed no (test series R90) or only slight (test series R50) color changes, which were caused by drying. On the other hand, the preparations which had been prepared according to the original formulation as well as with the comparators showed moderate to marked color changes. Correspondingly, crust formation in the sliced preparations prepared according to the original formulation or with cellulose fibers or cellulose preparations was present to a moderate or pronounced degree, while in the preparations made with cellulose-based fibers, this was only minimal (R50) or nonexistent (R90).

Example 18

Investigation of Stool-Regulating Properties of Cellulose-Based Fibers.

After each 14 days of a roughage-rich diet (preparation phase), 10 subjects received the following diets in consecutive order for 7 days:

Diet 1: protein content 70% by weight, digestible carbohydrates 20% by weight, indigestible carbohydrates 8% by weight, fat <1% by weight, minerals/vitamins 1% by weight.

Diet 2: protein content 70% by weight, digestible carbohydrates 8% by weight, indigestible carbohydrates 20% by weight, fat <1% by weight, minerals/vitamins 1% by weight.

The indigestible carbohydrates of diet 2 consisted of the following preparations: a) flaxseed shells, b) wheat glume fibers (75 μm), c) cellulose-based fibers of carrots, d) cellulose-based fibers of pumpkin, e) hydroxy-methyl cellulose ethers (HMC). The proteins and indigestible carbohydrates were formulated together according to the procedures described in Example 12.

Between the dietary periods, the roughage-rich standard diet, which was also used for preparing the participants before participating, was consumed for 5 days. The occurrence of abdominal complaints (AB), painful intestinal gas production (DG), stool frequency (SF) and stool consistency (SC) were recorded.

Subsequently, after finalizing diet 2 a) to e) 2 subjects each of the diets were continued for 4 weeks (long-term use).

For all subjects, stool samples were analyzed for lactate, acetate and changes in microbial content after 14 days of preparation and after long-term use.

Results:

For all subjects, a roughage-rich standard diet was symptom-free digestible and there was a daily stool frequency with normal consistency. Under diet 1, all subjects experienced abdominal malaise, bloating and a reduction in stool frequency. Stool consistency was described as tough or hard. Under diet 2, the swelling agent (preparation a) partially caused abdominal complaints and a decrease in stool frequency. Under the diet with cellulose fibers, which had been made from husks/stalks material (preparation b)) and with a cellulose preparation (preparation e)), there were abdominal complaints, as well as flatulence and a decrease in stool frequency and a considerable thickening of the stool. During diet 2 with the use of cellulose-based fibers (preparations c) and d)), neither abdominal complaints nor flatulence occurred. The stool frequency and consistency were about as high as those of the roughage-rich diet.

In long-term use, those who continued on diet 2 with preparations a), b), and e) reported the same symptoms as in the short-term use. In persons taking diet 2a) and e), lactate, acetate and the microbiome were unchanged from baseline after the preparing phase. Under the diet 2 c) and d) there had been a significant increase in the concentrations of lactate and acetate and a change in the microbiome. There was no abdominal discomfort and stool frequency and stool consistency was normal in these subjects. Participants who had taken preparations c) and d) experienced weight loss of 2.3 kg to 6.4 kg over the course of 4 weeks.

Example 19

Investigation of Effects of Cellulose-Based Fibers on Stool Regulation in Persons with Chronic Irritable Bowel Syndrome.

Cellulose-based fiber supplementation was performed in 10 subjects with symptoms of chronic irritable bowel syndrome (including flatulence, abdominal discomfort, irregular stool frequency) over 4 weeks. To this end, 10 g (dry weight) of various cellulose-based fibers (including soya, pumpkin, camelina) per day were incorporated into the individual food preparations, such as in a spread to use on bread, a milk or fruit juice beverage, a sauce or in a patty, or in addition to these, taken by the participants to themselves. Attendees were encouraged to document their abdominal discomfort and bowel habits during an initial 14-day documentation phase, and to eat and follow the documented diet, in the subsequent 4-week take-up phase of the cellulose-based fibers, and to continue this documentation. The average degree of symptoms was calculated from the sum of the individual 5-stage degrees (from 0=no to 5=very strong) of the symptoms: flatulence, pain, feeling of fullness, nausea, abdominal pressure, with a maximum possible score of 25 per examination time and member.

Results:

All participants had a daily intake of 10 g to 12 g (dry weight) of cellulose-based fibers. An improvement in abdominal complaints (especially flatulence and pain) was documented by all participants, reducing the mean symptom severity from 15±3 to 4±1. Furthermore, a dietary supplement containing cellulose-based fibers resulted in a significantly more regular stool frequency and a significantly softer stool consistency. In the participants a weight reduction of 2.3±0.2 kg was registered.

Example 20

Investigation of the Industrial Obtainment and Production of Cellulose-Based Fibers 500 kg whole grain of dried corn are filled into a kettle together with 800 liters of a 0.1 molar arginine solution and the kettle contents are stirred for 2 hours at 85° C. Subsequently, the heated slurry is conveyed by means of a screw pump through a pipeline into a colloid mill. The feed line is continuously fed with water in a volume ratio of 8:1. The mixture is conveyed with a volume flow of 500 L/h and a pressure of 1 bar into a colloid mill. The outlet of the colloid mill is connected to a pipeline which, by means of a pump, directs the suspension into a hydrocyclone device. The upper outflow (OL) and lower outflow (UL) of the suspensions are fed to separate vibrating screens (sieve mesh size 100 μm in each). The sieve residue of the OL was charged to a reaction vessel and suspended with water at a ratio of 1:10 by means of a shear mixer for 10 minutes at a temperature of 45° C. Subsequently, while continuously mixing, the suspension is discharge via a pipe to a vibrating screen (screen mesh size 200 μm). The screen residue is fed by means of a conveying device entered into an application device which applied a layer height of 1.5 cm of the cellulose-based fiber mass onto the polypropylene screen (screen mesh size 80 μm) of a vacuum belt screening machine. At the end of belt drying, the mass has a residual moisture content of 30-40% by weight. The easily separable mass is distributed on sieve pallets, which are stacked on top of each other. The pallet stack is moved into a vacuum drying oven in which the cellulose-based fibers are dried to a residual moisture content of <10% by weight, which were subsequently finely ground with a disc mill. The sieve analysis gives an average particle size of 0.2 mm. The particles dissolve quickly in the mouth or in water and are odorless and tasteless. In the chemical analysis (carried out according to Example 1), a content of readily soluble carbohydrates of 0.25% by weight and a content of readily soluble proteins of 0.1% by weight are determined. The water binding capacity (determination according to Example 1) is 660% by weight, the water retention capacity (determination according to Example 9) is 61%. The screen residue from the UL is washed twice with water in a volume ratio of 1:5 and then dried on a belt filter screen device and fed to a further utilization. The filter permeate of the process stages is combined and passed into a settling tank, from which the water that was clarified by sedimentation is used again for further process executions. The sediment of this settling process is separated and dried by means of a belt sieve and fed to a further utilization.

Further Embodiments of the Invention

1. Obtainment and production of cellulose-based fibers by a process consisting of
   a) providing a plant-based starting material containing cellulose-based fibers,
   a1) disintegration of the plant-based starting material from step a) by a thermal and/or mechanical unlocking process,
   b) impregnation of the disintegrated plant-based material from step a1) with an aqueous unlocking solution,
   c) rinsing out of soluble constituents of the plant-based starting material
   d) removal of bound water by a physical process,
   e) obtaining cellulose-based fibers which, upon contact with water, expand to three-dimensional structures and release no or only minimal amounts of readily water-soluble carbohydrates and/or proteins and/or flavorings and/or colorant agents in an aqueous suspension.

2. The method according to item 1, wherein the aqueous unlocking solution of the procedural steps a1) and/or b) contains dissolved amino acids and/or peptides.

3. The method according to any one of items 1 and 2, wherein the one or more of the amino acids in the step a1) and/or b) is/are one or more cationic amino acid (s) and/or the one or more peptide/peptides in step a1) and/or b) contain one or more cationic amino acid (s).

4. Method according to any one of the items 1-3, wherein the one or more cationic amino acid(s) is/are arginine and/or lysine and/or histidine and/or derivatives of these.

5. The method according to any one of items 1-4, wherein one or more aqueous solutions having a pH between 7 and 14 in step a1) and/or b) is used for obtaining and/or production of cellulose-based fibers.

6. The method according to any one of items 1-5, wherein for the obtaining and/or production of cellulose-based fibers, a disintegration of plant-based starting material with or together with an aqueous solution of one or more amino acid (s) and/or a peptide or multiple peptides is carried out.

7. The method according to any one of items 1-6, wherein in addition to one or more amino acid (s) and/or a peptide or more peptides, auxiliary compounds are present in the aqueous solutions for obtainment and/or production of cellulose-based fibers, including sulfites, sulfates, ionic and non-ionic surfactants.

8. Method according to any one of the items 1-7, wherein after process step c1) or c2) and/or d1) or d2) the optional process step c3) and/or d3): conditioning the cellulose-based fibers is carried out.

9. Method according to any one of the items 1-8, in which following the process step c1) or c2) and/or d1) or d2) the process step c3) and/or d3), functionalizing of the surfaces of the cellulose-based fibers is carried out.

10. A method according to any one of items 1-9, wherein cellulose-based fibers containing functional groups and compounds that contain at least one of the elements nitrogen, phosphorus, sulfur, sodium, chloride, calcium, magnesium, zinc, copper, iron or manganese are obtained and/or produced.

11. A method according to any one of items 1-10, wherein cellulose-based fibers having tissue-like 3-dimensional structures are obtained and/or produced with an aspect ratio of 1:1 to 1000:1.

12. The method according to any one of items 1-11, wherein a surface modification of cellulose-based fibers by means of a micro-/nano-emulsion is carried out.

13. The method according to any one of items 1-12, wherein a surface coating of the cellulose-based fibers with a coupling/functional layer, which is effected by electrostatic and/or covalent surface bonding, is carried out.

14. Method according to one of the items 1-13, for the adhesion/incorporation of microorganisms onto/into cellulose-based fibers, for increasing production of the product and/or fermentation performance.

15. A method according to any one of items 1-14, wherein the cellulose-based fibers are obtained and/or produced with a fiber length weight of <20 mg/100 m.

16. Cellulose-based fibers produced by a process according to one of the items 1-15, which are characterized by the formation of three-dimensional structures by the absorption of water and/or a water binding capacity of >200% by weight and/or water retention capacity of >50% and/or absence of readily soluble carbohydrates and proteins and/or absence of flavoring or colorant agents which are released into a water phase.

17. Cellulose-based fibers produced by a process according to any one of items 1-15 for reducing the amount and/or replacing flour/starch in food preparation.

18. Cellulose-base fibers prepared by a process according to any one of items 1-15 for use as oil/fat substitute.

19. Cellulose-based fibers produced by a method according to any one of items 1-15 for the formulation of dissolved or soluble proteins.

20. Condensates/agglomerates of proteins and cellulose-based fibers, prepared by a method according to any one of items 1-15, for improving the conveying behavior and/or shelf life of proteins.

21. Cellulose-based fibers prepared by a process according to any one of items 1-15, as a release agent for cooking products, intended for a roasting, baking, grilling or frying process.

22. Cellulose-based fibers prepared by a process according to any one of items 1-15 for the increase shelf life and preservation of compounds and/or substances and/or organisms.

23. Cellulose-based fibers prepared by a method according to any one of items 1-15 for the incorporation and formulation of compounds into/within lotions and/or creams and/or ointments and/or pastes.

24. Cellulose-based fibers produced by a method according to any one of items 1-15 for improving the absorption behavior and/or the moisturization of/by lotions/creams/ointments or pastes on skin and mucous membranes.

25. Surface-modified cellulose-based fibers prepared by a process according to any one of items 1-15 for the oxidation stabilization of lipid phases.

26. Cellulose-based fibers produced by a method according to any one of items 1-15 for the adhesion/introduction of microorganisms to increase product production and/or fermentation performance.

27. Cellulose-based fibers prepared by a method according to any one of items 1-15 for the treatment of constipation and/or regulation of bowel motility and/or stool consistency.

28. Cellulose-based fibers prepared by a method according to any one of items 1-15 for use as a weight loss food supplement.

29. Cellulose-based fibers produced by a method according to any one of items 1-15 for stimulating salivation and/or reducing unpleasant halitosis.

30. Cellulose-based fibers prepared by a process according to any one of items 1-15 for the binding of aromas and flavorings.

31. Cellulose-based fibers prepared by a method according to any one of items 1-15, for the cultivation of microorganisms/algae.

Tables

TABLE 1

| Preparation | WRR (%) | S 24 (mm) | S O/W (Min) |
|---|---|---|---|
| EF | 82 | 48 | 38 |
| RF | 54 | 50 | 65 |
| KaF | 72 | 44 | 60 |
| HF | 84 | 35 | 45 |
| KüF | 71 | 32 | 40 |
| RF-V | 41 | 68 | 31 |
| KaF-V | 39 | 72 | 29 |
| HF-V | 35 | 71 | 25 |
| KüF-V | 48 | 75 | 22 |
| HC | 32 | 80 | 22 |
| WC | 29 | 87 | 15 |
| HMC 1 | n.d. | 70 | 22 |
| HMC 2 | n.d. | 68 | 18 | n.d. = not definable

TABLE 2

| | Material | SC A | BV (%) | OFB | EDS | LEK | SBW |
|---|---|---|---|---|---|---|---|
| TS 1 | Ref. | – | 100 | 1 | 1 | 1 | 5.6 |
| | SF (TB) | BH | 240 | ++ | ++ | ++ | 9.5 |
| | SF (NB) | BH | 180 | +++ | ++ | +++ | 9.2 |
| | BF (TB) | BH | 250 | ++ | ++ | ++ | 8.9 |
| | BF (NB) | BH | 200 | +++ | ++ | +++ | 9.7 |
| | HC | BH | 80 | – | –– | – | 4.1 |
| | BC | BH | 60 | –– | –– | –– | 3.8 |
| | MCH 1 | BH | 70 | o | – | – | 4 |
| | MCH 2 | BH | 80 | – | – | – | 3.5 |
| TS 2 | Ref. | – | 100 | 1 | 1 | 1 | 6.2 |
| | SF (TB) | ST | 210 | +++ | ++ | + | 9.4 |
| | SF (NB) | ST | 180 | +++ | ++ | +++ | 9.1 |
| | BF (TB) | ST | 220 | ++ | ++ | ++ | 9.8 |
| | BF (NB) | ST | 170 | +++ | ++ | +++ | 10 |
| | HC | ST | 80 | – | –– | –– | 4.5 |
| | BC | ST | 60 | –– | –– | –– | 3.9 |
| | MCH 1 | ST | 70 | o | – | –– | 3.5 |
| | MCH 2 | ST | 70 | – | – | –– | 4.2 |
| TS 3 | Ref. | | 100 | 1 | 1 | 1 | 6.1 |
| | SF (TB) | NHC | 150 | + | + | +++ | 9.2 |
| | SF (NB) | NHC | 160 | o | ++ | +++ | 9 |
| | BF (TB) | NHC | 170 | + | ++ | +++ | 9.4 |
| | BF (NB) | NHC | 140 | + | + | +++ | 9.1 |

TABLE 2-continued

| Material | SC A | BV (%) | OFB | EDS | LEK | SBW |
|---|---|---|---|---|---|---|
| HC | NHC | 60 | -- | -- | - | 4.8 |
| BC | NHC | 70 | --- | -- | -- | 3.1 |
| MCH 1 | NHC | 70 | - | - | - | 4.2 |
| MCH 2 | NHC | 80 | -- | - | - | 4 |

SC = surface coverage;
TS = Test series;
OFB = surface condition;
EDS = resistance to indentations;
LEK = fineness and distribution the entrapped air chambers;
Rating data in each case in comparison to the reference sample (=1):
-- = significantly worse/less,
- = moderately worse/less,
o = equal,
+ = slightly better/stronger,
++ = moderately better/stronger,
+++ = distinct better/stronger than the reference.
SBW = sensory evaluation from 1 (very low/very bad) to 10 (very high/very good), given the median of the individual assessments

TABLE 3

| Preparation | Modality | TM | PK | PZ | Z | K | S | M | FK | MG |
|---|---|---|---|---|---|---|---|---|---|---|
| A) | I | SF | RP | 9 | 10 | 2 | n.a. | n.a. | 1 | 9 |
| A) | II | SF | RP | 10 | 10 | 1 | n.a. | n.a. | 1 | 10 |
| A) | I | SBF | SP | 8 | 9 | 2 | n.a. | n.a. | 1 | 9 |
| A) | II | SBF | SP | 9 | 9 | 2 | n.a. | n.a. | 1 | 9 |
| A) | I | KF | RP | 10 | 10 | 1 | n.a. | n.a. | 1 | 10 |
| A) | II | KF | SP | 10 | 10 | 1 | n.a. | n.a. | 1 | 9 |
| A) | I | WF | RP | 6 | 5 | 4 | n.a. | n.a. | 4 | 5 |
| A) | II | WF | SP | 5 | 5 | 4 | n.a. | n.a. | 4 | 4 |
| B) | I | SF | MP | 10 | n.a. | 1 | 8 | 4 | 1 | 10 |
| B) | II | SF | SP | 9 | n.a. | 2 | 9 | 4 | 1 | 10 |
| B) | I | SBF | SP | 9 | n.a. | 1 | 7 | 3 | 1 | 9 |
| B) | II | SBF | MP | 10 | n.a. | 2 | 8 | 4 | 1 | 10 |
| B) | I | KF | MP | 10 | n.a. | 2 | 8 | 3 | 1 | 9 |
| B) | II | KF | SP | 10 | n.a. | 1 | 8 | 4 | 1 | 9 |
| B) | I | WF | SP | 5 | n.a. | 5 | 4 | 6 | 5 | 4 |
| B) | II | WF | MP | 4 | n.a. | 5 | 3 | 7 | 5 | 3 |
| C) | I | SF | MP | n.a. | n.a. | 2 | 9 | 3 | 1 | 10 |
| C) | II | SF | SP | n.a. | n.a. | 1 | 9 | 3 | 1 | 9 |
| C) | I | SBF | RP | n.a. | n.a. | 1 | 8 | 4 | 1 | 10 |
| C) | II | SBF | RP | n.a. | n.a. | 2 | 9 | 3 | 1 | 10 |
| C) | I | KF | SP | n.a. | n.a. | 2 | 8 | 4 | 1 | 10 |
| C) | II | KF | MP | n.a. | n.a. | 2 | 8 | 3 | 1 | 10 |
| C) | I | WF | MP | n.a. | n.a. | 6 | 4 | 6 | 6 | 4 |
| C) | II | WF | SP | n.a. | n.a. | 5 | 4 | 7 | 5 | 3 |

Modality:
I = TM (moisture content 70-80% by weight) + and PK (residual moisture <5%),
II = TM (residual moisture <5% by weight) + PK (moisture content 80-90% by weight).
TM = carrier material;
PK = protein concentrate.
Sensory evaluation:
PZ = product cohesion,
Z = chewability
K = stickiness,
S = creaminess,
M = fattening sensation
FK = fiberiness/graininess,
MG = mouthfeel.
Rating from 1 (very low/very bad) to 10 (very high/very good).
N/A. = not applicable

TABLE 4

| Preparation | Material | RF (%) | SI | SG | MG | V | FS |
|---|---|---|---|---|---|---|---|
| A) | Original | — | 10 | 6 | 4 | 5 | 7 |
| A) | KF | 50 | 8 | 8 | 5 | 7 | 7 |
| A) | AF | 50 | 8 | 7 | 5 | 6 | 7 |
| A) | WF | 50 | 5 | 4 | 2 | 3 | 3 |
| A) | HC | 50 | 4 | 4 | 2 | 3 | 2 |
| A) | KF | 90 | 7 | 9 | 8 | 9 | 9 |
| A) | AF | 90 | 7 | 9 | 8 | 9 | 9 |
| A) | WF | 90 | 1 | 2 | 2 | 2 | 2 |
| A) | HC | 90 | na | na | na | na | na |
| B) | Original | — | 9 | 6 | 6 | 7 | 7 |
| B) | KF | 50 | 8 | 8 | 8 | 8 | 7 |
| B) | AF | 50 | 7 | 8 | 8 | 8 | 8 |
| B) | WF | 50 | 4 | 4 | 4 | 5 | 5 |
| B) | HC | 50 | na | na | na | na | na |
| B) | KF | 90 | 7 | 9 | 10 | 9 | 9 |
| B) | AF | 90 | 7 | 10 | 9 | 9 | 9 |
| B) | WF | 90 | 2 | 2 | 1 | 2 | 2 |
| B) | HC | 90 | na | na | na | na | na |
| C) | Original | — | 10 | 6 | 5 | 5 | 4 |
| C) | KF | 50 | 8 | 8 | 8 | 8 | 7 |
| C) | AF | 50 | 7 | 8 | 8 | 8 | 8 |
| C) | WF | 50 | 4 | 4 | 3 | 4 | 4 |
| C) | HC | 50 | na | na | na | na | na |
| C) | KF | 90 | 7 | 9 | 10 | 9 | 8 |
| C) | AF | 90 | 6 | 10 | 9 | 9 | 9 |
| C) | WF | 90 | 2 | 1 | 2 | 2 | 2 |
| C) | HC | 90 | na | na | na | na | na |
| D) | Original | — | 9 | 8 | 9 | 8 | 2 |
| D) | KF | 50 | 7 | 8 | 9 | 8 | 6 |
| D) | AF | 50 | 7 | 8 | 8 | 8 | 7 |
| D) | WF | 50 | 4 | 4 | 4 | 8 | 4 |
| D) | HC | 50 | 3 | 4 | 3 | 7 | 3 |
| D) | KF | 90 | 6 | 9 | 9 | 8 | 9 |
| D) | AF | 90 | 5 | 9 | 8 | 9 | 9 |
| D) | WF | 90 | 1 | 2 | 1 | 2 | 2 |
| D) | HC | 90 | na | na | na | na | na |

Material refers to the original recipe ingredient or the Material with wich a replacement has been performed.
SI = Intensity of sweetness, SG = moth melting sensation, MG = mouth sensation (MG), Spreadability/processability(V), dimensional stability (FS).
Rating from 1 (very low/very bad) to 10 (very high), na = not applicable.

TABLE 5

| Preparation | Compound | Substitution (%) | MI | MK | MG | Z | FS |
|---|---|---|---|---|---|---|---|
| A) | Original | — | 6 | 5 | 6 | 5 | 7 |
| A) | LF | 50 | 5 | 3 | 7 | 7 | 7 |
| A) | SF | 50 | 4 | 2 | 7 | 7 | 7 |
| A) | HF | 50 | 7 | 5 | 4 | 3 | 6 |
| A) | HC | 50 | 7 | 4 | 3 | 3 | 6 |
| A) | LF | 90 | 2 | 2 | 8 | 9 | 9 |
| A) | SF | 90 | 3 | 2 | 8 | 9 | 9 |
| A) | HF | 90 | 9 | 5 | 2 | 2 | 6 |
| A) | HC | 90 | 8 | 5 | 2 | 2 | 6 |
| B) | Original | — | 4 | 5 | 6 | 8 | 8 |
| B) | LF | 50 | 4 | 3 | 7 | 8 | 8 |
| B) | SF | 50 | 3 | 3 | 8 | 8 | 8 |
| B) | HF | 50 | 6 | 5 | 3 | 4 | 5 |
| B) | HC | 50 | 5 | 5 | 4 | 4 | 5 |
| B) | LF | 90 | 2 | 2 | 9 | 9 | 9 |
| B) | SF | 90 | 1 | 2 | 9 | 9 | 9 |
| B) | HF | 90 | 8 | 7 | 2 | 2 | 3 |
| B) | HC | 90 | 8 | 7 | 3 | 3 | 4 |
| C) | Original | — | 7 | 7 | 6 | 8 | 4 |
| C) | LF | 50 | 5 | 5 | 8 | 8 | 7 |
| C) | SF | 50 | 5 | 4 | 8 | 8 | 8 |
| C) | HF | 50 | 7 | 6 | 3 | 4 | 4 |
| C) | HC | 50 | 3 | 5 | 4 | 4 | 4 |
| C) | LF | 90 | 3 | 2 | 10 | 9 | 9 |
| C) | SF | 90 | 2 | 2 | 9 | 9 | 8 |
| C) | HF | 90 | 10 | 8 | 1 | 2 | 4 |
| C) | HC | 90 | 9 | 8 | 2 | 2 | 3 |
| D) | Original | — | 7 | 6 | 7 | 8 | 3 |
| D) | LF | 50 | 6 | 6 | 9 | 8 | 8 |
| D) | SF | 50 | 5 | 5 | 8 | 8 | 8 |
| D) | HF | 50 | 7 | 7 | 5 | 5 | 6 |

TABLE 5-continued

| Preparation | Compound | Substitution (%) | MI | MK | MG | Z | FS |
|---|---|---|---|---|---|---|---|
| D) | HC | 50 | 6 | 7 | 5 | 5 | 6 |
| D) | LF | 90 | 4 | 4 | 10 | 9 | 9 |
| D) | SF | 90 | 3 | 3 | 10 | 9 | 9 |
| D) | HF | 90 | 10 | 9 | 1 | 1 | 3 |
| D) | HC | 90 | 9 | 9 | 2 | 1 | 2 |

Substitution Weight amount of the substitution of flour and starch vis-a-vis the orginal formula production (original);
a) mealiness (flouriness) (MI), mouth stickiness (MK), mouthfeel (MG), chewability (Z), dimensional stability (FS).
Evaluation from 1 (very low/very bad) to 10 (very high/very good)

TABLE 5

| Preparation | Compound | Substitution (%) | CI | MK | SG | MI | FS |
|---|---|---|---|---|---|---|---|
| A) | Original | — | 4 | 6 | 4 | 5 | 7 |
| A) | KBF | 50 | 6 | 3 | 6 | 3 | 7 |
| A) | MF | 50 | 6 | 2 | 6 | 3 | 7 |
| A) | BF | 50 | 3 | 5 | 4 | 3 | 6 |
| A) | HC | 50 | 3 | 4 | 4 | 3 | 6 |
| A) | KBF | 90 | 8 | 1 | 8 | 2 | 9 |
| A) | MF | 90 | 8 | 1 | 8 | 2 | 9 |
| A) | BF | 90 | 1 | 5 | 2 | 4 | 6 |
| A) | HC | 90 | 2 | 5 | 2 | 4 | 6 |
| B) | Original | — | 7 | 8 | 8 | 10 | 6 |
| B) | KBF | 50 | 8 | 5 | 8 | 5 | 8 |
| B) | MF | 50 | 8 | 5 | 8 | 5 | 8 |
| B) | BF | 50 | 6 | 5 | 3 | 6 | 6 |
| B) | HC | 50 | 6 | 6 | 4 | 4 | 5 |
| B) | KBF | 90 | 10 | 2 | 9 | 2 | 9 |
| B) | MF | 90 | 10 | 2 | 9 | 2 | 9 |
| B) | BF | 90 | 1 | 6 | 2 | 6 | 6 |
| B) | HC | 90 | 2 | 6 | 2 | 6 | 6 |
| C) | Original | — | 7 | 9 | 6 | 8 | 6 |
| C) | KBF | 50 | 7 | 4 | 8 | 8 | 7 |
| C) | MF | 50 | 8 | 5 | 7 | 5 | 8 |
| C) | BF | 50 | 6 | 6 | 3 | 5 | 8 |
| C) | HC | 50 | 5 | 5 | 4 | 4 | 6 |
| C) | KBF | 90 | 10 | 2 | 10 | 2 | 9 |
| C) | MF | 90 | 10 | 2 | 9 | 2 | 8 |
| C) | BF | 90 | 3 | 8 | 1 | 8 | 6 |
| C) | HC | 90 | 9 | 8 | 2 | 2 | 3 |
| D) | Original | — | 5 | 6 | 7 | 8 | 8 |
| D) | KBF | 50 | 7 | 4 | 9 | 5 | 8 |
| D) | MF | 50 | 7 | 4 | 8 | 4 | 8 |
| D) | BF | 50 | 4 | 5 | 5 | 6 | 6 |
| D) | HC | 50 | 5 | 6 | 5 | 5 | 6 |
| D) | KBF | 90 | 9 | 1 | 10 | 2 | 9 |
| D) | MF | 90 | 10 | 2 | 10 | 1 | 9 |
| D) | BF | 90 | 1 | 9 | 1 | 10 | 3 |
| D) | HC | 90 | 2 | 9 | 2 | 10 | 2 |

Substitution Weight amount of the substitution of fat vis-a-vis the original formnla production (original);
CI = creminess, MK = mouth stickiness, SG = mouth melting sensation, MI = fattening sensation, FS = dimension stability.
Evaluation from 1 (very low/very bad) to 10 (very high/very good)

What is claimed is:

1. Unlocked, decompacted cellulose-based fibers obtained from a plant-based starting material by a method for obtaining and producing of unlocked decompacted cellulose-based fibers, the method comprising the following steps:
   a) providing a disintegrated or non-disintegrated plant-based starting material containing compacted cellulose-based fibers, compacted with at least one organic compound selected from:
      readily water-soluble organic compounds comprising proteins and carbohydrates; and/or
      poorly water-soluble organic compounds comprising complex carbohydrates; and or
      water-insoluble organic solids comprising lignin-rich shells,
   a1) disintegration of the non-disintegrated plant-based starting material from step a) to obtain a penetrability of aqueous unlocking solutions and wettability of the compacted cellulose-based fibers by means of a thermal and/or a mechanical and/or an aqueous disintegration process to obtain a dry or moist disintegrated plant-based starting material,
   b) impregnation of the disintegrated plant-based starting material from step a) or impregnation of the plant-based starting material from step a1) after thermal and/or mechanical and/or aqueous disintegration until obtaining a moisture content of greater than 20 wt. % and a complete hydration of the readily soluble organic compounds with an aqueous unlocking solution of dissolved unlocking substances containing at least one dissolved amino acid with a molar mass of less than 400 g/mol and a solubility of at least 35 g/L in water at 20° C. and/or peptides from 2 to 50 of these amino acids for unlocking the compacted cellulose-based fibers,
   c1) suspending and mixing the impregnated disintegrated starting material of step b) in an aqueous dispensing volume having a weight ratio to the dry matter of the plant-based starting material of 2:1 to 300:1 and decompacting the unlocked, compacted, cellulose-based fibers in the dispensing volume until a hydration volume of the unlocked cellulose-based fibers of >200% by volume is reached in order to obtain isolated unlocked, decompacted cellulose-based fibers,
   c2) in the case of the presence of water-insoluble organic solids according to step a), separation of the unlocked, decompacted, cellulose-based fibers of step c1) from the water-insoluble organic solids,
   d1) separation of the unlocked, decompacted cellulose-based fibers by filtration and/or centrifugation from the suspension of step c1) or c2) and obtaining unlocked, decompacted, cellulose-based fibers, and
   d2) drying the unlocked, decompacted cellulose-based fibers,
   wherein the unlocked, decompacted, cellulose-based fibers have an aspect ratio after swelling in water of longitudinal diameter to transverse diameter of 1:1 to 1000:1 and a water binding capacity of >200% by weight and have a water retention capacity of >50%,
   wherein the plant-based starting material is a non-woody plant-based starting material having a lignin content of <10% by weight selected from the group comprising seeds, grains, kernels, beans, beet plants, vegetables, fruits, berries, cucumbers, blossoms and roots or tubers and nuts,
   wherein the unlocked, decompacted cellulose-based fibers have a hydration volume of >100% by volume and are present in isolated/singular form,
   wherein the unlocked, decompacted, cellulose-based fibers form three-dimensional spatial structures by the absorption of water,
   wherein the unlocked, decompacted, cellulose-based fibers contain <1% by weight of readily water-soluble carbohydrates, proteins and flavoring or colorants,
   wherein the unlocked, decompacted, cellulose-based fibers have a fiber length weight (coarseness)<70 mg/100 mg,
   wherein the unlocked, decompacted, cellulose-based fibers are water insoluble,
   wherein the unlocked, decompacted, cellulose-based fibers are nature-identical fiber materials directly obtained from the plant-based starting material without a change in the polymeric structures, and wherein unlocked, decompacted cellulose-based fibers are not:
- fibrillar cellulose fibers obtained from wood pulp;
- derivatives of cellulose fibers prepared by mechanically comminuting and hydrolyzing;
- water-soluble cellulose esters, cellulose acetates or cellulose nitrates;
- cellulose ethers including hydroxyethyl cellulose (HEC), hydroxypropyl cellulose (HPC), methyl ethyl cellulose (MEC), hydroxyethylmethyl cellulose (HEMC), hydroxypropyl methyl cellulose (HPMC), hydroxypropylmethyl cellulose (HPMC);
- cellulose derivatives which have been prepared by a chemical process for polymer-analogous reaction;
- cellulosic fibers from husks, stems and stalks;
- lignified cellulose fibrils or cellulose fibers present in lignified or woody plant materials.

2. The unlocked, decompacted, cellulose-based fibers according to claim 1 with a fiber length weight (Coarseness) <20 mg/100 m.

3. The unlocked, decompacted, cellulose-based fibers according to claim 1, wherein the unlocked, decompacted, cellulose-based fibers contain more than 2.5% by weight of chemical compounds and functional groups comprising nitrogen, phosphorus, sulfur, sodium, chloride, calcium, magnesium, zinc, copper, iron and/or manganese, which do not correspond to a carbohydrate.

4. Use of the unlocked, decompacted cellulose-based fibers according to claim 1 for the cultivation of microorganisms and algae, for binding odors and flavors, for stimulating the salivation and/or for reducing an unpleasant halitosis, as body weight-reducing dietary supplement, for increasing the product production of microorganisms and/or their fermentation performance, for oxidation stabilization of lipid phases, for improving the adsorption behavior and/or the moisturizing effect of/by lotions/creams/ointments or pastes on/of the skin and mucous membranes, for the introduction and formulation of compounds, lotions and/or creams and/or ointments and/or pastes, for the conservation and preservation of compounds and/or substances and/or organisms, as separating agents of cooking products, intended for frying, baking and baking, roasting/frying, grilling or deep fat frying processes, to improve storability and/or protein shelf life, for formulation of dissolved or soluble proteins, for use as an oil/fat substitute and as a substitute for flour/starch in food preparation.

5. The unlocked, decompacted cellulose-based fibers according to claim 1 for use in the treatment of constipation and/or regulation of intestinal activity and/or stool consistency.

6. A method for obtaining and producing of unlocked decompacted cellulose-based fibers comprising the following steps:
a) providing a disintegrated or non-disintegrated plant-based starting material containing compacted cellulose-based fibers, compacted with at least one organic compound selected from:
  - readily water-soluble organic compounds comprising proteins and carbohydrates; and or
  - poorly water-soluble organic compounds comprising complex carbohydrates; and or
  - water-insoluble organic solids comprising lignin-rich shells,
a1) disintegration of the non-disintegrated plant-based starting material from step a) to obtain a penetrability of aqueous unlocking solutions and wettability of the compacted cellulose-based fibers by means of a thermal and/or a mechanical and/or an aqueous disintegration process to obtain a dry or moist disintegrated plant-based starting material,
b) impregnation of the disintegrated plant-based starting material from step a) or impregnation of the plant-based starting material from step a1) after thermal and/or mechanical and/or aqueous disintegration until obtaining a moisture content of greater than 20 wt. % and a complete hydration of the readily soluble organic compounds with an aqueous unlocking solution of dissolved unlocking substances containing at least one dissolved amino acid with a molar mass of less than 400 g/mol and a solubility of at least 35 g/L in water at 20° C. and/or peptides from 2 to 50 of these amino acids for unlocking the compacted cellulose-based fibers,
c1) suspending and mixing the impregnated disintegrated starting material of step b) in an aqueous dispensing volume having a weight ratio to the dry matter of the plant-based starting material of 2:1 to 300:1 and decompacting the unlocked, compacted, cellulose-based fibers in the dispensing volume until a hydration volume of the unlocked cellulose-based fibers of >200% by volume is reached in order to obtain isolated unlocked, decompacted cellulose-based fibers,
c2) in the case of the presence of water-insoluble organic solids according to step a), separation of the unlocked, decompacted, cellulose-based fibers of step c1) from the water-insoluble organic solids,
d1) separation of the unlocked, decompacted cellulose-based fibers by filtration and/or centrifugation from the suspension of step c1) or c2) and obtaining unlocked, decompacted, cellulose-based fibers,
d2) drying the unlocked, decompacted cellulose-based fibers.

7. The method according to claim 6 further comprising step c3) and/or d3), which follows after step c1) or c2) or after step d1) and/or d2), for the conditioning/functionalization of cellulose-based fibers, which is carried out, comprising the steps:
- providing an aqueous solution containing conditioning/functionalizing compounds comprising amino acids and/or peptides, carboxylic acids, carbonates, alcohols, sugar compounds, cellulose ethers,
- suspending and dispensing the cellulose-based fibers from step c1) or c2) or after step d1) and/or d2) in the solution containing conditioning/functionalizing compounds until surface conditioning with the conditioning/functionalizing compounds on the inner and outer surfaces of the cellulose-based fibers is achieved,
- phase separation of the conditioned/functionalized cellulose-based fibers by means of filtration and/or centrifugation,
wherein in step e) conditioned and/or functionalized, unlocked, decompacted cellulose-based fibers are obtained which have anti-static and/or hygroscopic, hydrophilic or hydrophobic and/or conductive surface properties.

8. The method according to claim 6, wherein the at least one dissolved amino acid according to step b) has a molar mass in the range of 75 g/mol to 350 g/mol and/or a solubility of at least 75 g/L in water at 20° C. and/or it is α-, β- or γ-amino acids and/or proteinogenic and/or non-proteinogenic amino acids.

9. The method according to claim 6, wherein the aqueous unlocking solution according to step a1) and/or step b) has a pH value between 7 and 14.

10. The method according to claim 6, wherein the readily water-soluble organic compounds have a water solubility of >100 g/L at 20° C.

11. Unlocked, decompacted cellulose-based fibers obtainable by a method according to claim 7.

12. Cellulose-based fibers obtained from a plant-based starting material by a method comprising the following steps:
a) providing a disintegrated or non-disintegrated plant-based starting material containing compacted cellulose-based fibers, compacted with at least one organic compound selected from:
readily water-soluble organic compounds comprising proteins and carbohydrates; and or
poorly water-soluble organic compounds comprising complex carbohydrates; and or
water-insoluble organic solids comprising lignin-rich shells,
a1) disintegration of the non-disintegrated plant-based starting material from step a) to obtain a penetrability of aqueous unlocking solutions and wettability of the compacted cellulose-based fibers by means of a thermal and/or a mechanical and/or an aqueous disintegration process to obtain a dry or moist disintegrated plant-based starting material,
b) impregnation of the disintegrated plant-based starting material from step a) or impregnation of the plant-based starting material from step a1) after thermal and/or mechanical and/or aqueous disintegration until obtaining a moisture content of greater than 20 wt. % and a complete hydration of the readily soluble organic compounds with an aqueous unlocking solution of dissolved unlocking substances containing at least one dissolved amino acid with a molar mass of less than 400 g/mol and a solubility of at least 35 g/L in water at 20° C. and/or peptides from 2 to 50 of these amino acids for unlocking the compacted cellulose-based fibers,
c1) suspending and mixing the impregnated disintegrated starting material of step b) in an aqueous dispensing volume having a weight ratio to the dry matter of the plant-based starting material of 2:1 to 300:1 and decompacting the unlocked, compacted, cellulose-based fibers in the dispensing volume until a hydration volume of the unlocked cellulose-based fibers of >200% by volume is reached in order to obtain isolated unlocked, decompacted cellulose-based fibers,
c2) in the case of the presence of water-insoluble organic solids according to step a), separation of the unlocked, decompacted, cellulose-based fibers of step c1) from the water-insoluble organic solids,
d1) separation of the unlocked, decompacted cellulose-based fibers by filtration and/or centrifugation from the suspension of step c1) or c2) and obtaining unlocked, decompacted, cellulose-based fibers,
d2) drying the unlocked, decompacted cellulose-based fibers,
wherein the unlocked, decompacted, cellulose-based fibers have an aspect ratio after swelling in water of longitudinal diameter to transverse diameter of 1:1 to 1000:1 and a water binding capacity of >200% by weight and have a water retention capacity of >50%,
wherein the plant-based starting material is a non-woody plant-based starting material having a lignin content of <15% by weight,
wherein the unlocked decompacted cellulose-based fibers have a hydration volume of >100% by volume and are present in isolated/singular form,
wherein the unlocked, decompacted, cellulose-based fibers form three-dimensional spatial structures by the absorption of water,
wherein the unlocked, decompacted, cellulose-based fibers contain <1% by weight of readily water-soluble carbohydrates, proteins and flavoring or colorants,
wherein the unlocked, decompacted cellulose-based fibers have a fiber length weight (coarseness)<70 mg/100 mg,
wherein the unlocked, decompacted cellulose-based fibers are water insoluble,
wherein the cellulose-based fibers are nature-identical fiber materials
directly obtained from the plant-based starting material without a change in the polymeric structures,
wherein the cellulose-based fibers consist of polymeric saccharide compounds containing functional side groups, such as SH—, OH—, NH— or COOH-groups, or are covalently linked to other compounds, and
wherein the cellulose-based fibers are not:
fibrillar cellulose fibers obtained from wood pulp;
derivatives of cellulose fibers prepared by mechanically comminuting and hydrolyzing;
water-soluble cellulose esters, cellulose acetates or cellulose nitrates;
cellulose ethers including hydroxyethyl cellulose (HEC), hydroxypropyl cellulose (HPC), methyl ethyl cellulose (MEC), hydroxyethylmethyl cellulose (HEMC), hydroxypropyl methyl cellulose (HPMC), hydroxypropylmethyl cellulose (HPMC);
cellulose derivatives which have been prepared by a chemical process for polymer-analogous reaction;
cellulosic fibers from husks, stems and stalks;
lignified cellulose fibrils or cellulose fibers present in lignified or woody plant materials.

13. Unlocked, decompacted cellulose-based fibers obtained from a plant-based starting material by a method for obtaining and producing of unlocked decompacted cellulose-based fibers, the method comprising the following steps:
a) providing a disintegrated or non-disintegrated plant-based starting material containing compacted cellulose-based fibers, compacted with at least one organic compound selected from:
readily water-soluble organic compounds comprising proteins and carbohydrates; and/or
poorly water-soluble organic compounds comprising complex carbohydrates; and or
water-insoluble organic solids comprising lignin-rich shells,
a1) disintegration of the non-disintegrated plant-based starting material from step a) to obtain a penetrability of aqueous unlocking solutions and wettability of the compacted cellulose-based fibers by means of a thermal and/or a mechanical and/or an aqueous disintegration process to obtain a dry or moist disintegrated plant-based starting material,
b) impregnation of the disintegrated plant-based starting material from step a) or impregnation of the plant-based starting material from step a1) after thermal and/or mechanical and/or aqueous disintegration until obtaining a moisture content of greater than 20 wt. % and a complete hydration of the readily soluble organic compounds with an aqueous unlocking solution of dissolved unlocking substances containing at least one dissolved amino acid with a molar mass of less than 400 g/mol and a solubility of at least 35 g/L in water at 20° C. and/or peptides from 2 to 50 of these amino acids for unlocking the compacted cellulose-based fibers, c1) suspending and mixing the impregnated disintegrated starting material of step b) in an aqueous dispensing volume having a weight ratio to the dry matter of the plant-based starting material of 2:1 to 300:1 and decompacting the unlocked, compacted, cellulose-based fibers in the dispensing volume until a hydration volume of the unlocked cellulose-based fibers of >200% by volume is reached in order to obtain isolated unlocked, decompacted cellulose-based fibers, c2) in the case of the presence of water-insoluble organic solids according to step a), separation of the unlocked, decompacted, cellulose-based fibers of step c1) from the water-insoluble organic solids, d1) separation of the unlocked, decompacted cellulose-based fibers by filtration and/or centrifugation from the suspension of step c1) or c2) and obtaining unlocked, decompacted, cellulose-based fibers, d2) drying the unlocked, decompacted cellulose-based fibers, wherein the unlocked, decompacted, cellulose-based fibers have an aspect ratio after swelling in water of longitudinal diameter to transverse diameter of 1:1 to 1000:1 and a water binding capacity of >200% by weight and have a water retention capacity of >50%, wherein the plant-based starting material is a non-woody plant-based starting material having a lignin content of <105% by weight, selected from the group comprising seeds, grains, kernels, beans, beet plants, vegetables, fruits, berries, cucumbers, blossoms and roots or tubers and nuts;

wherein the unlocked, decompacted cellulose-based fibers have a hydration volume of >100% by volume and are present in isolated/singular form, wherein the unlocked, decompacted, cellulose-based fibers form three-dimensional spatial structures by the absorption of water, wherein the unlocked, decompacted, cellulose-based fibers contain <1% by weight of readily water-soluble carbohydrates, proteins and flavoring or colorants, wherein the unlocked, decompacted, cellulose-based fibers have a fiber length weight (coarseness)<70 mg/100 mg, wherein the unlocked, decompacted, cellulose-based fibers are water insoluble, wherein the unlocked, decompacted cellulose-based fibers are nature-identical fiber materials directly obtained from the plant-based starting material without a change in the polymeric structures, wherein the unlocked, decompacted cellulose-based fibers consist of polymeric saccharide compounds containing functional side groups, such as SH—, OH—, NH— or COOH— groups, or are covalently linked to other compounds, and wherein unlocked, decompacted cellulose-based fibers are not:
fibrillar cellulose fibers obtained from wood pulp;
derivatives of cellulose fibers prepared by mechanically comminuting and hydrolyzing;
water-soluble cellulose esters, cellulose acetates or cellulose nitrates;
cellulose ethers including hydroxyethyl cellulose (HEC), hydroxypropyl cellulose (HPC), methyl ethyl cellulose (MEC), hydroxyethylmethyl cellulose (HEMC), hydroxypropyl methyl cellulose (HPMC), hydroxypropylmethyl cellulose (HPMC);
cellulose derivatives which have been prepared by a chemical process for polymer-analogous reaction;
cellulosic fibers from husks, stems and stalks;
lignified cellulose fibrils or cellulose fibers present in lignified or woody plant materials.

* * * * *